United States Patent
Yu et al.

(10) Patent No.: US 10,526,342 B2
(45) Date of Patent: Jan. 7, 2020

(54) ORGANIC HETEROCYCLIC COMPOUND AND LIGHT-EMITTING DEVICE COMPRISING SAME

(71) Applicant: SFC CO., LTD., Cheongju-si (KR)

(72) Inventors: Taejung Yu, Yongin-si (KR); Yeong-Tae Choi, Yongin-si (KR); Bong-Hyang Lee, Busan (KR); Byung-Sun Yang, Namwon-si (KR); Se-Jin Lee, Daejeon (KR)

(73) Assignee: SFC CO., LTD., Cheongju-si (KR)

( * ) Notice: Subject to any disclaimer, the term of this patent is extended or adjusted under 35 U.S.C. 154(b) by 188 days.

(21) Appl. No.: 15/561,041

(22) PCT Filed: Apr. 5, 2016

(86) PCT No.: PCT/KR2016/003485
§ 371 (c)(1),
(2) Date: Sep. 23, 2017

(87) PCT Pub. No.: WO2016/167505
PCT Pub. Date: Oct. 20, 2016

(65) Prior Publication Data
US 2018/0072753 A1    Mar. 15, 2018

(30) Foreign Application Priority Data
Apr. 16, 2015    (KR) .................. 10-2015-0053728

(51) Int. Cl.
*C07D 487/04*    (2006.01)
*C07D 495/04*    (2006.01)
(Continued)

(52) U.S. Cl.
CPC ......... *C07D 495/04* (2013.01); *C07D 403/04* (2013.01); *C07D 487/04* (2013.01);
(Continued)

(58) Field of Classification Search
None
See application file for complete search history.

(56) References Cited

U.S. PATENT DOCUMENTS 9,118,021 B2 * 8/2015 Lee .................. H05B 33/14
2014/0117326 A1 * 5/2014 Lee .................. C09K 11/06
257/40

FOREIGN PATENT DOCUMENTS

CN    102264698 A    11/2011
CN    102603748 A *  7/2012   ........... C07D 487/04
(Continued)

OTHER PUBLICATIONS

SciFinder Search (May 24, 2019).*
(Continued)

*Primary Examiner* — Vu A Nguyen
(74) *Attorney, Agent, or Firm* — STIP Law Group, LLC

(57) ABSTRACT

The present invention relates to an organic light-emitting compound represented by Chemical Formula A and an organic light-emitting device. In Chemical Formula A, X, Y, Z, and the substituents $R_1$ to $R_8$, and $R_{11}$ to $R_{20}$ are as defined in the specification.

[Chemical Formula A]

(Continued)

Z:

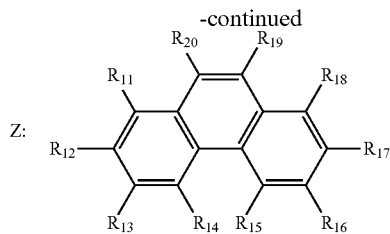

10 Claims, 1 Drawing Sheet

(51) Int. Cl.
  *C07D 491/04* (2006.01)
  *C09K 11/06* (2006.01)
  *H01L 51/00* (2006.01)
  *H01L 51/50* (2006.01)
  *C07D 403/04* (2006.01)
  *C07D 491/048* (2006.01)
(52) U.S. Cl.
  CPC .......... *C07D 491/048* (2013.01); *C09K 11/06* (2013.01); *H01L 51/0072* (2013.01); *H01L 51/5016* (2013.01); *C09K 2211/1088* (2013.01); *C09K 2211/1092* (2013.01)

(56) References Cited

FOREIGN PATENT DOCUMENTS

| | | |
|---|---|---|
| CN | 102603748 A | 7/2012 |
| CN | 103570735 A | 2/2014 |
| CN | 103804333 A | 5/2014 |
| JP | 2010166070 A | 7/2010 |
| KR | 1020100074081 A | 7/2010 |
| KR | 1020110013220 A | 2/2011 |
| KR | 1020120081539 A | 7/2012 |
| KR | 1020140019082 A | 2/2014 |
| KR | 1020140055137 A | 5/2014 |
| KR | 1020140057439 A | 5/2014 |

OTHER PUBLICATIONS

Office action from China National Intellectual Property Administration of 2016800190520, dated Dec. 19, 2018.
International Search Report of PCT/KR2016/003485, dated Apr. 5, 2016, English Translation.
Office Action from China National Intellectual Property Administration of 201680019052.0, dated Jul. 24, 2019.

* cited by examiner

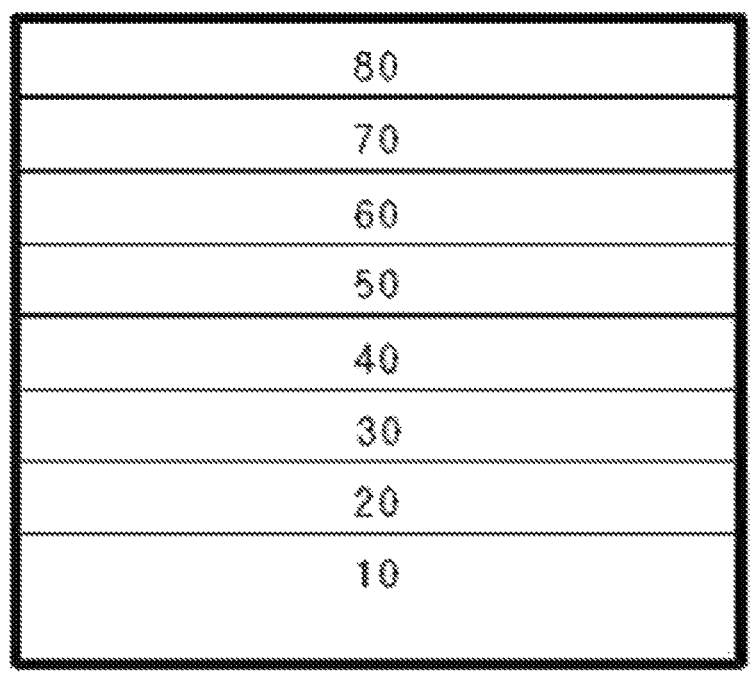

ORGANIC HETEROCYCLIC COMPOUND AND LIGHT-EMITTING DEVICE COMPRISING SAME

CROSS-REFERENCE TO RELATED APPLICATIONS

This application is the U.S. National Phase under 35 U.S.C. § 371 of International Application No PCT/KR2016/003485 filed on Apr. 05, 2016, which in turn claims the benefit of Korean Application No. 10-2015-0053728 filed on Apr. 16, 2015, the disclosures of which are incorporated by reference into the present application.

TECHNICAL FIELD

The present invention relates to a novel heterocyclic compound and an organic light-emitting device comprising the same.

BACKGROUND ART

In general, the term "organic light-emitting phenomenon" refers to a phenomenon in which electrical energy is converted to light energy by means of an organic material.

An organic light-emitting device using the organic light-emitting phenomenon has a structure usually including an anode, a cathode, and an organic material layer interposed therebetween. In this regard, the organic material layer may have, for the most part, a multilayer structure consisting of different materials, for example, a hole injection layer, a hole transport layer, a light-emitting layer, an electron transport layer, and an electron injection layer. In the organic light-emitting device having such a structure, application of a voltage between the two electrodes injects a hole from the anode and an electron from the cathode to the organic layer. In the luminescent zone, the hole and the electron recombine to produce an exciton. When the exciton returns to the ground state from the excited state, the molecule of the organic layer emits light. Such an organic light-emitting device is known to have characteristics such as self-luminescence, high luminance, high efficiency, low driving voltage, a wide viewing angle, high contrast, and high-speed response.

The materials used as organic layers in organic light-emitting devices may be divided into luminescent materials and charge-carrying materials, for example, a hole injection material, a hole transport material, an electron injection material, and an electron transport material. As for the luminescent materials, there are two main families according to molecular weight: those based on small molecules and those employing polymers. The light-emitting mechanism forms the basis for classification of the luminescent materials as fluorescent or phosphorescent materials, which use excitons in singlet and triplet states, respectively. Further, luminescent materials may be divided according to color into blue, green, and red light-emitting materials. Further, yellow and reddish yellow light-emitting materials have been developed in order to achieve more natural colors.

Meanwhile, when a single material is employed as the luminescent material, intermolecular actions cause the wavelength of maximum luminescence to shift toward a longer wavelength, resulting in reduced color purity and light emission efficiency due to the light attenuation. In this regard, a host-dopant system may be used as a luminescent material so as to increase the color purity and the light emission efficiency through energy transfer.

This is based on the principle whereby, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of dopant because the wavelength of the host moves to the wavelength range of the dopant.

In order for organic light-emitting devices to sufficiently exhibit the aforementioned outstanding properties, materials accounting for organic layers in the devices, for example, hole injection materials, hole transport materials, light-emitting materials, electron transport materials, electron injection materials, etc., should be based on stable and effective materials in advance.

Application of an electric current to such an organic light-emitting device induces the injection of holes and electrons from the anode and the cathode, respectively. After being transported respectively by a hole transport layer and an electron transport layer, the injected holes and electrons recombine in a light-emitting layer to produce excitons. The excitons return to the ground state, emitting light. According to the light-emitting mechanism, the light is classified as fluorescence emission with singlet transition to singlet and phosphorescence emission with triplet transition singlet. The fluorescence and the phosphorescence may be used as luminescent light sources of organic light-emitting devices.

In fluorescent organic light-emitting devices, only the formation of singlet excitons results in the emission of useful radiation, and thus there is a theoretical limit of 25% in the internal quantum efficiency of fluorescent organic light-emitting devices. On the other hand, phosphorescent light, which uses triplet excitons, has been extensively studied because its emission efficiency is far superior to that of fluorescent light.

So far, the most widely known phosphorescent host material is CBP, and organic light-emitting devices employing a hole barrier layer of BCP, BAlq, etc. are also known.

However, although devices employing phosphorescent materials are higher in terms of efficiency than those employing fluorescent materials, conventional phosphorescent host materials, such as BAlq or CBP, have room for improvement because they require high driving voltages and are unsatisfactory in terms of lifespan.

With regard to related arts pertaining to such phosphorescent materials for use in light-emitting devices, reference may be made to Korean Patent Publication No. 10-2011-0013220 A (Feb. 9, 2011), which discloses an organic compound having a 6-membered aromatic or heteroaromatic ring frame grafted with an aromatic heterocyclic ring, and Japanese Patent Publication No. 2010-166070 A (Jul. 29, 2010), which discloses an organic compound having a substituted or unsubstituted pyrimidine or quinazoline frame grafted with an aryl or heteroaryl ring.

Despite enormous efforts to prepare luminescent materials for use in organic light-emitting devices or electron transport materials, there is still a continued need to develop organic light-emitting devices that exhibit higher light emission efficiency and which can be driven at low voltages.

DETAILED DESCRIPTION OF THE INVENTION

Technical Problem

Accordingly, a purpose of the present invention is to provide a novel organic compound that is useful for a light-emitting layer in an organic light-emitting device and which exhibits a long lifespan, a low driving voltage, and outstanding emission efficiency.

Another purpose of the present invention is to provide an organic light-emitting diode including the organic compound.

Technical Solution

To accomplish the above purposes, an aspect of the present invention provides an organic light-emitting compound represented by the following Chemical Formula A:

[Chemical Formula A]

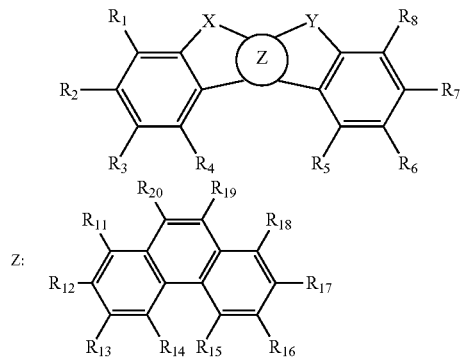

wherein,
the substituents $R_1$ to $R_8$, and $R_{11}$ to $R_{20}$, which may be the same or different, are each independently any one selected from among a hydrogen, a deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkylgermanium of 1 to 30 carbon atoms, a substituted or unsubstituted of 1 to 30 carbon atoms arylgermanium, a cyano, a nitro, and a halogen, Z is a substituted or unsubstituted phenanthrene ring wherein two adjacent radicals selected from among $R_{11}$ to $R_{20}$ are respective single bonds involved in forming a 5-membered, fused ring bearing X in Chemical Formula A, two other adjacent radicals selected from among $R_{11}$ to $R_{20}$ are respective single bonds involved in forming a 5-membered, fused ring bearing Y in Chemical Formula A, X and Y may be the same or different and are each any one selected from among $CR_{21}R_{22}$, S, O, and $NR_{23}$
wherein the substituents $R_{21}$ to $R_{23}$ are defined as for $R_1$ to $R_8$.

In accordance with another aspect thereof, the present invention provides an organic light-emitting device, including a first electrode; a second electrode facing the first electrode; and an organic layer interposed between the first electrode and the second electrode, wherein the organic layer includes at least one of the organic compounds of the present invention.

Advantageous Effects

Exhibiting excellent emission efficiency, long lifespan and low driving voltage properties, the organic compounds of the present invention, when used as phosphorescent hosts, can be available for the fabrication of stable and excellent devices.

BRIEF DESCRIPTION OF THE DRAWINGS

FIG. 1 is a schematic diagram of an organic light-emitting device according to one embodiment of the present invention.

MODE FOR CARRYING OUT THE INVENTION

Below, a detailed description will be given of the present invention.

The present invention provides an organic light-emitting compound, represented by the following Chemical Formula A, for use in a light-emitting layer of an organic light-emitting device:

[Chemical Formula A]

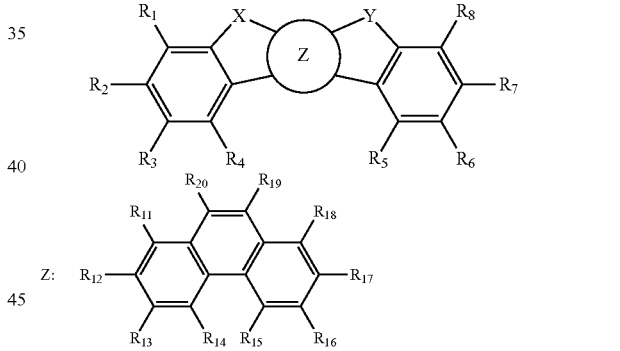

wherein,
the substituents $R_1$ to $R_8$, and $R_{11}$ to $R_{20}$, which may be the same or different, are each independently any one selected from among a hydrogen, a deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkylgermanium of 1 to 30 carbon atoms, a substituted or unsubstituted of 1 to 30 carbon atoms arylgermanium, a cyano, a nitro, and a halogen, Z is a substituted or unsubstituted phenanthrene ring wherein two adjacent radicals selected from among $R_{11}$ to $R_{20}$ are respective single bonds involved in forming a 5-membered, fused ring bearing X in Chemical Formula A, two other adjacent radicals selected from among $R_{11}$ to $R_{20}$ are respective single bonds involved in forming a 5-membered, fused ring bearing Y in Chemical Formula A, X and Y may be the same or different and are each any one selected from among $CR_{21}R_{22}$, S, O, and $NR_{23}$ wherein the substituents $R_{21}$ to $R_{23}$ are defined as for $R_1$ to $R_8$, wherein the term 'substituted' in the expression "substituted or unsubstituted" means having at least one substituent selected from the group consisting of deuterium, a cyano, a halogen, a hydroxy, a nitro, an alkyl of 1 to 24 carbon atoms, an halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, an heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms such as in "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of the substituent. For instance, a phenyl group with a butyl at the para position falls within the scope of an aryl of 6 carbon atoms although it is substituted with a butyl radical of 4 carbon atoms.

As used herein, the term "aryl" means an organic radical derived from an aromatic hydrocarbon by removing one hydrogen atom and encompasses a 5- to 7-membered and preferably a 5- or 6-membered monocyclic ring or fused ring system. In addition, the aromatic system may further include a fused ring that is formed by adjacent substituents, if present, on the aryl radical.

Examples of the aryl include phenyl, naphthyl, biphenyl, terphenyl, anthryl, indenyl, fluorenyl, phenanthryl, triphenylenyl, pyrenyl, perylenyl, chrysenyl, naphthacenyl, and fluoranthenyl, but are not limited thereto.

At least one hydrogen atom on the aryl radical may be substituted by a deuterium atom, a halogen atom, a hydroxy, a nitro, a cyano, a silyl, an amino (—$NH_2$, —NH(R), —N(R') (R") wherein R' and R" are each independently an alkyl of 1 to 10 carbon atoms, in this case called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms.

The substituent heteroaryl used in the compound of the present invention refers to a cyclic aromatic system of 2 to 24 carbon atoms bearing one to three heteroatoms selected from among N, O, P, Se, Te, Si, Ge, and S. In the aromatic system, two or more rings may be fused. One or more hydrogen atoms on the heteroaryl may be substituted by the same substituents as on the aryl.

Examples of the substituent alkyl useful in the present invention include methyl, ethyl, propyl, isobutyl, sec-butyl, tert-butyl, pentyl, iso-amyl, and hexyl. At least one hydrogen atom of the alkyl may be substituted by the same substituent as in the aryl.

Examples of the substituent alkoxy used in the compounds of the present invention include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative of the silyl useful in the present invention are trimethylsilyl, triethylsilyl, triphenylsilyl, trimethoxysilyl, dimethoxyphenylsilyl, diphenylmethylsilyl, silyl, diphenylvinylsilyl, methylcyclobutylsilyl, and dimethylfurylsilyl. At least one hydrogen atom in the silyl may be substituted by the same substituent as in the aryl.

The compound, represented by Chemical Formula A, of the present invention is characterized by being a heterocyclic compound having at least seven fused rings, wherein two adjacent carbon atoms at positions 1 to 10 in the substituted or unsubstituted phenanthrene ring of the following Diagram 1 are connected to the ring moiety of the following Diagram 2, which may be substituted or unsubstituted at positions 4 to 7, respectively through single bonds at positions 2 and 3 to form a fused ring as a 5-membered ring bearing X, and another two adjacent carbon atoms at positions 1 to 10 in the phenanthrene ring are connected to the ring moiety of the following Diagram 2, which may be substituted or unsubstituted at positions 4 to 7, respectively through single bonds at positions 2 and 3 to form a fused ring as a 5-membered ring bearing Y.

[Diagram 1]

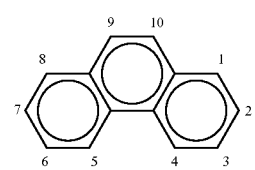

[Diagram 2]

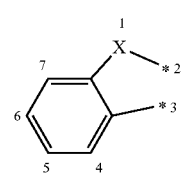

[Diagram 3]

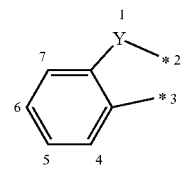

In greater detail, the ring moiety bearing X of Diagram 2 and the ring moiety bearing X of Diagram 3 may be bonded only to one side ring radical or respectively to the opposite side ring radicals in the phenanthrene ring of Diagram 1 to form fused rings. Alternatively, one of the ring moieties of Diagrams 2 and 3 may be bonded to the central ring radical of the phenanthrene ring at positions 9 and 10 while the other may be bonded to either of the opposite side ring radicals of the phenanthrene ring at two adjacent positions selected from among positions 1 to 8.

In the organic light-emitting compound represented by Chemical Formula A in accordance with one embodiment of the present invention, the 5-membered rings respectively bearing X and Y may both be formed on one ring radical of the phenanthrene ring.

That is, Z in Chemical Formula A is a substituted or unsubstituted phenanthrene ring in which the substituents $R_{11}$ and $R_{12}$ may be respective single bonds participating together in the formation of a fused ring as a 5-membered ring bearing X and the substituents $R_{13}$ and $R_{14}$ may be respective single bonds participating together in the formation of a fused ring as a 5-membered ring bearing Y.

For instance, the organic light-emitting compound of the present invention may be a compound represented by Chemical Formula A in which carbon atoms at positions 1 and 2 in the phenanthrene ring of Diagram 1 may be members of a fused ring as a 5-membered ring bearing X while carbon atoms at positions 3 and 4 may be members of a fused ring as a 5-membered ring bearing Y.

In the organic light-emitting compound represented by Chemical Formula A in accordance with another embodiment of the present invention, the 5-membered rings bearing X and Y may be formed respectively on opposite side ring radicals of the phenanthrene ring.

That is, Z in Chemical Formula A is a substituted or unsubstituted phenanthrene ring in which two adjacent substituents from among $R_{11}$ to $R_{14}$ may be respective single bonds participating together in the formation of a fused ring as a 5-membered ring bearing X and two adjacent substituents from among $R_{15}$ to $R_{18}$ may be respective single bonds participating together in the formation of a fused ring as a 5-membered ring bearing Y.

For example, the organic light-emitting compound of the present invention may be a compound represented by Chemical Formula A in which carbon atoms at positions 1 and 2 in the phenanthrene ring of Diagram 1 may be members of a fused ring as a 5-membered ring bearing X while carbon atoms at positions 6 and 7 are members of a fused ring as a 5-membered ring bearing Y. Various other combinations may also be true of the compound.

In the organic light-emitting compound according to another embodiment of the present invention, one of the ring moieties may be bonded to the phenanthrene ring at positions 9 and 10 while the other may be bonded at two adjacent positions selected from among positions 1 to 8.

For example, the organic light-emitting compound of the present invention may be a compound represented by Chemical Formula A in which carbon atoms at positions 9 and 10 in the phenanthrene ring of Diagram 1 may be members of a fused ring as a 5-membered ring bearing X while carbon atoms at positions 1 and 2 are members of a fused ring as a 5-membered ring bearing Y.

In Chemical Formula A, at least one of X and Y may be $NR_{23}$. That is, the heterocyclic compound of Chemical Formula A has at least seven fused rings a part of which includes a carbazole when X and/or Y corresponds to $NR_{23}$.

In the present invention, when at least one of X and Y is $NR_{23}$, $R_{23}$ may be a substituted or unsubstituted heteroaryl of 2 to 50 carbon atoms.

According to an embodiment of the present invention, $R_{23}$ may be any one heteroaryl selected from among the following Structural Formulas A to O:

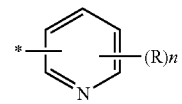

[Structural Formula A]

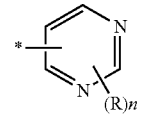

[Structural Formula B]

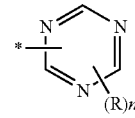

[Structural Formula C]

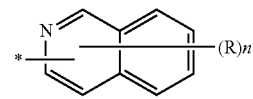

[Structural Formula D]

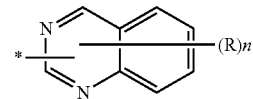

[Structural Formula E]

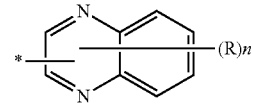

[Structural Formula F]

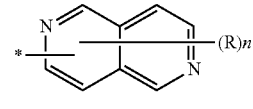

[Structural Formula G]

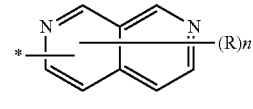

[Structural Formula H]

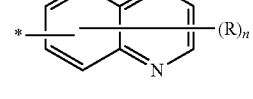

[Structural Formula I]

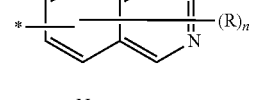

[Structural Formula J]

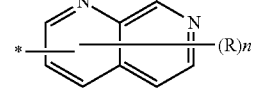

[Structural Formula K]

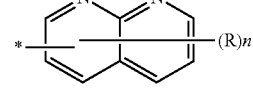

[Structural Formula L]

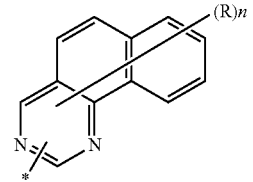

[Structural Formula M]

[Structural Formula N]

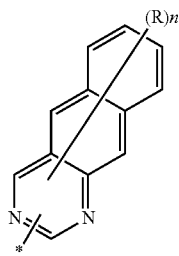

[Structural Formula C-1]

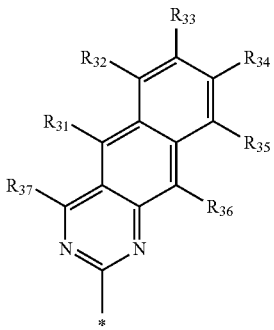

[Structural Formula O]

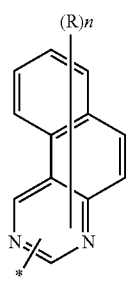

[Structural Formula D-1]

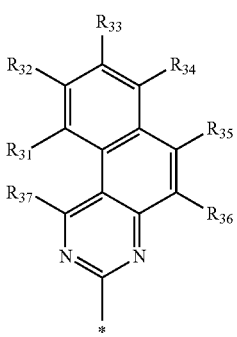

wherein the substituent R is as defined for $R_1$ to $R_8$ and may form a saturated or unsaturated ring with adjacent ones, and, n is an integer of 1 to 7.

According to another embodiment, $R_{23}$ may be any one of the following Structural Formulas A-1 to E-1:

[Structural Formula A-1]

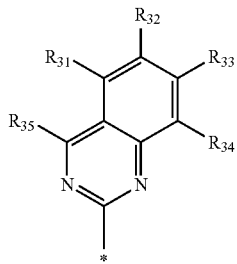

[Structural Formula E-1]

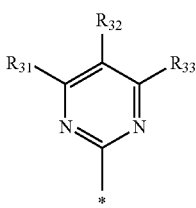

wherein, the substituents R31 to R37, which may be the same or different, are each independently any one selected from among a hydrogen, a deuterium, a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted a substituted or unsubstituted heteroaryl of 2 to 50 carbon atoms bearing O, N, or S as a heteroatom, a cyano, a nitro, and a halogen.

According to another embodiment of the present invention, the organic light-emitting compound may be any one selected from among [Compound 1] to [Compound 128]:

[Structural Formula B-1]

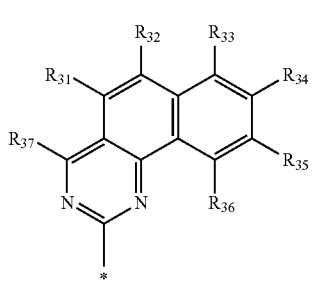

<Compound 1>
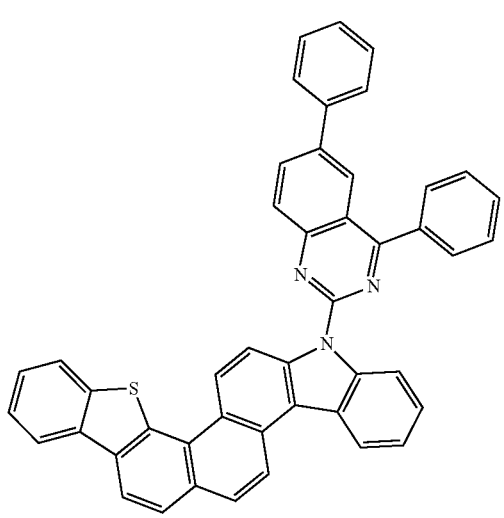
<Compound 2>
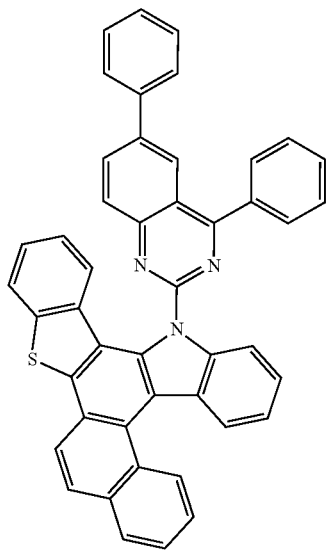
<Compound 3>
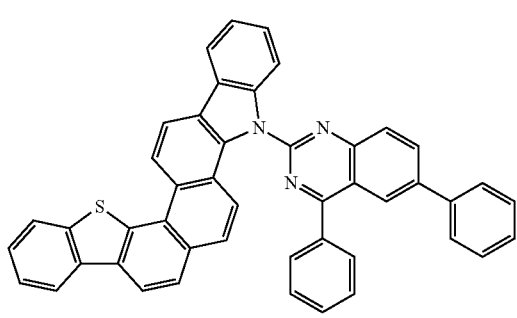
<Compound 4>
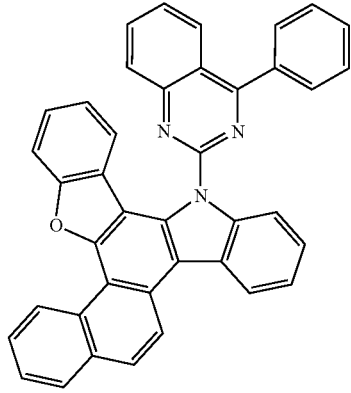
<Compound 5>
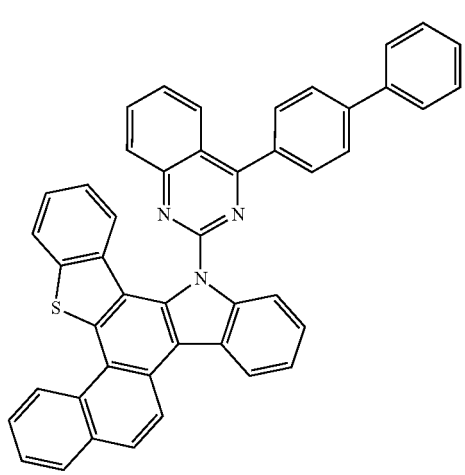
<Compound 6>
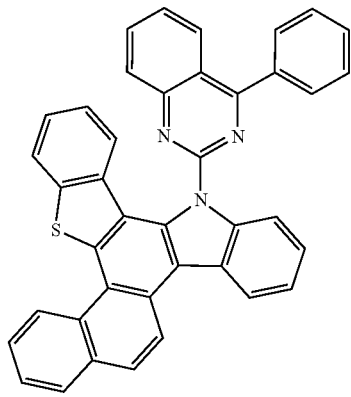

-continued
<Compound 7>
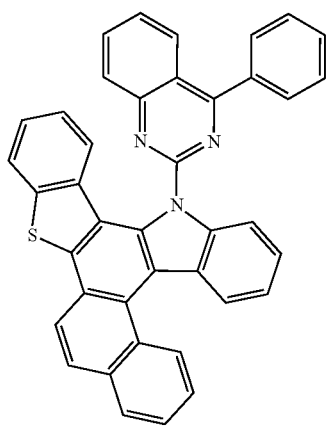
<Compound 8>
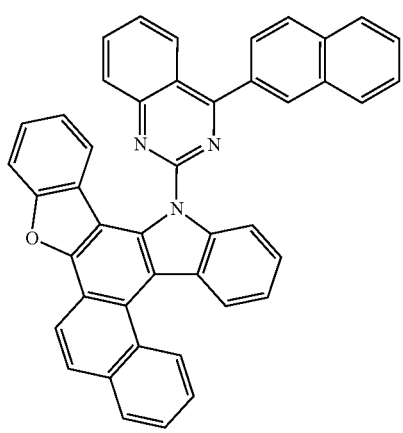
<Compound 9>
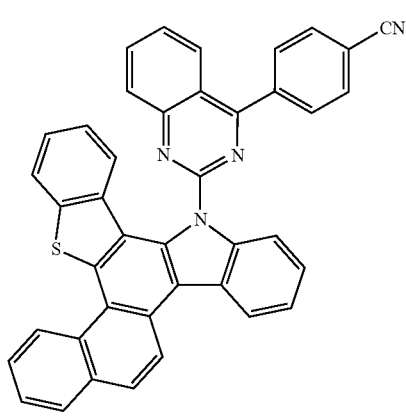
-continued
<Compound 10>
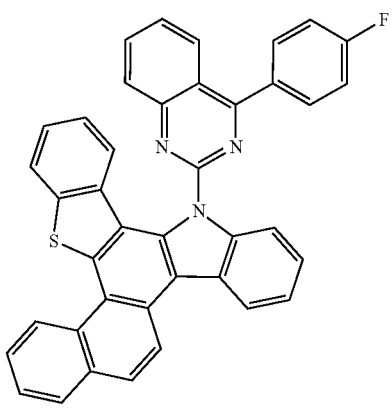
<Compound 11>
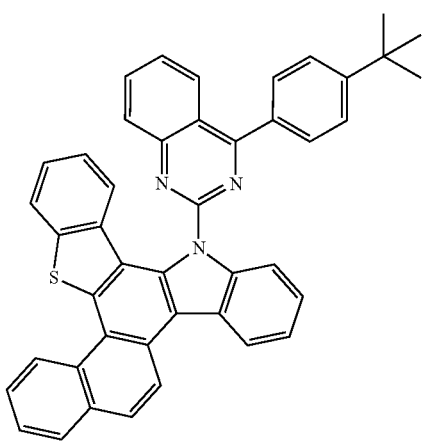
<Compound 12>
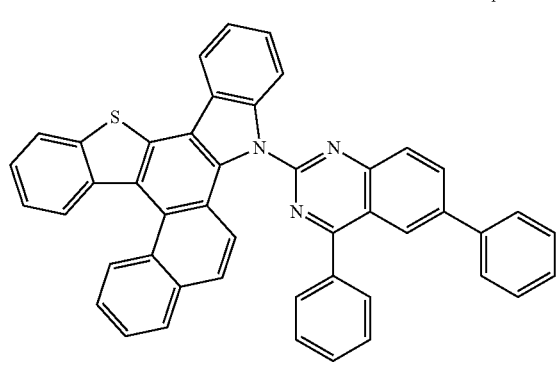

<Compound 13>
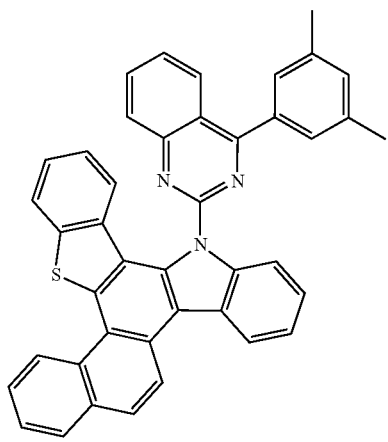
<Compound 14>
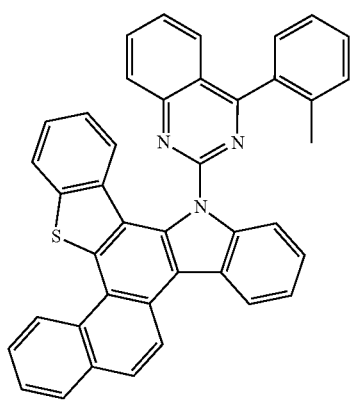
<Compound 15>
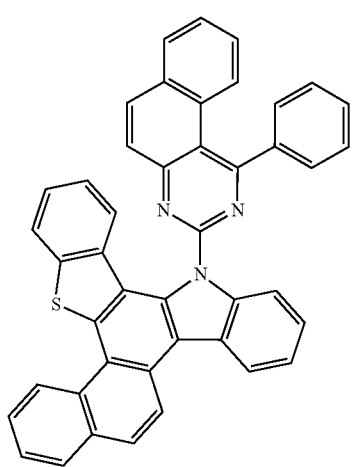
<Compound 16>
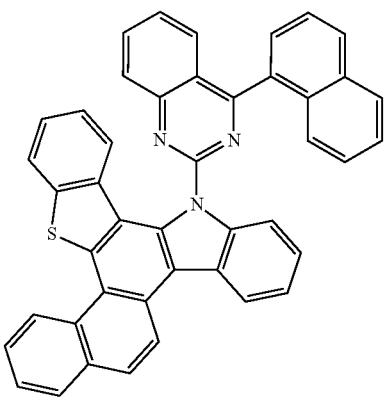
<Compound 17>
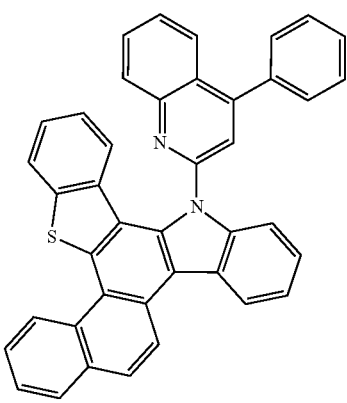
<Compound 18>
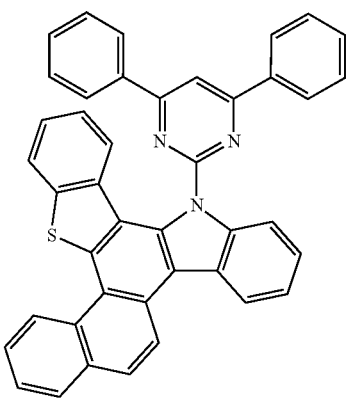
<Compound 19>
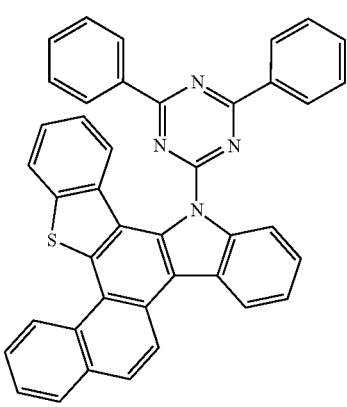

<Compound 20>
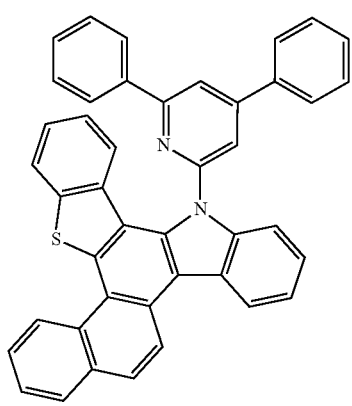
<Compound 21>
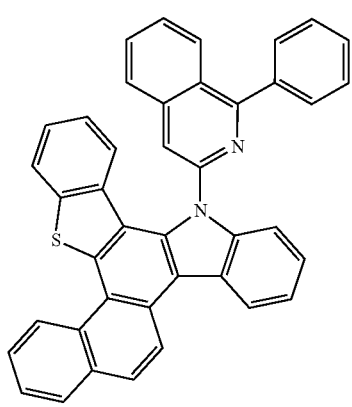
<Compound 22>
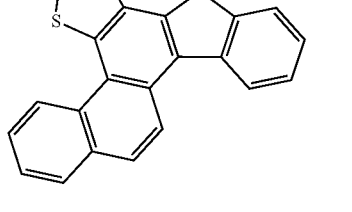
<Compound 23>
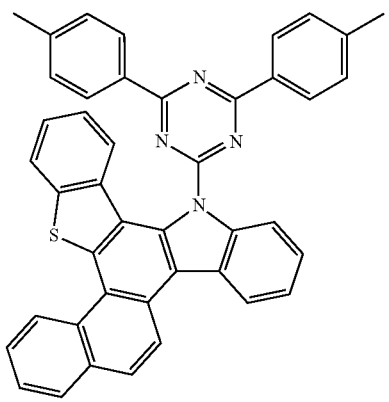
<Compound 24>
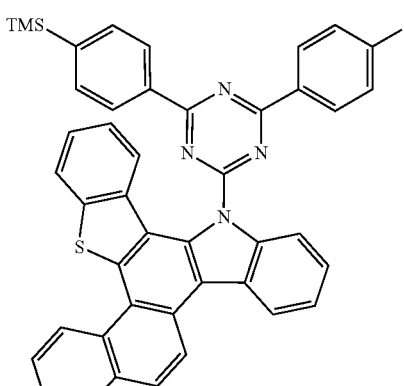
<Compound 25>
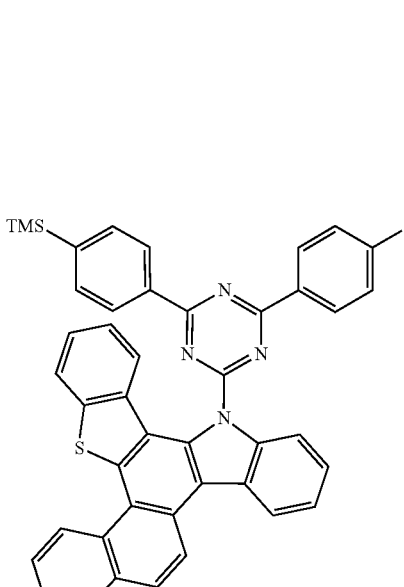
<Compound 26>
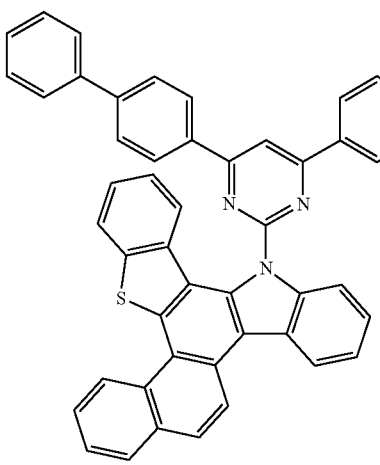

<Compound 27>
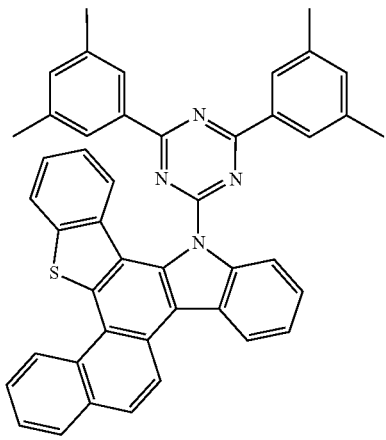
<Compound 28>
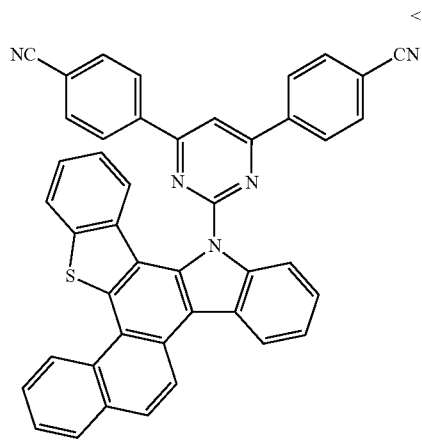
<Compound 29>
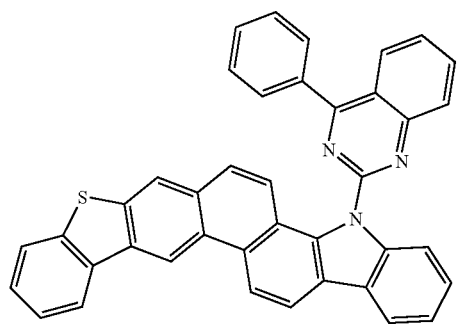
<Compound 30>
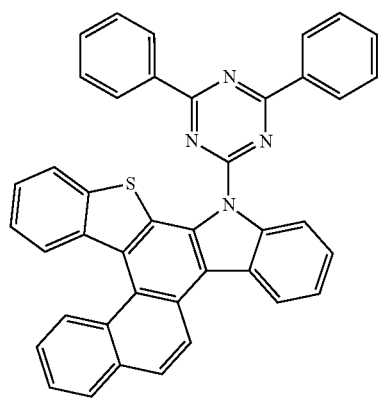
<Compound 31>
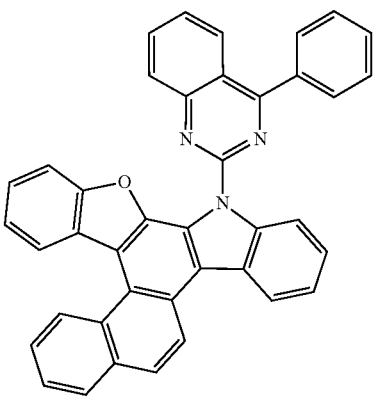
<Compound 32>
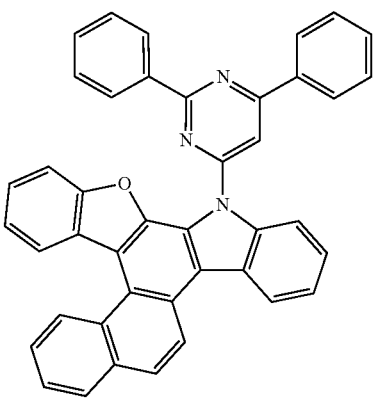
<Compound 33>
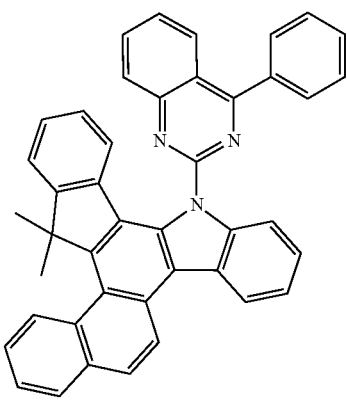
<Compound 34>
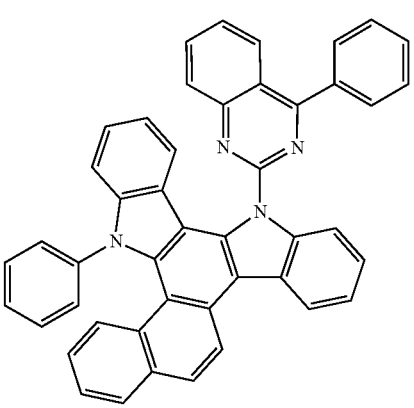

<Compound 35>
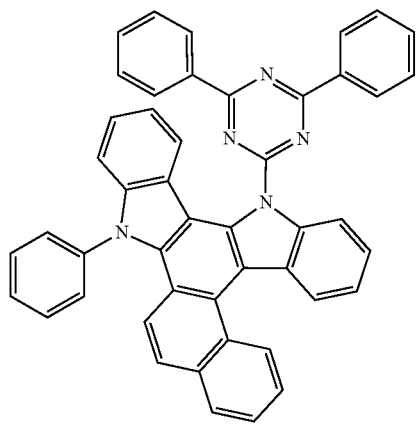
<Compound 36>
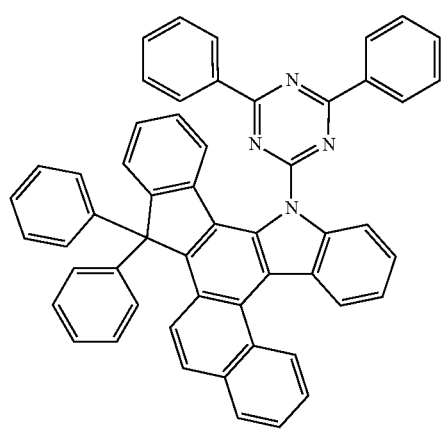
<Compound 37>
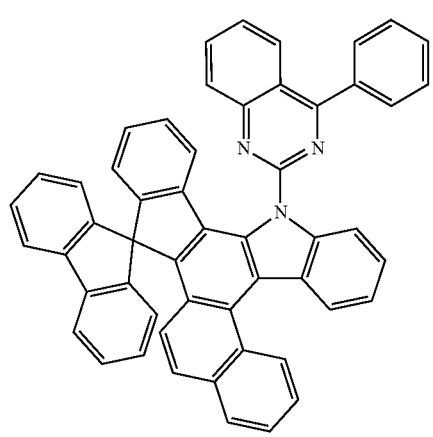
<Compound 38>
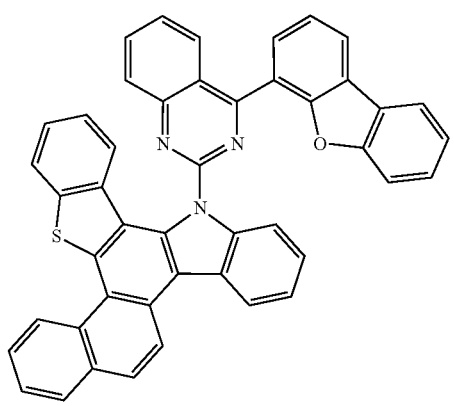
<Compound 39>
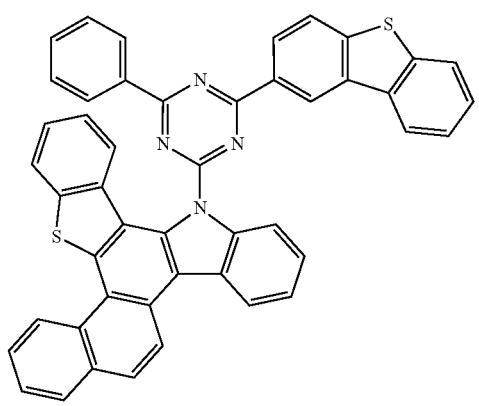
<Compound 40>
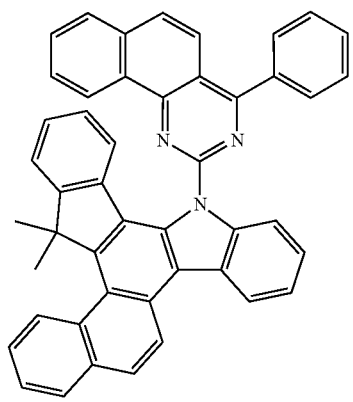
<Compound 41>
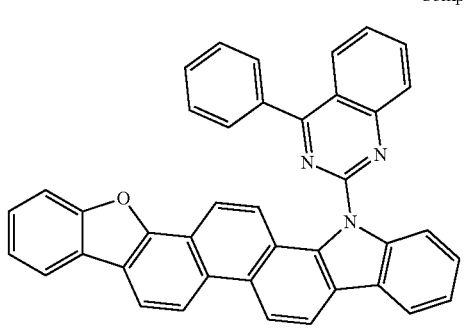

<Compound 42>
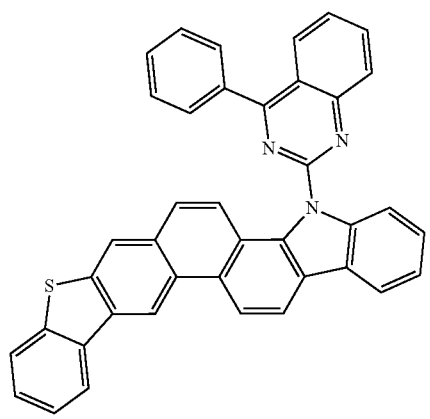
<Compound 43>
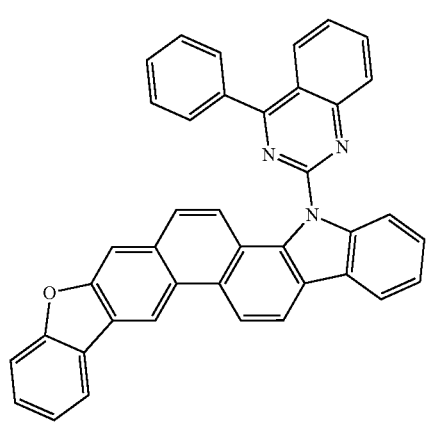
<Compound 44>
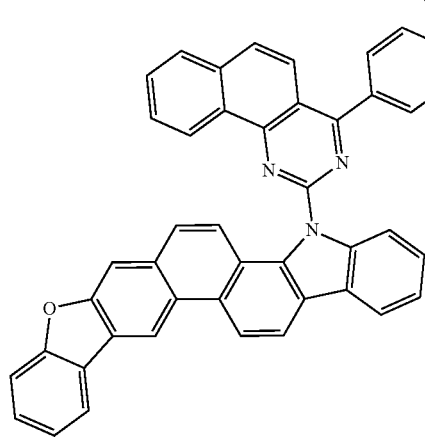
<Compound 45>
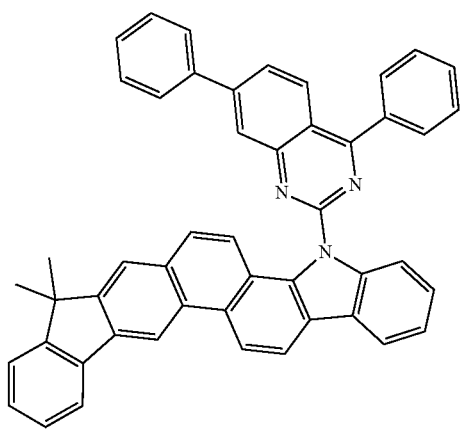
<Compound 46>
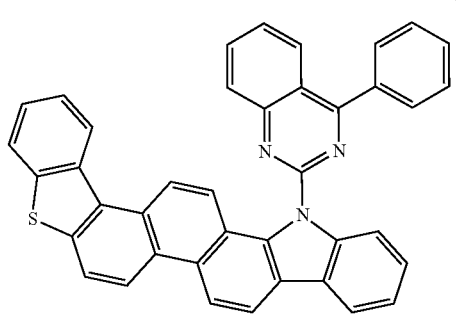
<Compound 47>
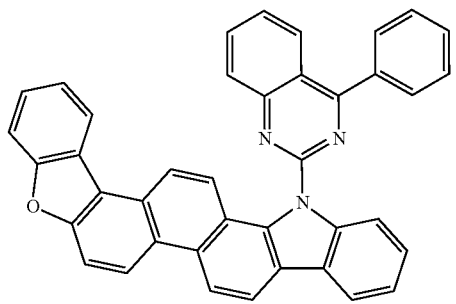
<Compound 48>
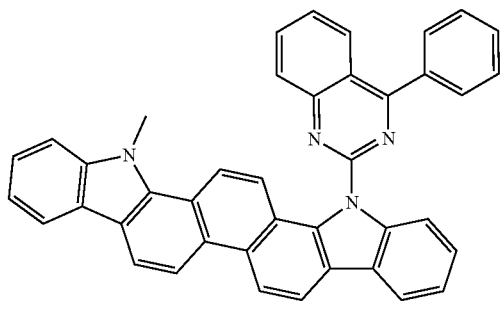

<Compound 49>
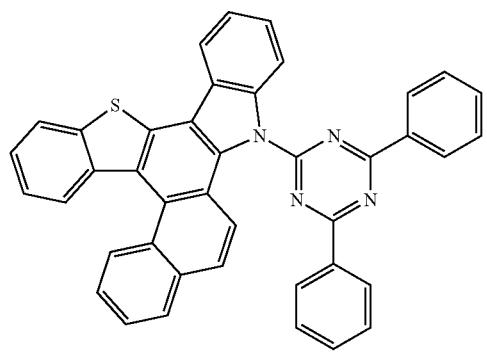
<Compound 53>
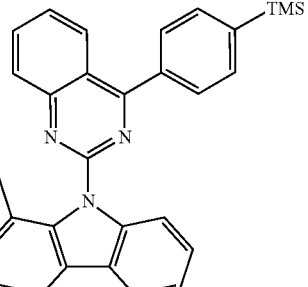
<Compound 54>
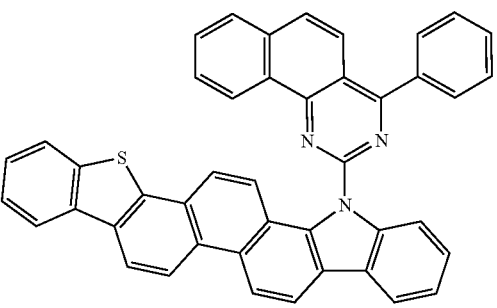
<Compound 50>
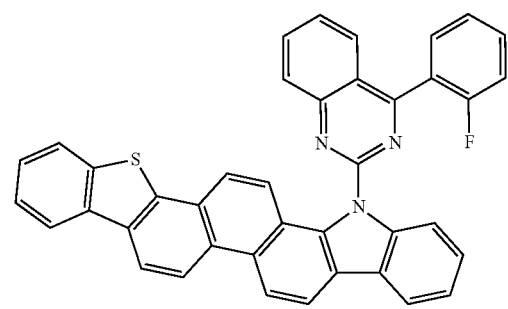
<Compound 55>
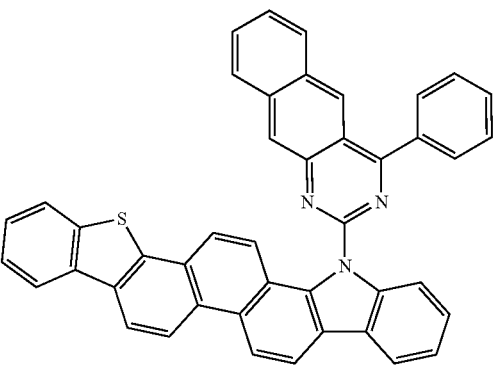
<Compound 51>
<Compound 52>
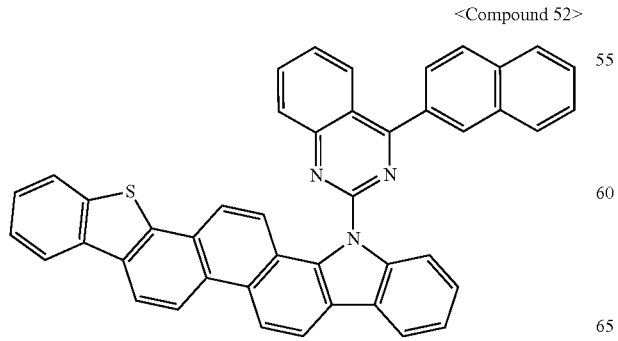
<Compound 56>

<Compound 57>
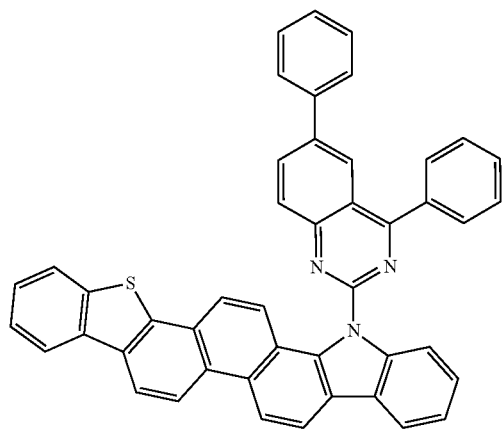
<Compound 58>
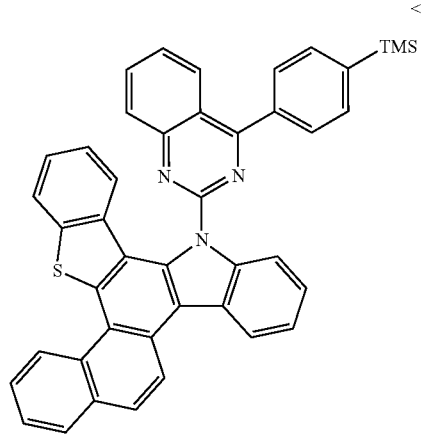
<Compound 59>
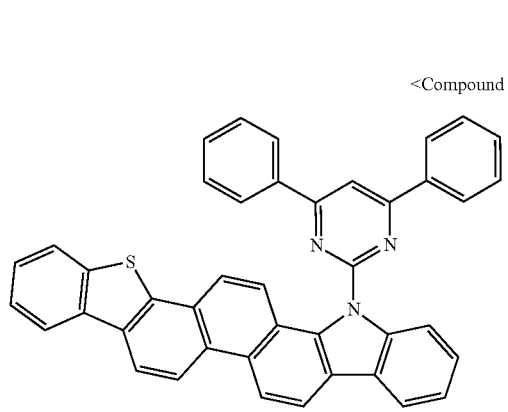
<Compound 60>
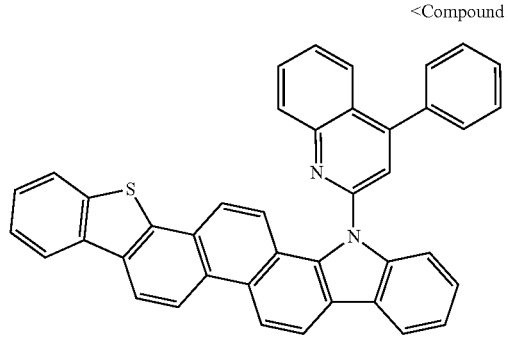
<Compound 61>
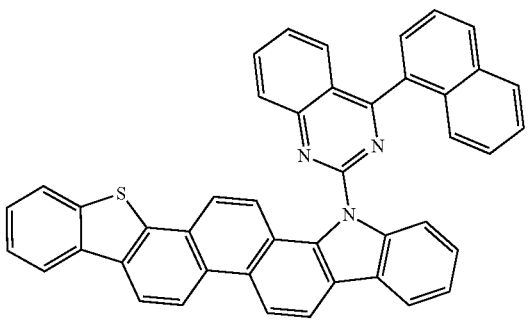
<Compound 62>
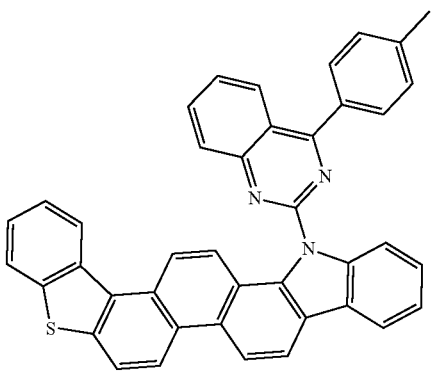
<Compound 63>
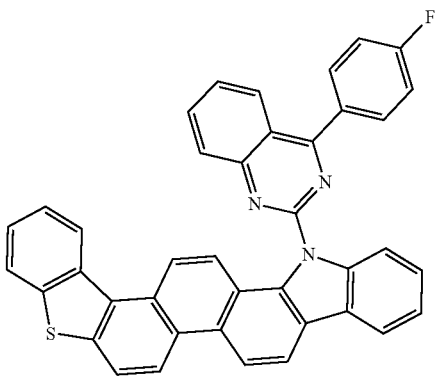
<Compound 64>
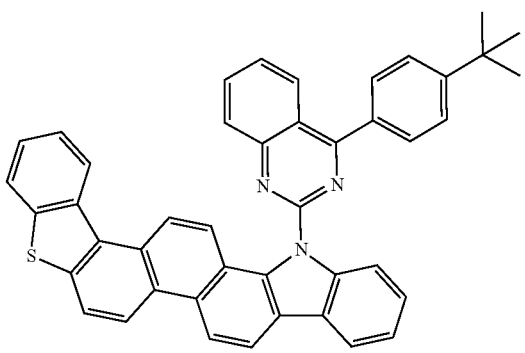

-continued
<Compound 65>
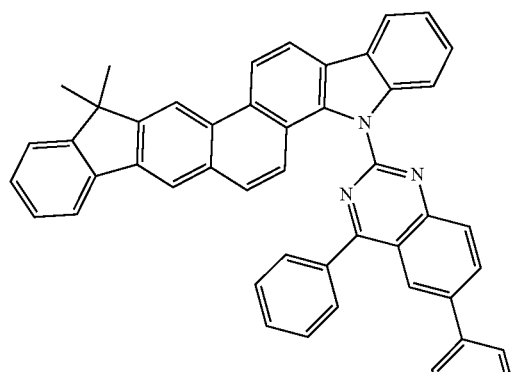
<Compound 66>
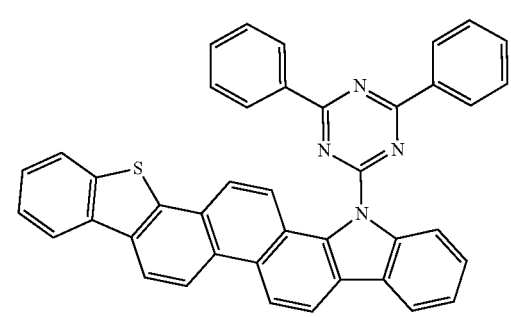
<Compound 67>
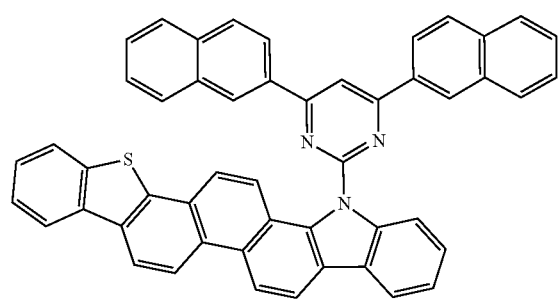
<Compound 68>
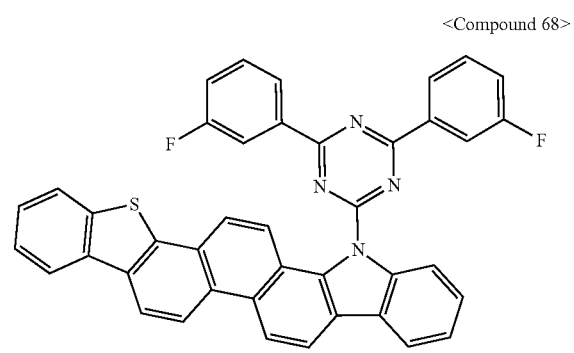
-continued
<Compound 69>
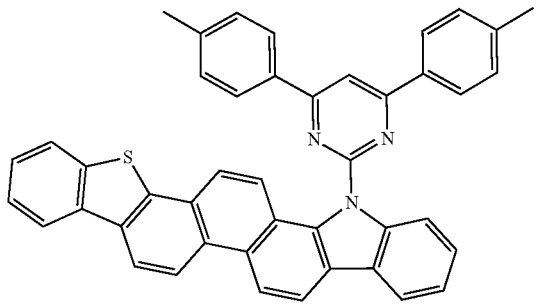
<Compound 70>
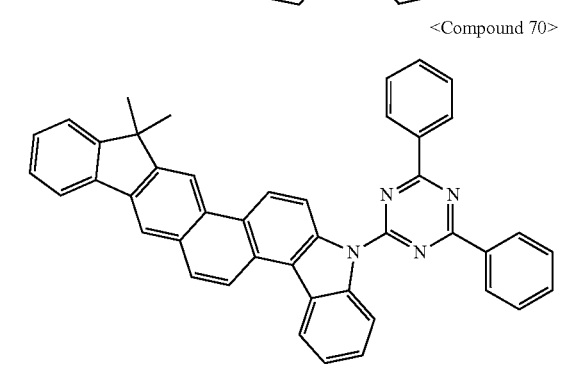
<Compound 71>
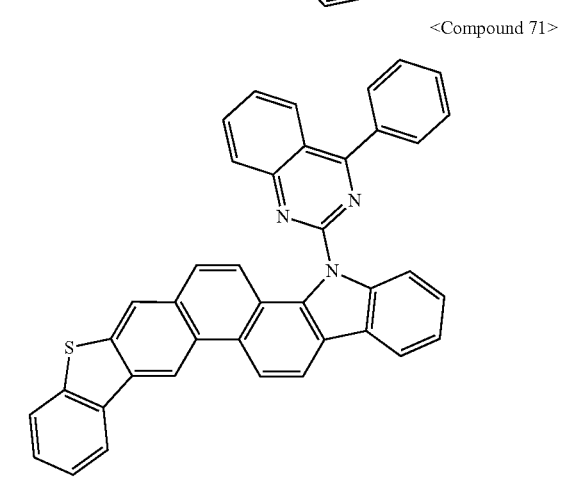
<Compound 72>
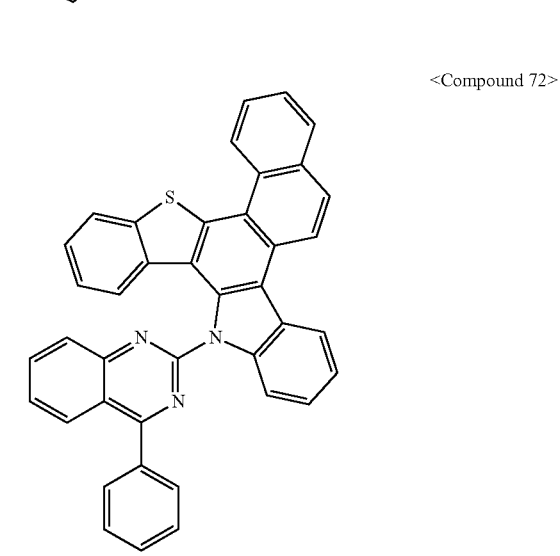

<Compound 73>
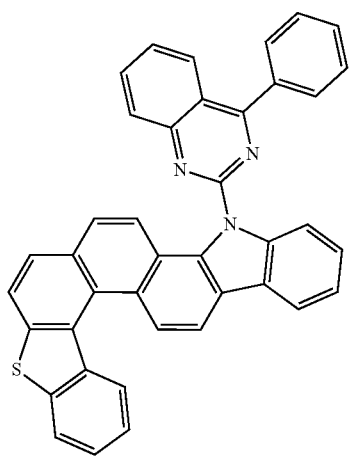
<Compound 74>
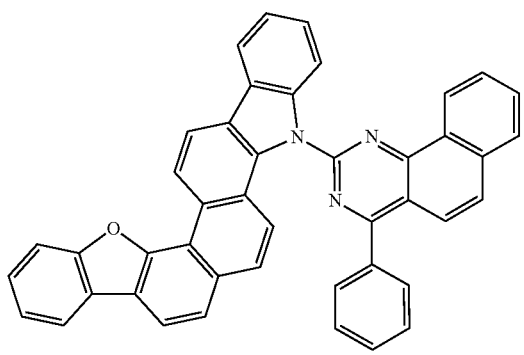
<Compound 75>
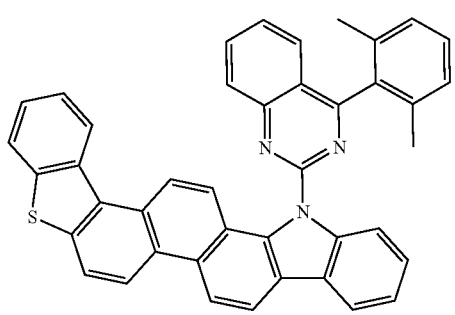
<Compound 76>
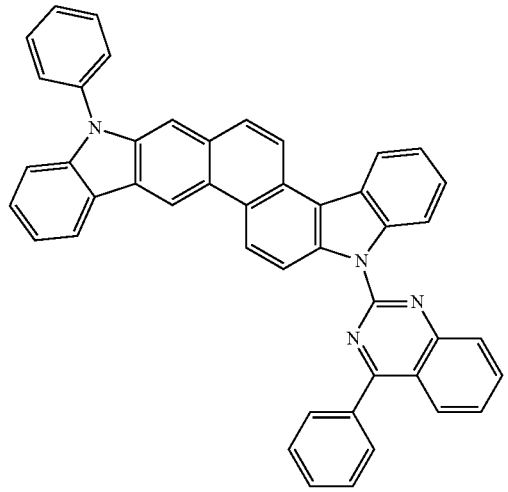
<Compound 77>
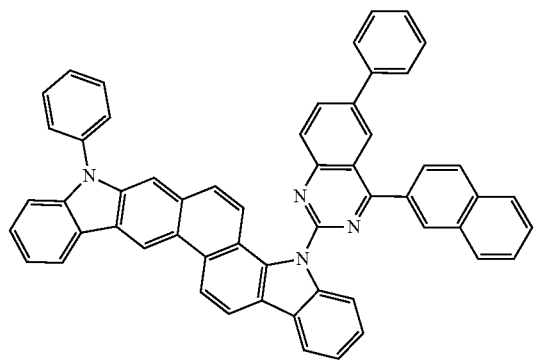
<Compound 78>
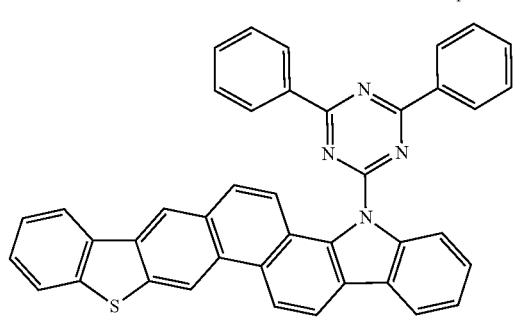
<Compound 79>
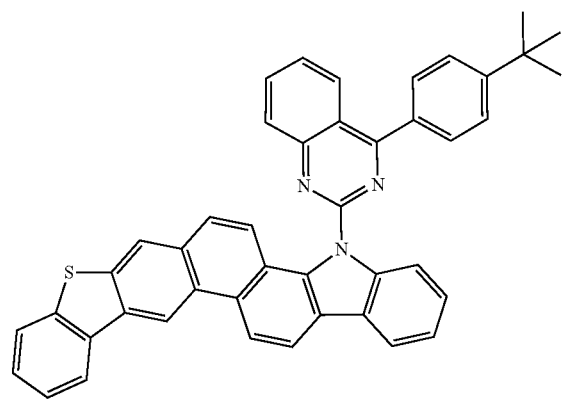

-continued
<Compound 80>
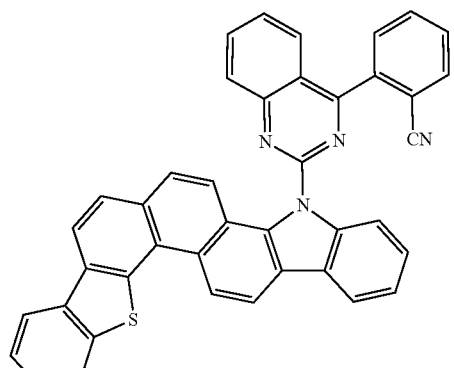
<Compound 81>
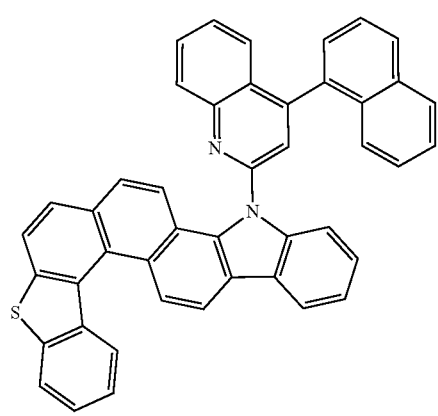
<Compound 82>
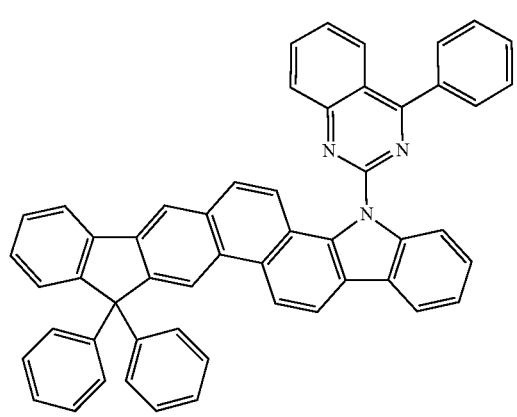
<Compound 83>
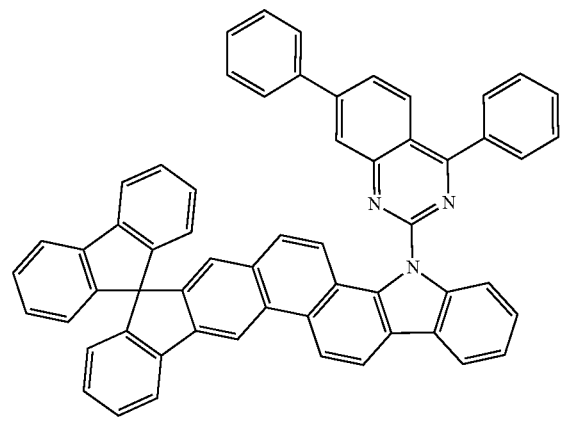
<Compound 84>
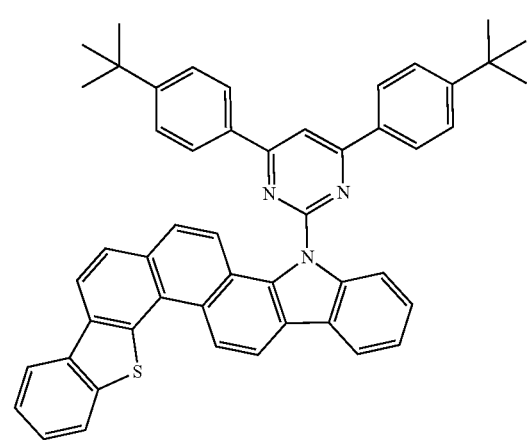
<Compound 85>
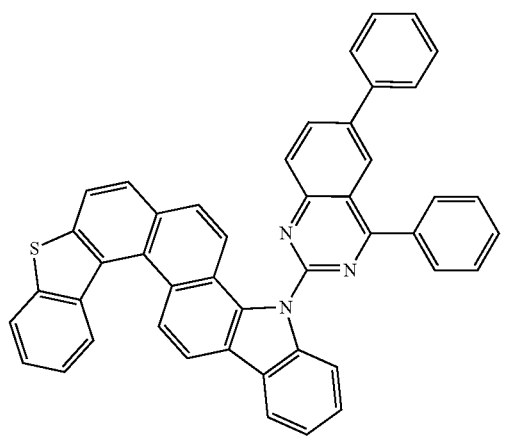

<Compound 86>
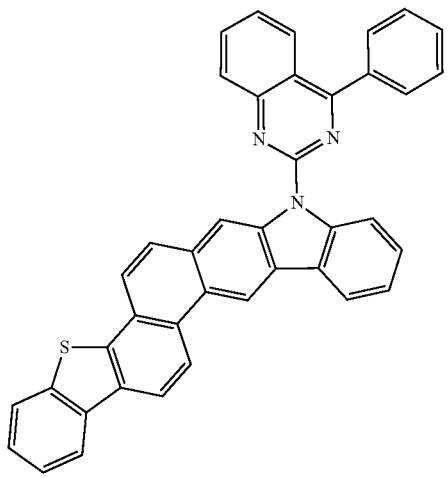
<Compound 87>
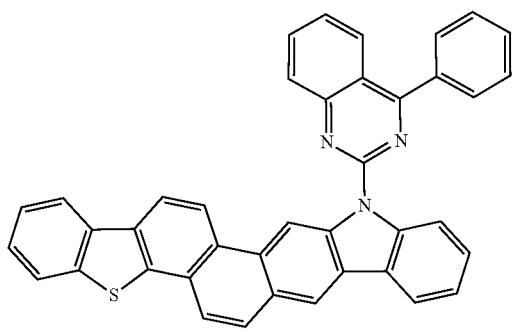
<Compound 88>
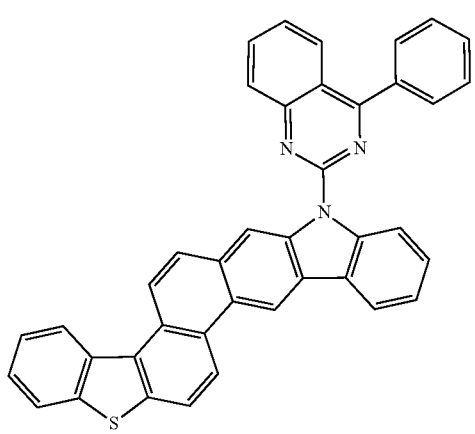
<Compound 89>
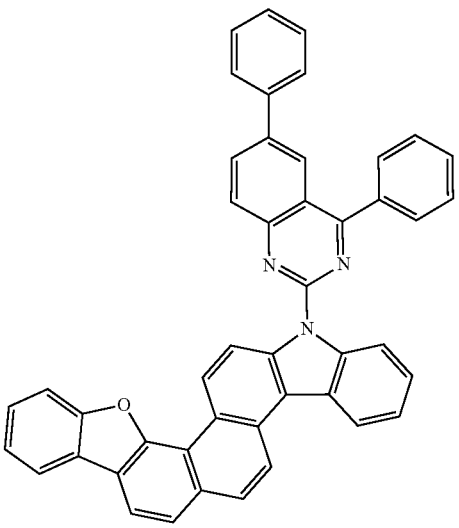
<Compound 90>
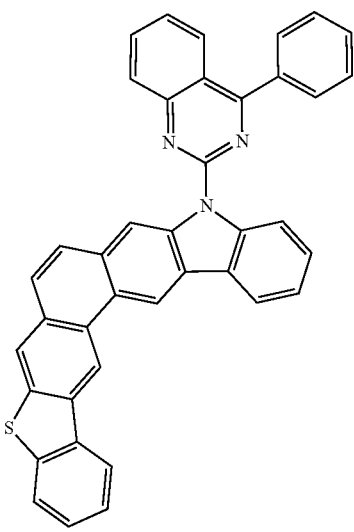
<Compound 91>
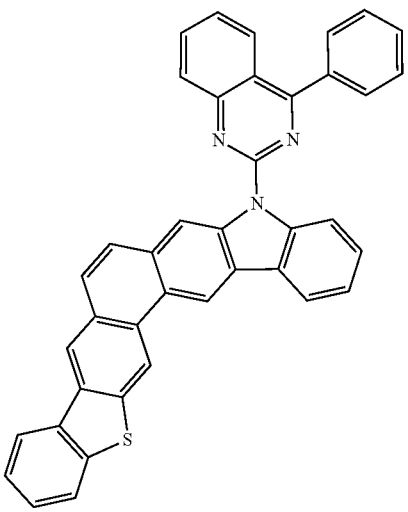

<Compound 92>
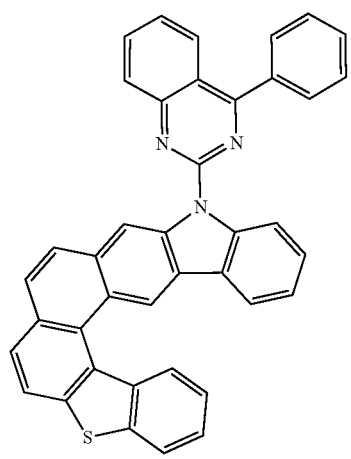
<Compound 93>
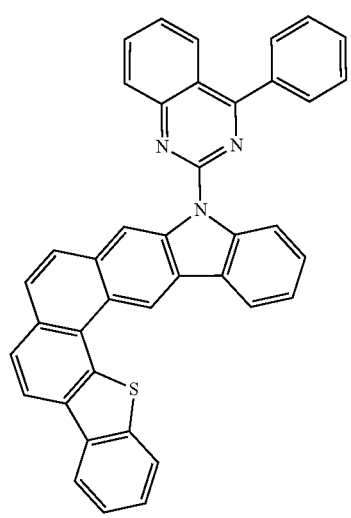
<Compound 94>
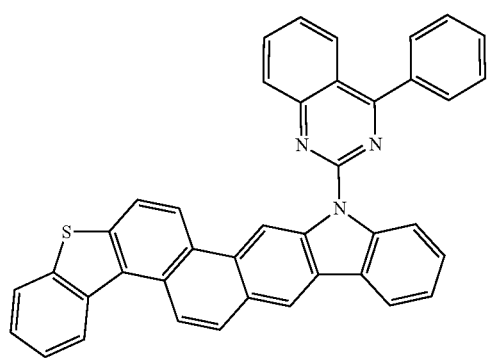
<Compound 95>
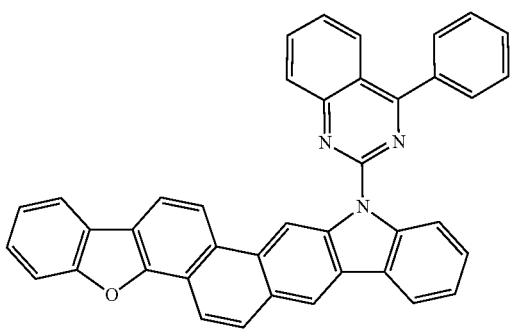
<Compound 96>
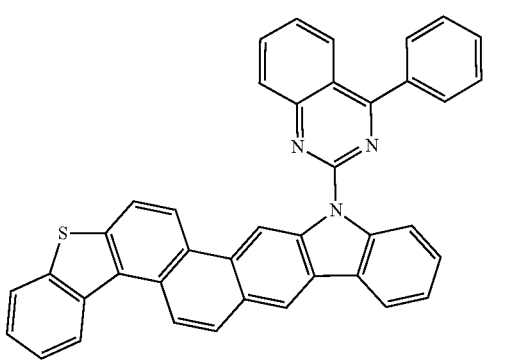
<Compound 97>
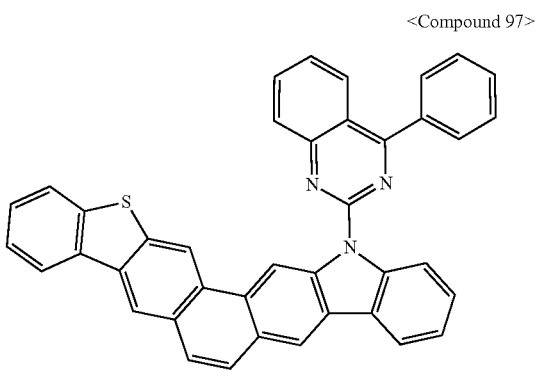
<Compound 98>
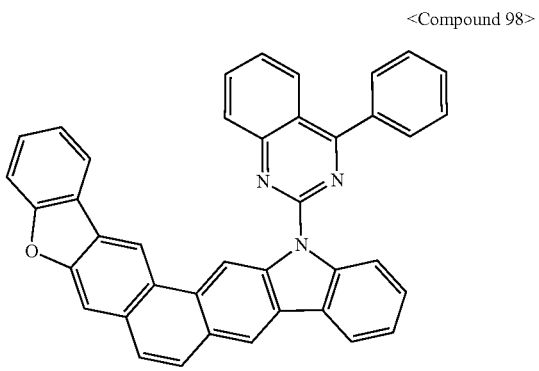

<Compound 99>
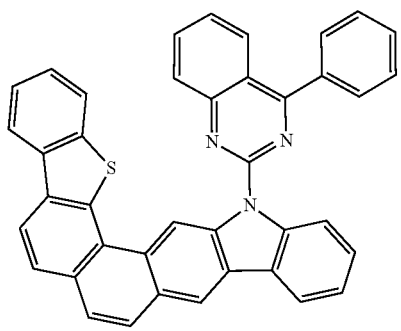
<Compound 100>
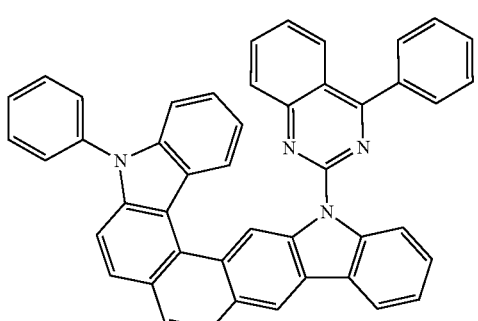
<Compound 101>
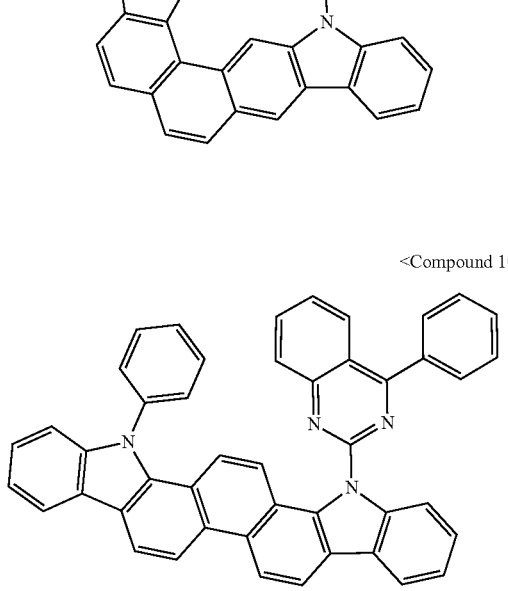
<Compound 102>
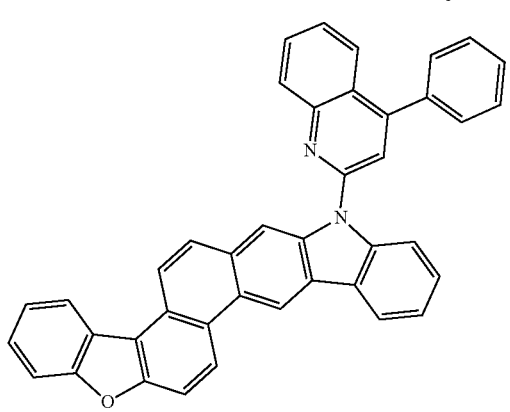
<Compound 103>
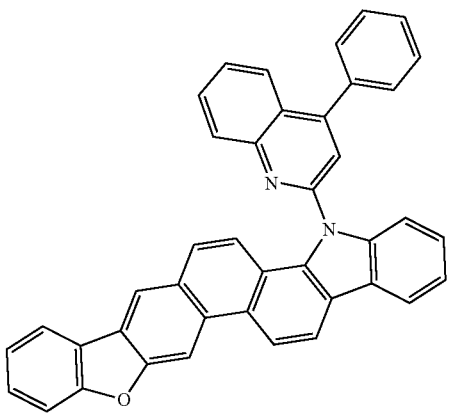
<Compound 104>
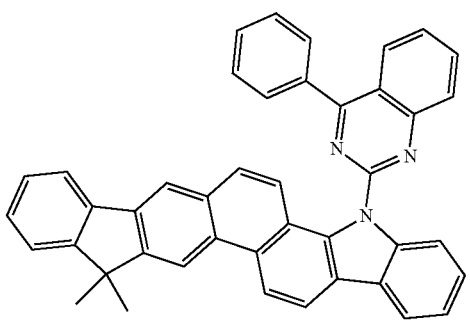
<Compound 105>
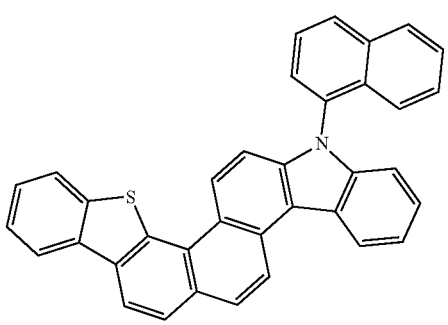
<Compound 106>
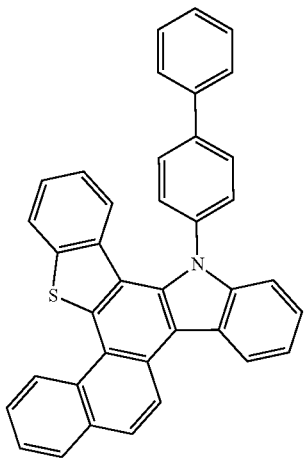

<Compound 107>
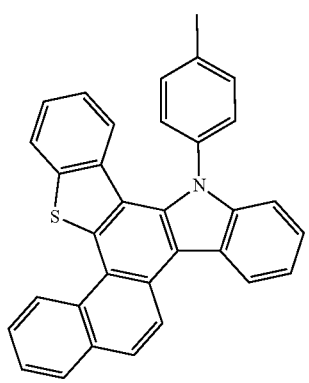
<Compound 111>
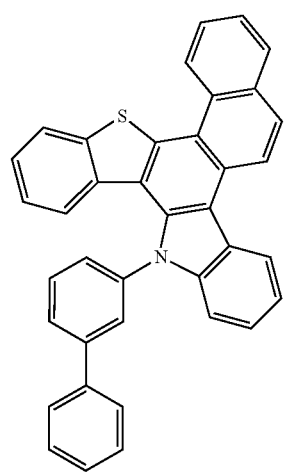
<Compound 108>
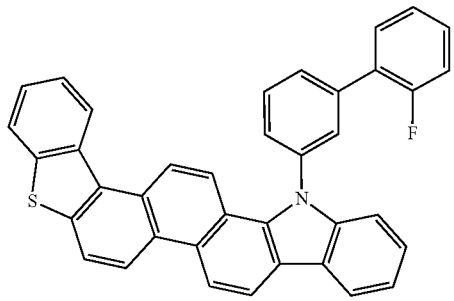
<Compound 112>
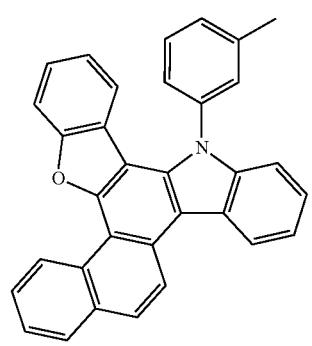
<Compound 109>
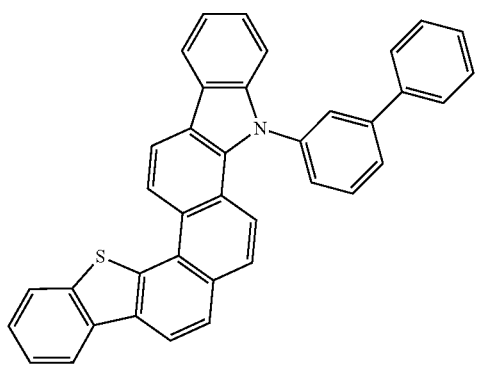
<Compound 113>
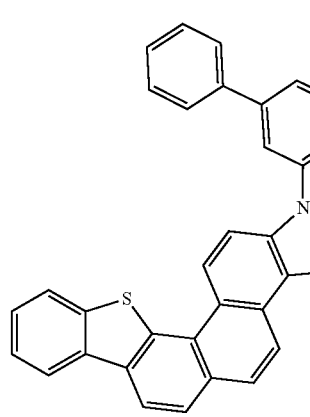
<Compound 110>
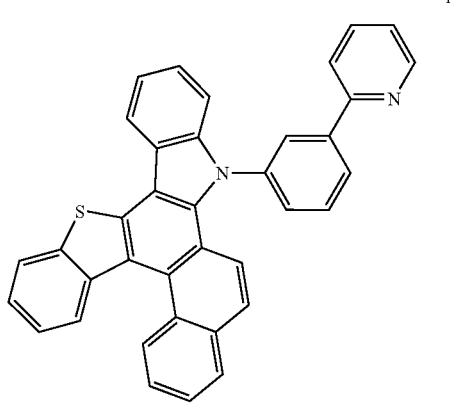
<Compound 114>
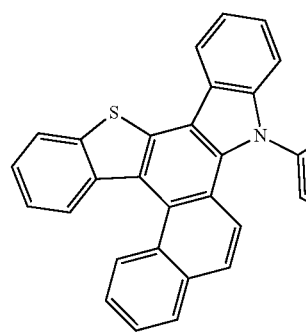

<Compound 115>
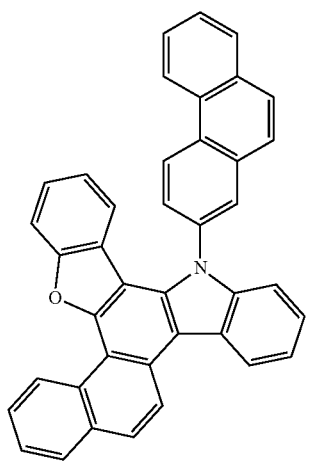
<Compound 116>
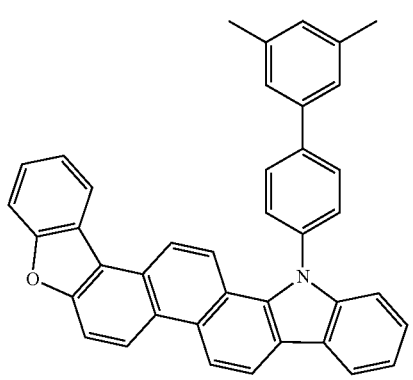
<Compound 117>
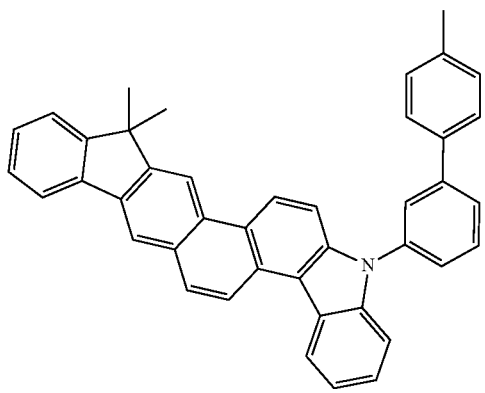
<Compound 118>
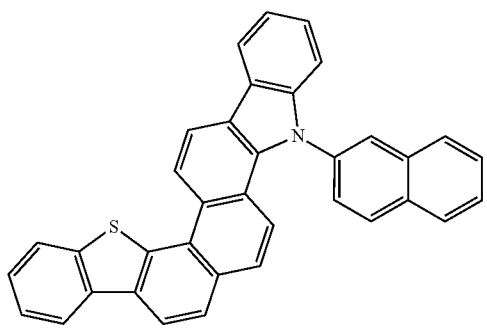
<Compound 119>
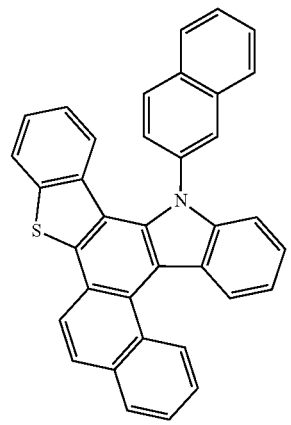
<Compound 120>
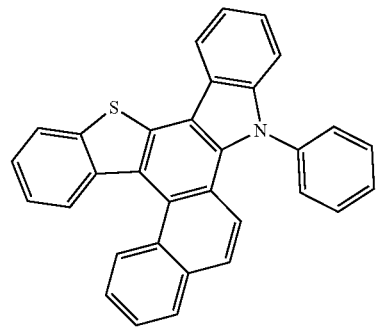
<Compound 121>
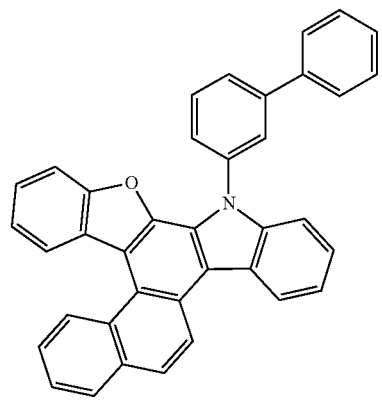
<Compound 122>
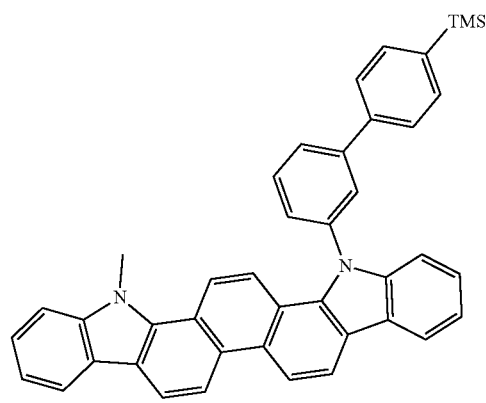

<Compound 123>
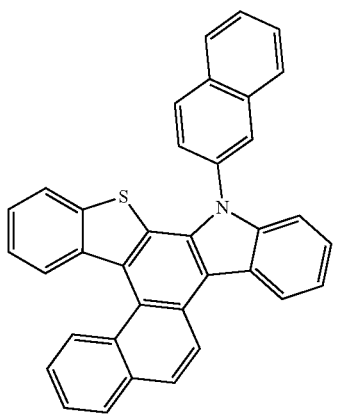

<Compound 124>

<Compound 125>

<Compound 126>
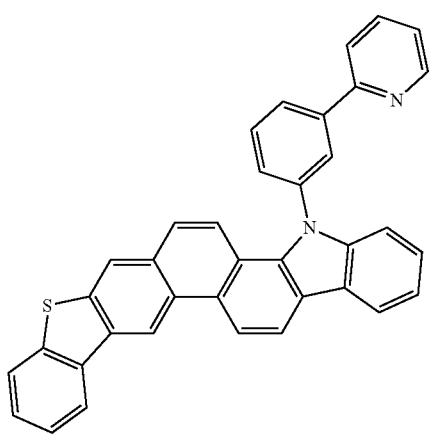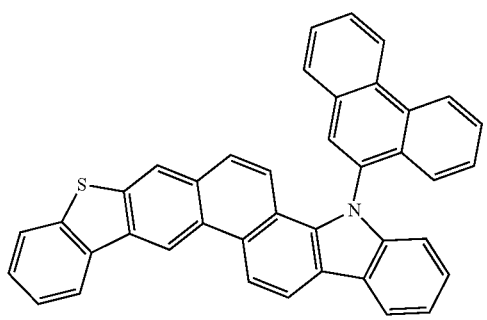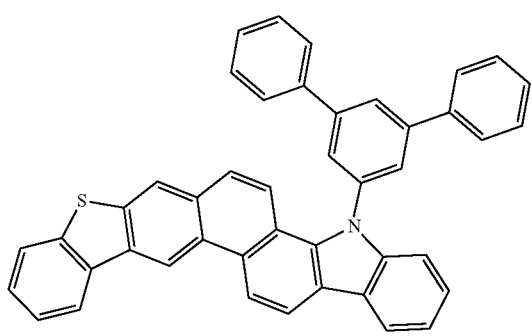

<Compound 127>

<Compound 128>

In accordance with another aspect thereof, the present invention addresses an organic light-emitting device, comprising a first electrode; a second electrode facing the first electrode; and an organic layer interposed between the first electrode and the second electrode, wherein the organic layer includes at least one of the organic compounds according to the present invention.

As used herein, the expression "(the organic layer) . . . includes at least one of the organic compounds" is construed to mean that the organic layer may include one or more organic metal compounds which are different and fall within the scope of the present invention.

The organic layer including the organic compound may include at least one of a hole injection layer, a hole transport layer, a functional layer capable of both hole injection and hole transport, a light-emitting layer, an electron transport layer, and an electron injection layer. In this regard, the organic layer interposed between the first electrode and the second electrode may include a light-emitting layer wherein the light emitting layer is composed of a host and a dopant and the organic light-emitting compound of the present invention may be used as a host.

Meanwhile, a dopant material may be used, along with a host, in the light-emitting layer in the present invention. When the light-emitting layer contains a host and a dopant, the content of the dopant in the light-emitting layer may range from about 0.01 to 20 parts by weight based on 100 parts by weight of the host, but is not limited thereto.

An electron transport material known in the art which functions to stably transport electrons introduced from an electron injection electrode (cathode) may be used in the electron transport in the present invention. Examples of the electron transport example include quinoline derivatives, particularly tris(8-quinolinolate)aluminum (Alq3), TAZ, BAlq, beryllium bis(benzoquinolin-10-oate: Bebq2), ADN, compound 201, compound 202, and the oxadiazole derivatives PBD, BMD, and BND, but are not limited thereto.

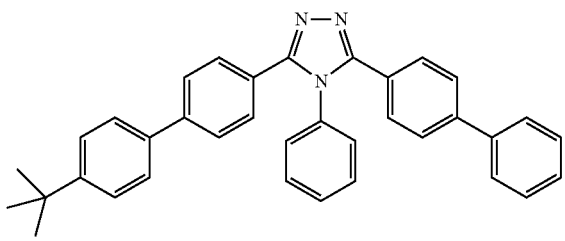

TAZ

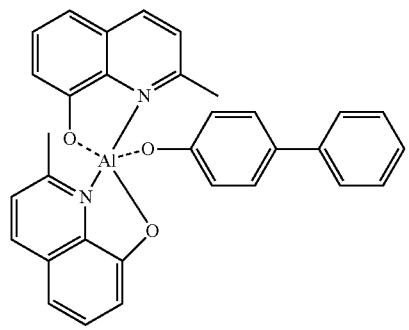

BAlq

<Compound 201>

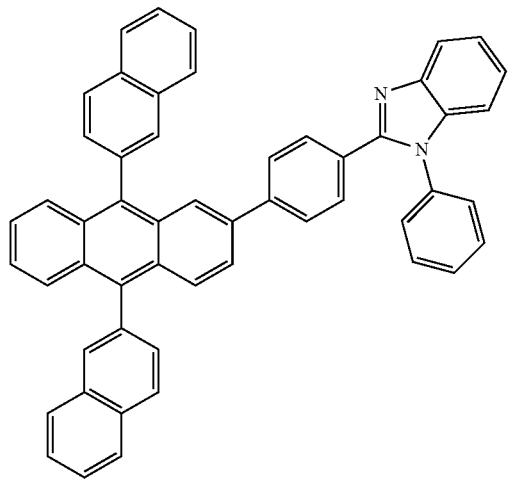

<Compound 202>

BCP

PBD

BMD

BND

In addition, the organic metal compound represented by Chemical Formula C may be used, either alone or in combination with the aforementioned material, as a compound for an electron transport layer in the present invention:

$Y_m$-M-$(OA)_n$     [Chemical Formula C]

wherein,

Y is a ligand that contains two moieties respectively responsible for forming a single bond through a direct bond to M and for forming a coordinate bond with M, each moiety being selected from among C, N, O and S, and which is chelated by the single bond and the coordinate bond;

M is an alkali metal, an alkaline earth metal, an aluminum (Al) atom, or a boron (B) atom, with the proviso that:

when M is an alkali metal, m=1 and n=0 when M is an alkaline earth metal, m=1 and n=1, or m=2 and n=0, or when M is aluminum or boron, m is an integer of 1 to 3 and n is an integer of 0 to 2, satisfying the relationship m+n=3; and OA is a monodentate ligand capable of forming a single bond or a coordinate bond with M, wherein O is oxygen, and A is selected from among a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, and a substituted or unsubstituted heteroaryl of 2 to 50 carbon atoms bearing O, N, or S as a heteroatom; and wherein the term 'substituted' in the expression "substituted or unsubstituted" means having at least one substituent selected from the group consisting of deuterium, a cyano, a halogen, a hydroxy, a nitro, an alkyl, an alkoxy, an alkylamino, an arylamino, a heteroarylamino, an alkylsilyl, an arylsilyl, an aryloxy, an aryl, a heteroaryl, a germanium, a phosphorus, and a boron.

In Chemical Formula C, Y's, which may be the same or different, may each be independently any one selected from among, but not limited to, the following Structural Formulas C1 to C39:

[Structural Formula C1]

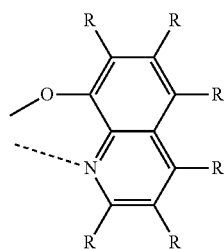

[Structural Formula C2]

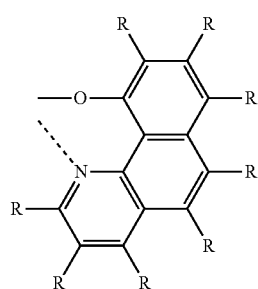

[Structural Formula C3]

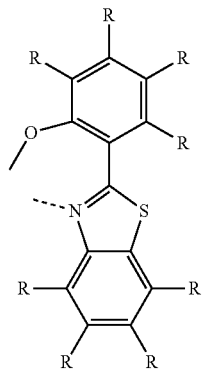

[Structural Formula C4]

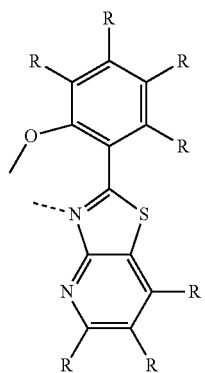

[Structural Formula C5]

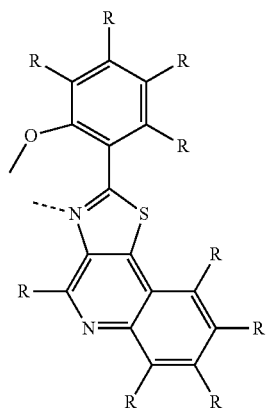

[Structural Formula C6]

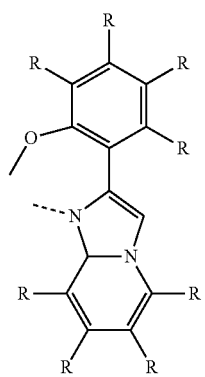

[Structural Formula C7]
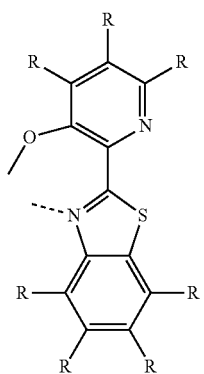
[Structural Formula C8]
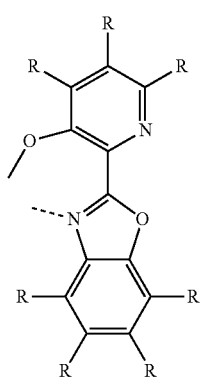
[Structural Formula C9]
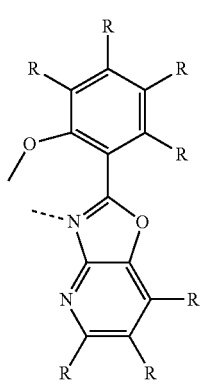
[Structural Formula C10]
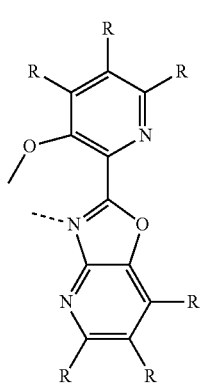
[Structural Formula C11]
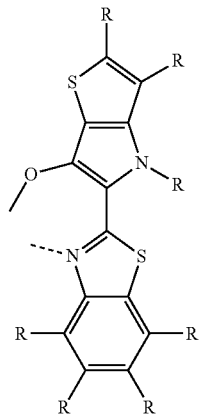
[Structural Formula C12]
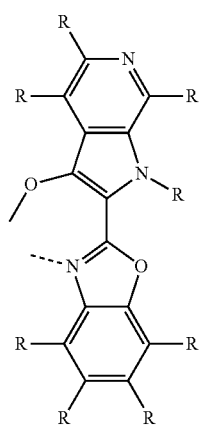
Structrual Formula C13]
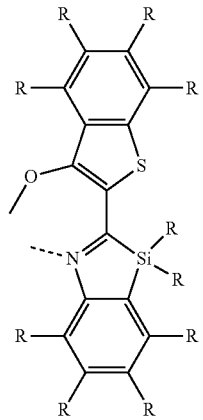
[Structural Formula C14]
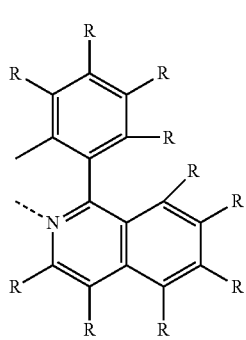

[Structural Formula C15]
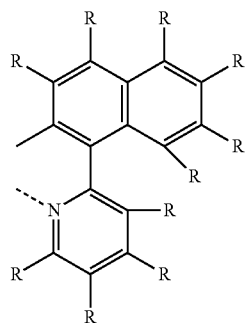
[Structural Formula C16]
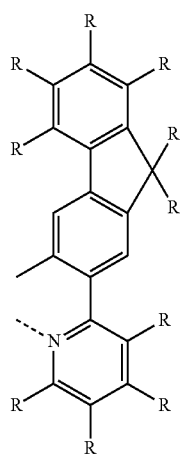
[Structural Formula C17]
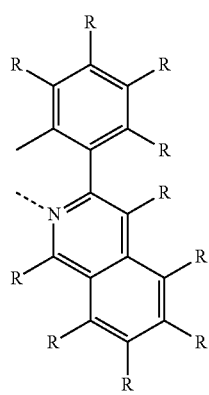
[Structural Formula C18]
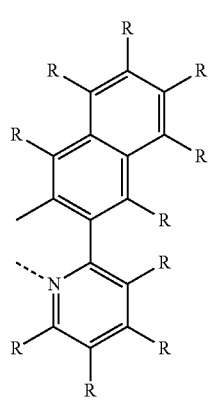
[Structural Formula C19]
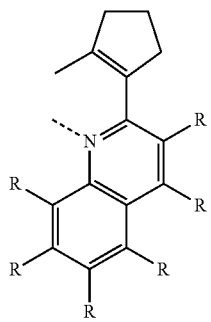
[Structural Formula C20]
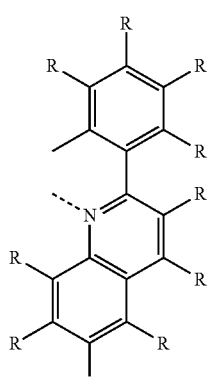
[Structural Formula C21]
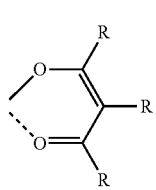
[Structural Formula C22]
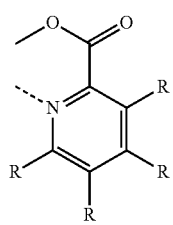
[Structural Formula C23]
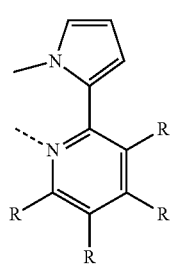
[Structural Formula C24]
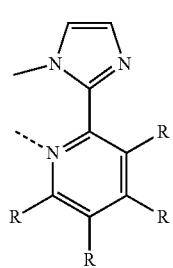

[Structural Formula C25]
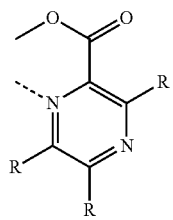
[Structural Formula C26]
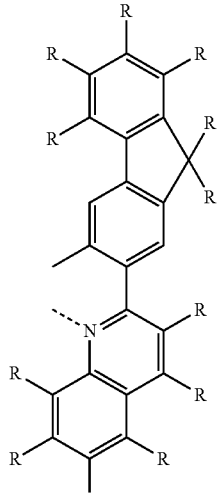
[Structural Formula C27]
[Structural Formula C28]
[Structural Formula C29]
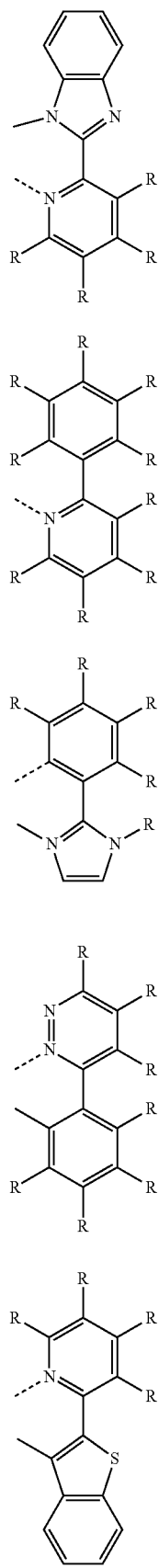
[Structural Formula C30]
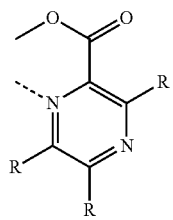
[Structural Formula C31]
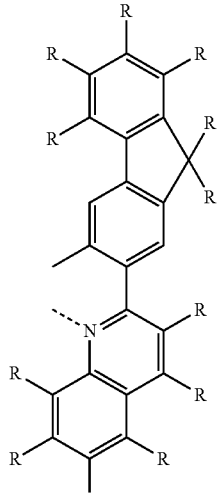
[Structural Formula C32]
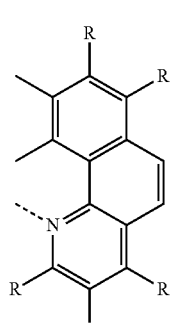
[Structural Formula C33]
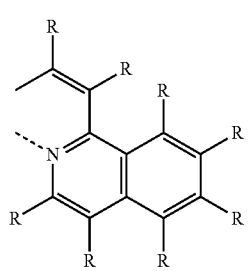
[Structural Formula C34]
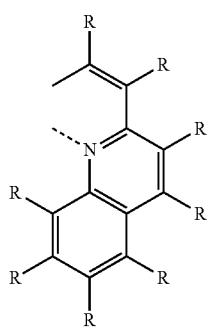

-continued

[Structural Formula C35]
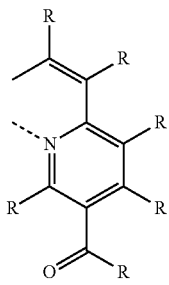

[Structral Formula C36]
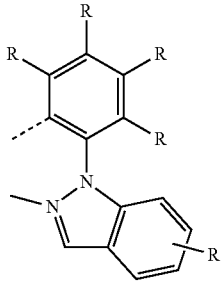

[Structural Formula C37]
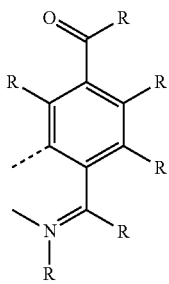

[Structural Formula C38]
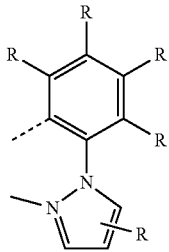

[Structural Formula C39]
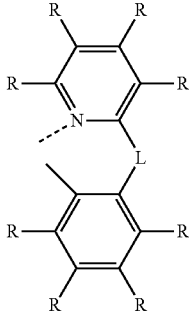

wherein,
R's, which may be the same or different, are each independently selected from among a hydrogen, a deuterium, a halogen, a cyano, a substituted or unsubstituted alkyl of 1 to 30 carbon atoms, a substituted or unsubstituted aryl of 6 to 30 carbon atoms, a substituted or unsubstituted heteroaryl of 3 to 30 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 30 carbon atoms, and a substituted or unsubstituted arylsilyl of 6 to 30 carbon atoms, and may each be connected to an adjacent one via alkylene or alkenylene to form a spiro ring or fused ring.

Below, the organic light-emitting device of the present invention is explained with reference to FIG. 1.

FIG. 1 is a schematic cross-sectional view of the structure of an organic light-emitting device according to some embodiments of the present invention. The organic light-emitting device includes an anode 20, a hole transport layer 40, an organic light-emitting layer 50, an electron transport layer 60, and a cathode 80, and optionally a hole injection layer 30 or an electron injection layer 70. In addition, one or two Intermediate layers may be further formed in the organic light-emitting device. A hole barrier layer or an electron barrier layer may be also further established.

Reference is made to FIG. 1 with regard to the organic light-emitting device of the present invention and the fabrication thereof. First, a substrate 10 is coated with an anode electrode material to form an anode 20 thereon. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO), which are transparent and superior in terms of conductivity, may be used.

A hole injection layer material is applied to the top of the anode electrode 20 by thermal deposition in a vacuum or by spin coating to form a hole injection layer 30. Subsequently, using thermal deposition in a vacuum or spin coating, a hole transport layer material is applied to the hole injection layer 30 to form a hole transport layer 40.

So long as it is typically used in the art, any hole injection layer material may be used in the present invention, without particular limitations. Examples include 2-TNATA [4,4',4"-tris(2-naphthylphenyl-phenylamino) -triphenylamine], NPD [N,N'-di(1-naphthyl)-N,N'-diphenylbenzidine)], TPD[N,N'-diphenyl-N,N'-bis(3-methylphenyl)-1,1'-biphenyl-4,4'-diamine], DNTPD[N,N'-diphenyl-N,N'-bis-[4-(phenyl-m-tolyl-amino) -phenyl]-biphenyl-4,4'-dia mine], and the like, but are not limited thereto.

Further, any material that is typically known in the art may be used for the hole transport layer without particular limitations. Examples include N,N'-bis(3-methylphenyl)-N, N'-diphenyl-[1,1-biphenyl]-4,4'-diamine (TPD) and N,N'-di (naphthalen-1-yl)-N,N'-diphenylbenzidine (a-NPD), but are not limited thereto.

Then, an organic light-emitting layer 50 is deposited on the hole transport layer 40, optionally followed by the formation of a hole barrier layer (not shown) on the organic light-emitting layer 50 by deposition in a vacuum or by spin coating. When holes traverse the organic light-emitting layer and are introduced into the cathode, the efficiency and lifespan of the device are deteriorated. Formed of a material with a low HOMO (Highest Occupied Molecular Orbital) level, the hole barrier layer serves to prevent the introduction of holes into the cathode. Any material that has a higher ionization potential than the light-emitting compound and which is also able to carry electrons may be used for the hole barrier layer without limitations. Representative among hole barrier materials are BAlq, BCP, and TPBI.

For use in the hole barrier layer, selection may be made of BAlq, BCP, Bphen, TPBI, NTAZ, BeBq2, OXD-7, Liq, and any compound of Chemical Formulas 1001 to 1007, but is not limited thereto.
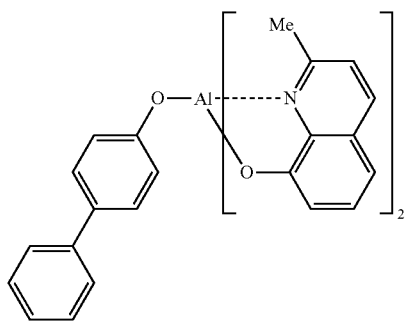
BAlq
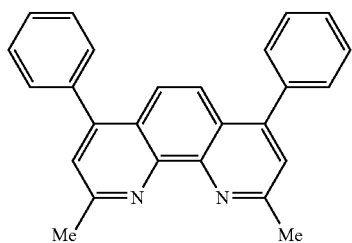
BCP
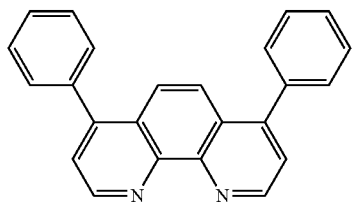
Bphen
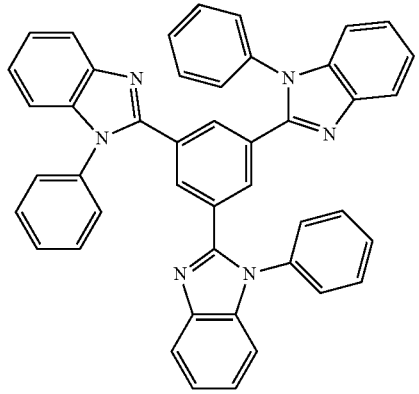
TPBI
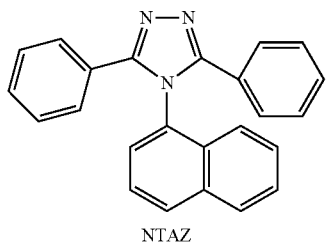
NTAZ
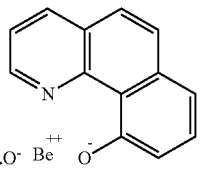
BeBq2
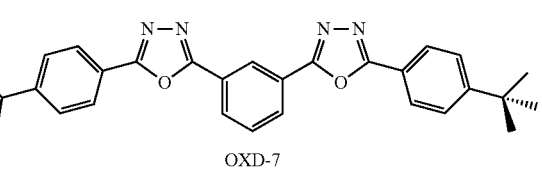
OXD-7
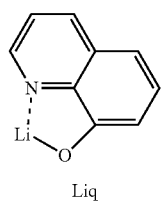
Liq
Chemical Formula 1001
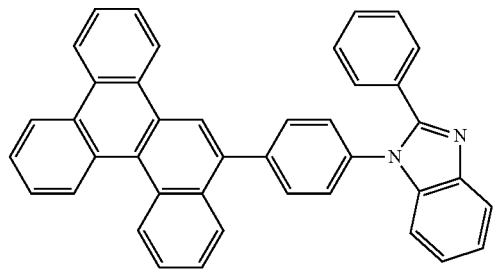
Chemcial Formula 1002
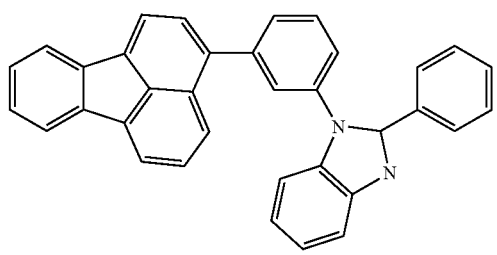

Chemical Formula 1003

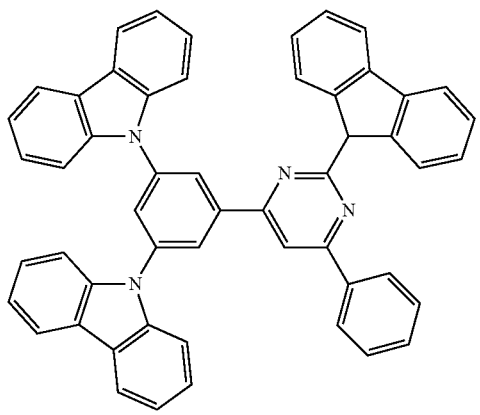

Chemical Formula 1004

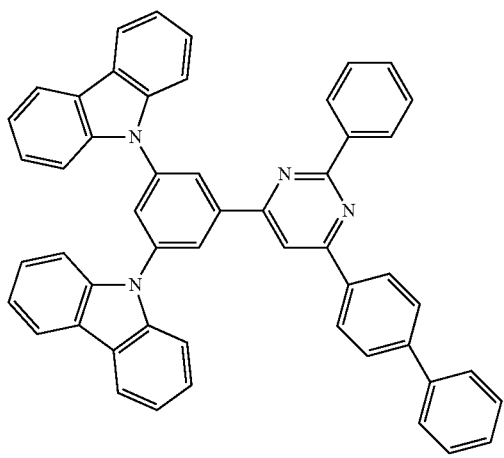

Chemical Formula 1005

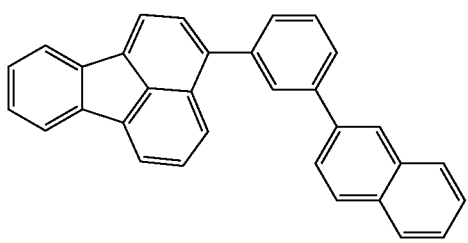

Chemical Formula 1006

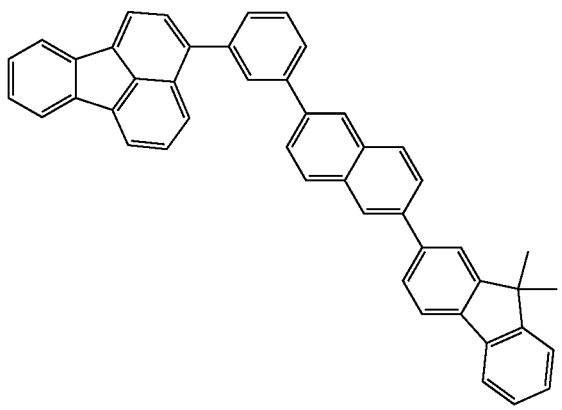

Chemical Formula 1007

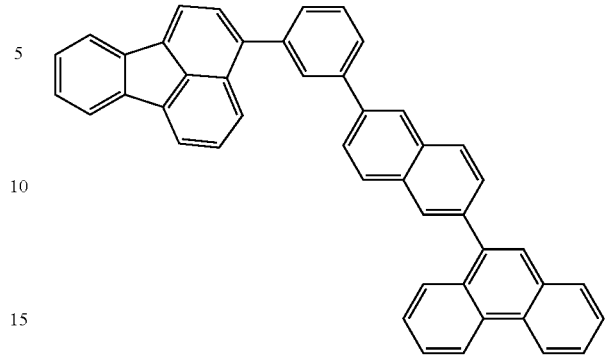

Using a vacuum deposition method or a spin-coating method, an electron transport layer 60 may be deposited on the hole barrier layer and may then be overlaid with an electron injection layer 70. A cathode metal is deposited on the electron injection layer 70 by thermal deposition in a vacuum to form a cathode 80, thus obtaining an organic EL device. Here, the cathode may be made of lithium (Li), magnesium (Mg), aluminum (Al), aluminum-lithium (Al—Li), calcium (Ca), magnesium-indium (Mg—In), or magnesium-silver (Mg—Ag). For a top-emitting device, a transparent cathode made of ITO or IZO may be employed.

The light-emitting layer may include a host and a dopant.

According to an embodiment of the present invention, the light-emitting layer preferably ranges in thickness from 50 to 2,000 Å.

The dopant used in the light-emitting layer may be at least one selected from among the compounds represented by the following General Formula A-1:

$ML_1L_2L_3$ [General Formula A-1]

wherein M is selected from metals in Groups 7, 8, 9, 10, 11, 12, 13, 14, 15, and 16, and preferably from among Ir, Pt, Pd, Rh, Re, Os, Tl, Pb, Bi, In, Sn, Sb, Te, Au, and Ag, and $L_1$, $L_2$, and $L_3$ are each ligands which may be the same or different and are each independently selected from among, but not limited to, compounds represented by the following Structural Formula D.

In the following Structural Formula D, '*' represents a coordination site on metal ion M.

[Structural Formula D]

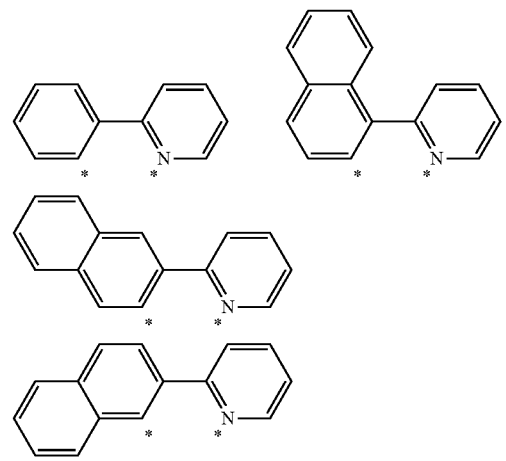

-continued
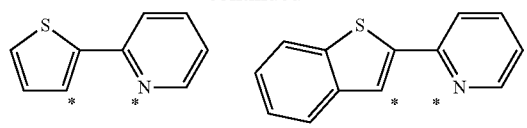
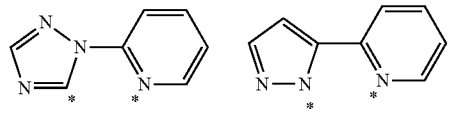
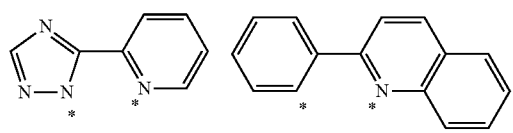
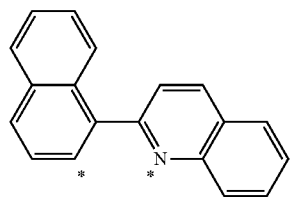
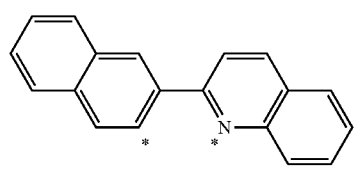
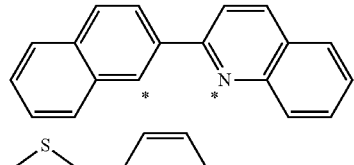
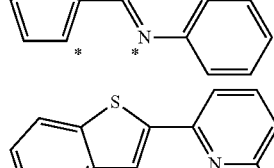
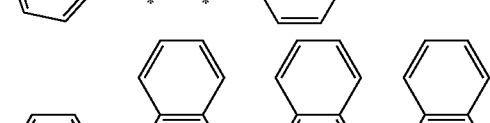
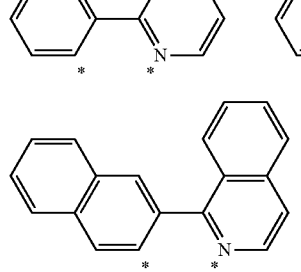
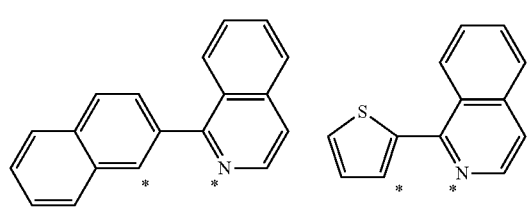
-continued
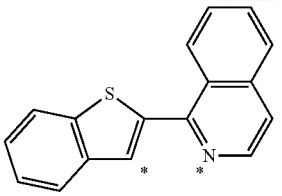
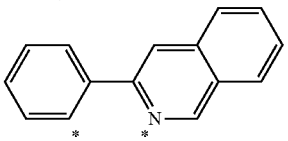
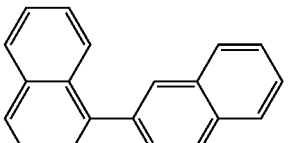
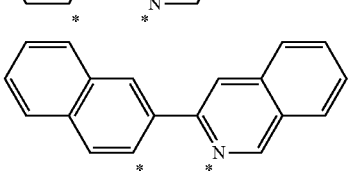
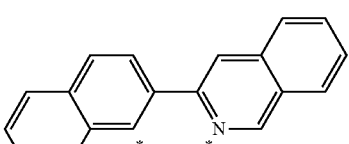
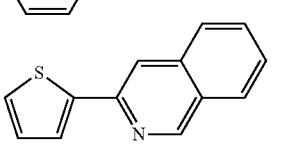
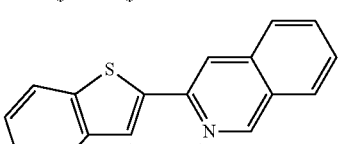
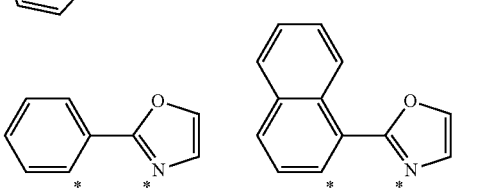
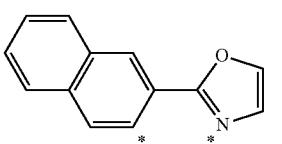
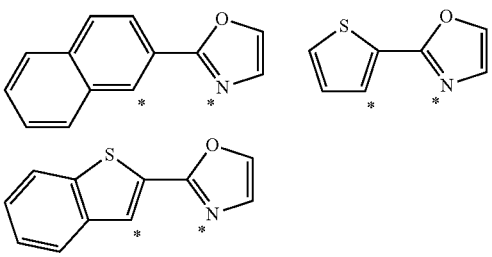

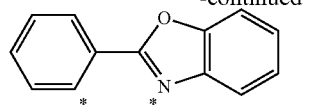
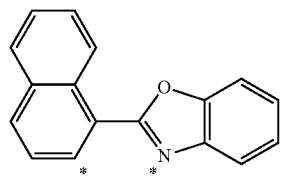
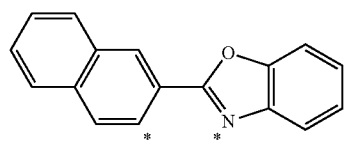
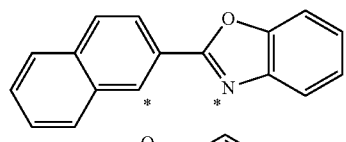
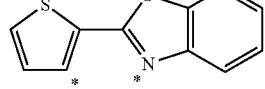
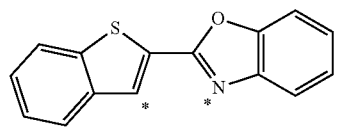
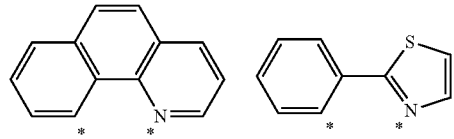
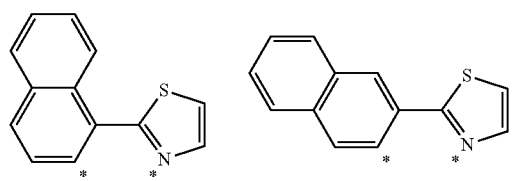
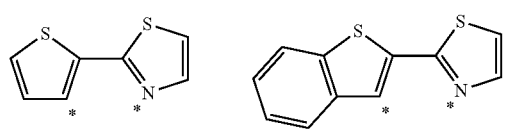
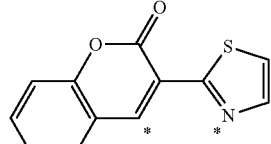
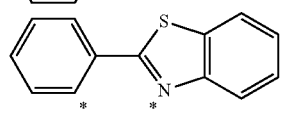
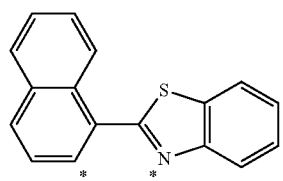
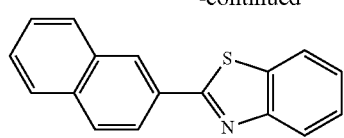
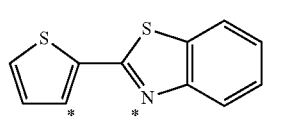
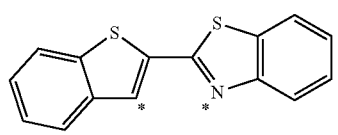
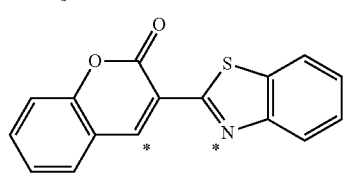
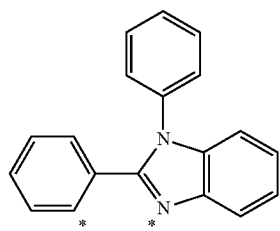
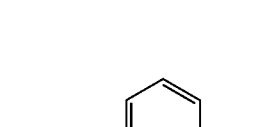
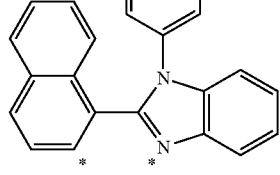
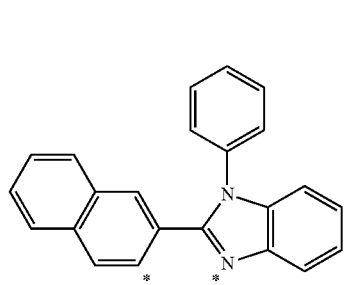
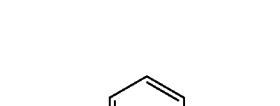
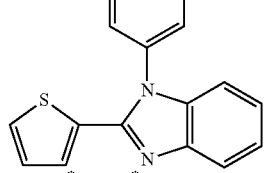

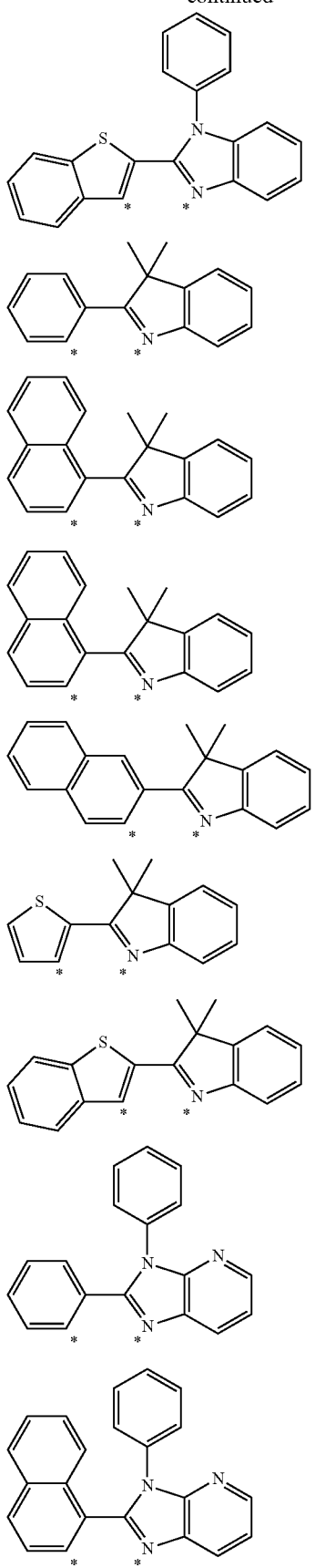
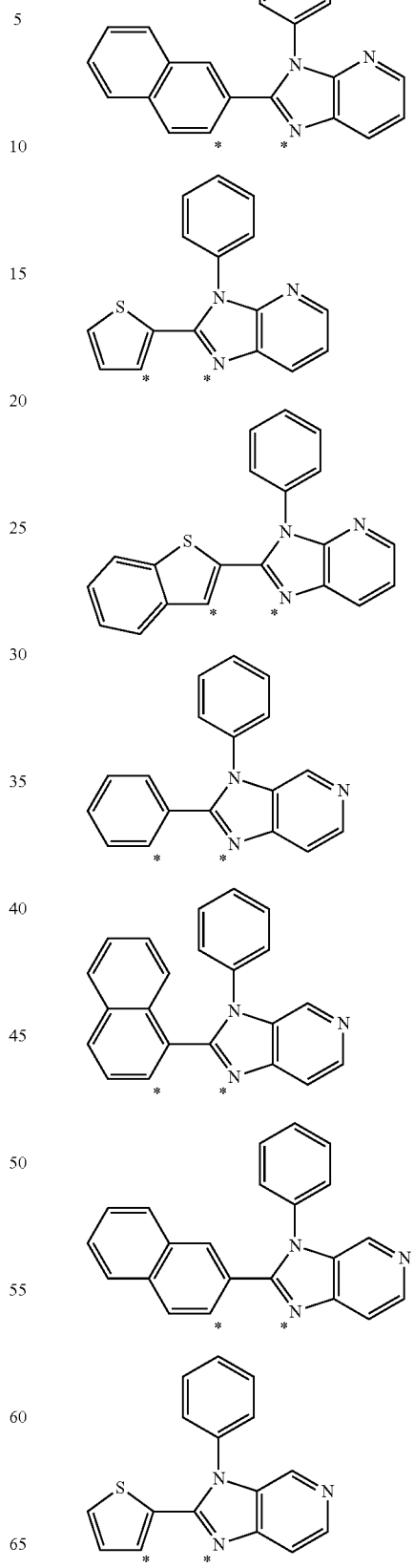

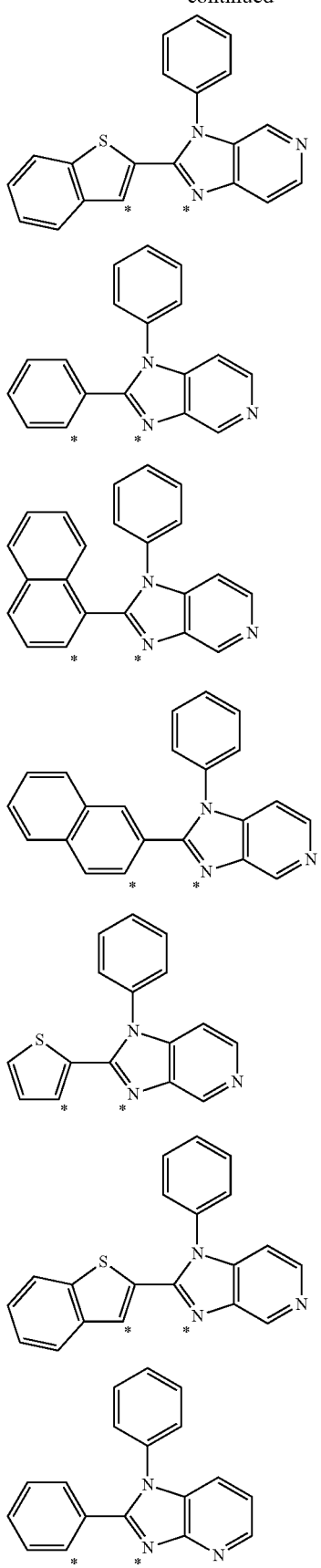
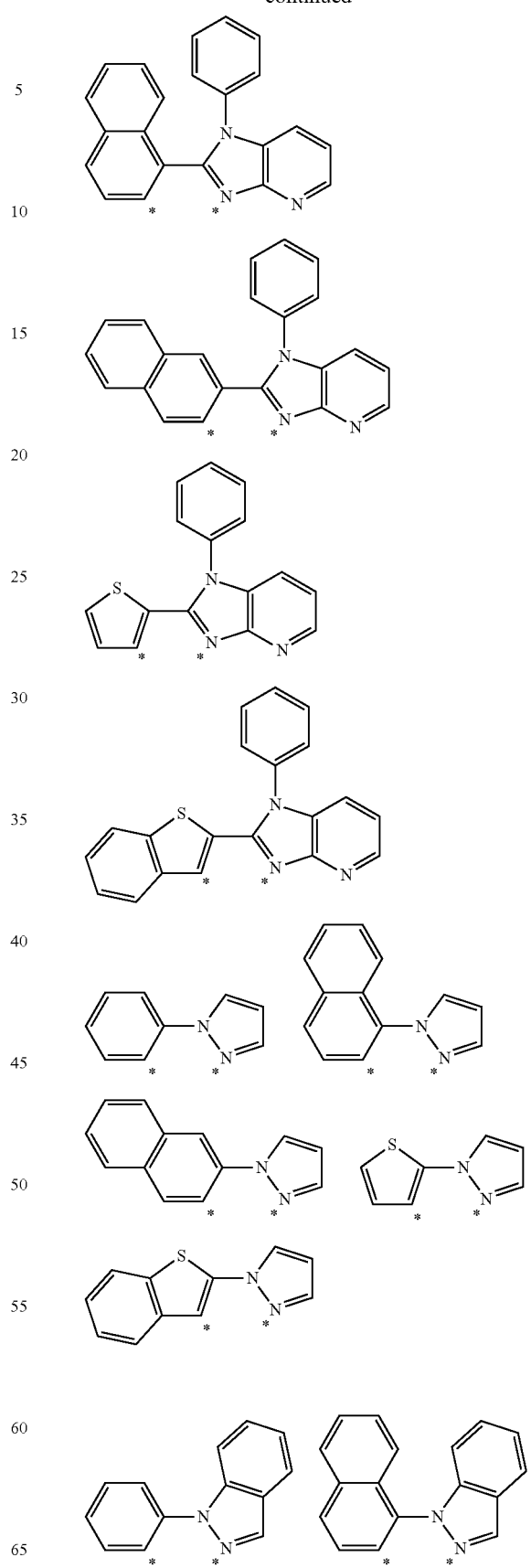

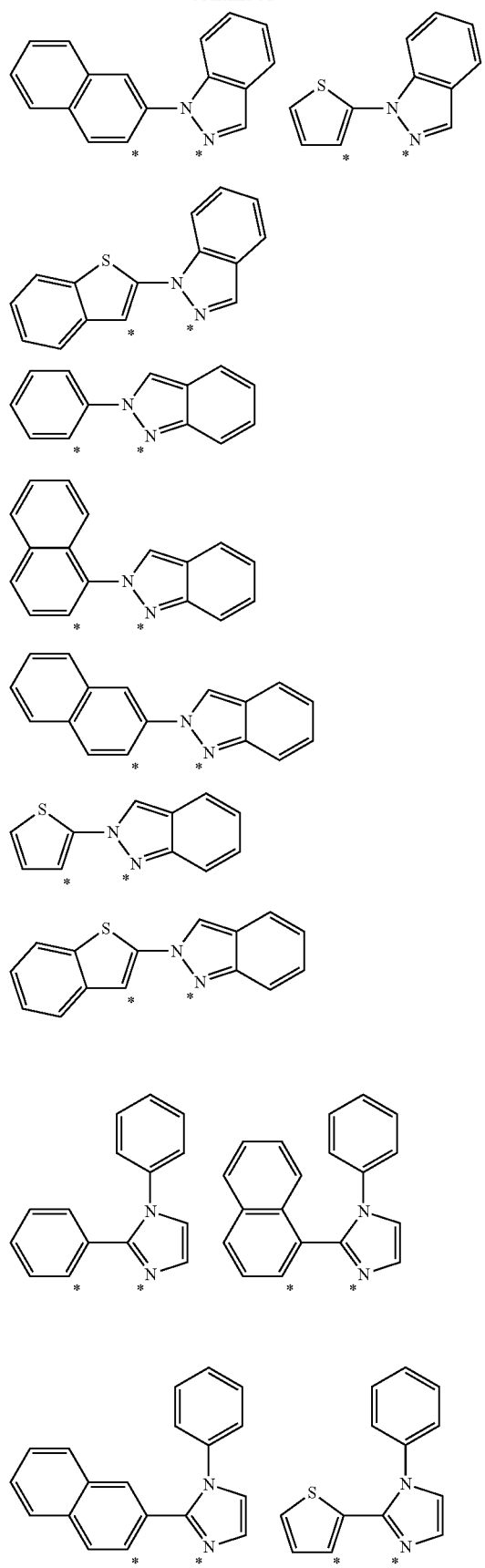
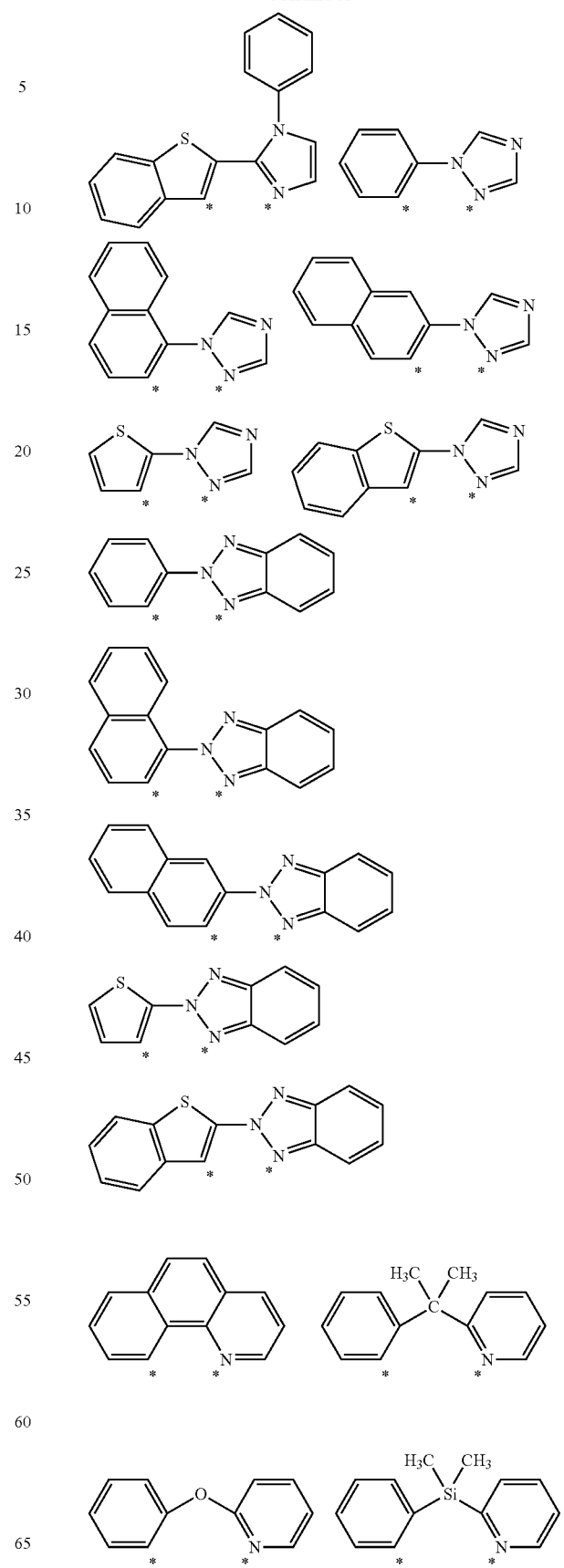

73
-continued
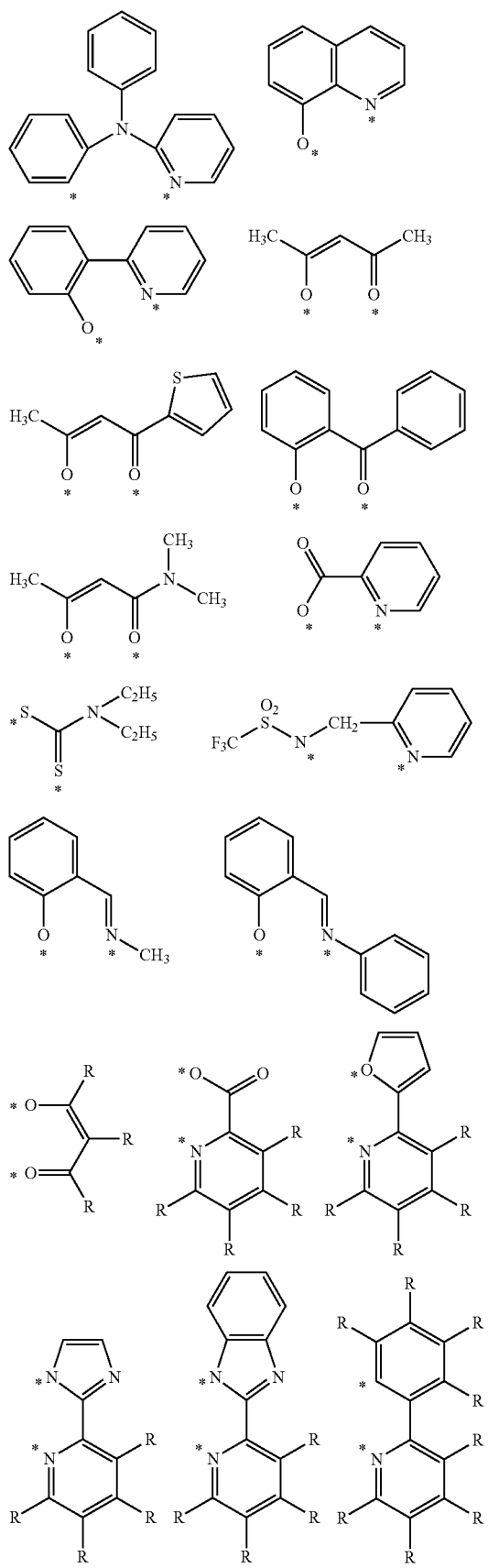
74
-continued
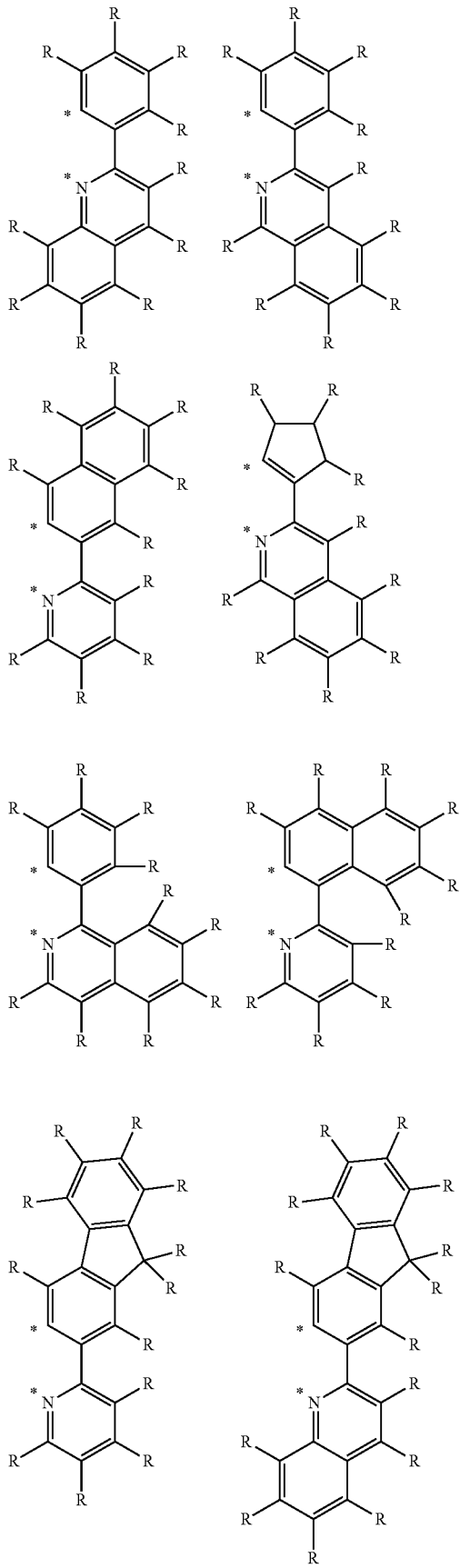

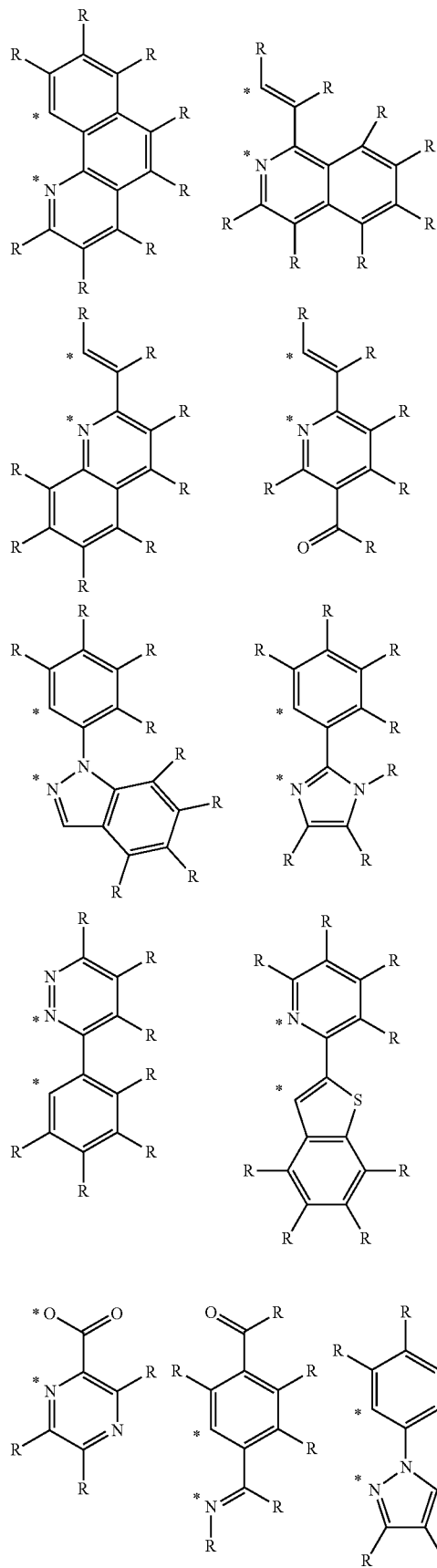

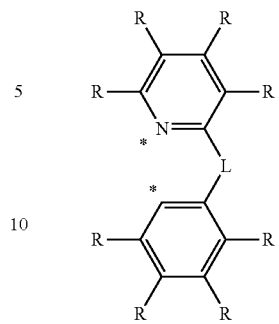

wherein R's, which may the same or different, are each independently any one selected from among a hydrogen, a deuterium, a halogen, a cyano, a substituted or unsubstituted alkyl of 1 to 30 carbon atoms, a substituted or unsubstituted aryl of 6 to 50 carbon atoms, a substituted or unsubstituted heteroaryl of 5 to 50 carbon atoms, a substituted or unsubstituted alkoxy of 1 to 30 carbon atoms, a substituted or unsubstituted cycloalkyl of 3 to 30 carbon atoms, a substituted or unsubstituted alkenyl of 2 to 30 carbon atoms, a substituted or unsubstituted alkylamino of 1 to 30 carbon atoms, a substituted or unsubstituted alkylsilyl of 1 to 30 carbon atoms, a substituted or unsubstituted arylamino of 6 to 30 carbon atoms, and a substituted or unsubstituted arylsilyl of 6 to 30 carbon atoms, with a proviso that:

R's may each be further substituted independently with at least one substituent selected from among an alkyl of 1 to 20 carbon atoms, a cycloalkyl of 3 to 20 carbon atoms, an aryl of 6 to 40 carbon atoms, a heteroaryl of 3 to 20 carbon atoms, a cyano, a halogen, a deuterium, and a hydrogen; and R's may each be connected to an adjacent substituent via alkylene or alkenylene to form an aliphatic ring or a mono- or polycyclic ring, and L may be connected to an adjacent substituent via alkylene or alkanylene to form a spiro ring or a fused ring.

According to an embodiment, the dopant represented by General Formula A-I may be any one selected from among the following compounds:

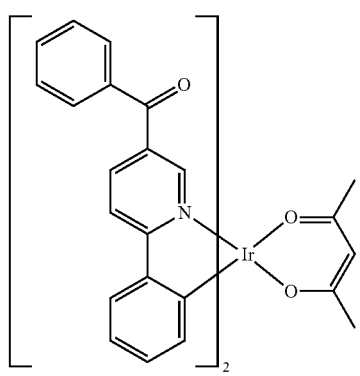

-continued
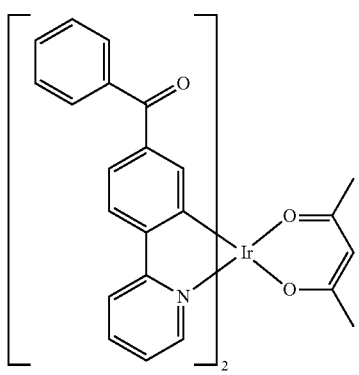
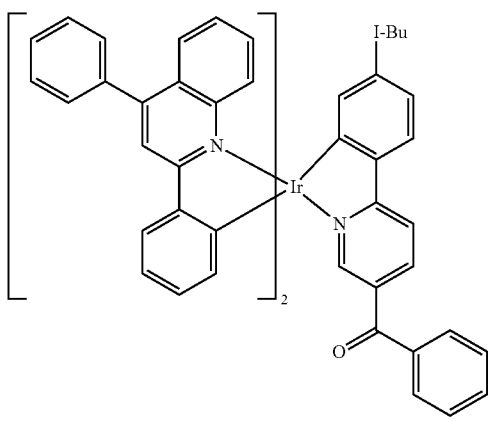
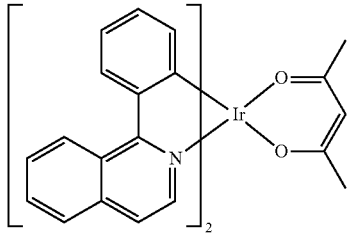
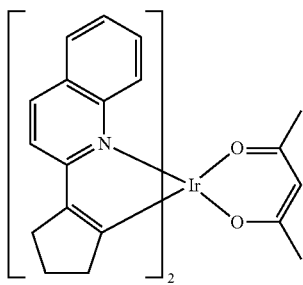
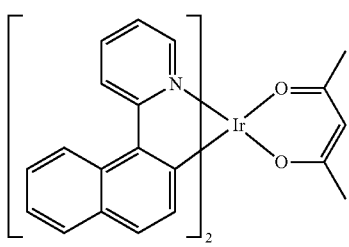
-continued
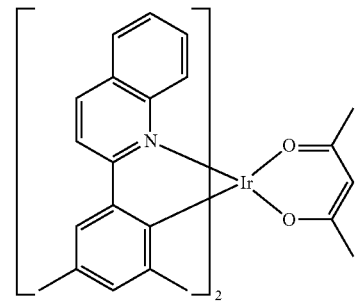
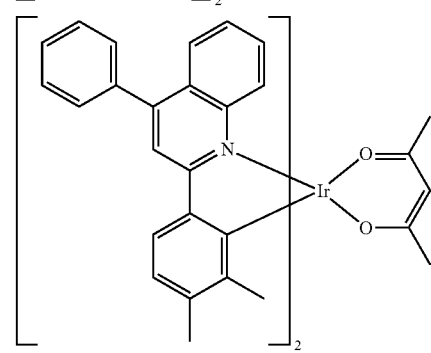
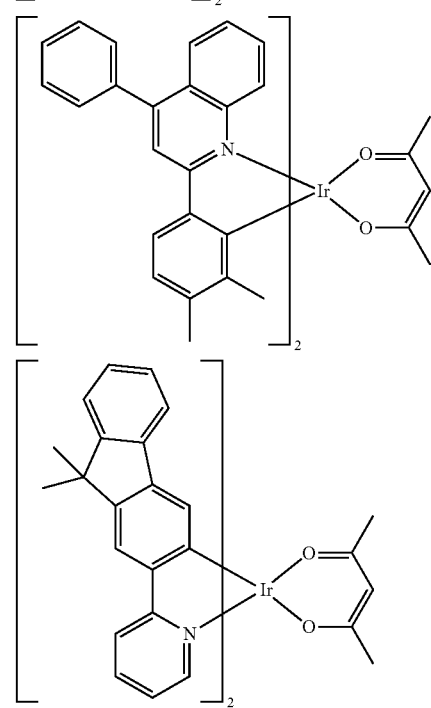
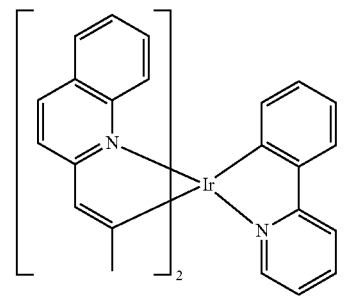
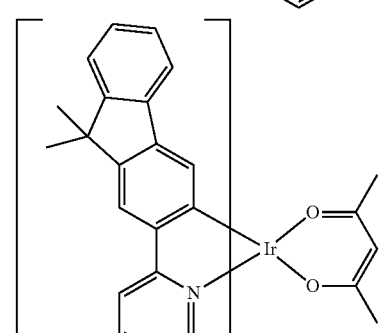

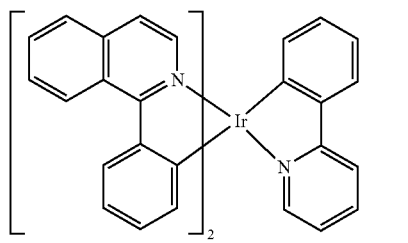
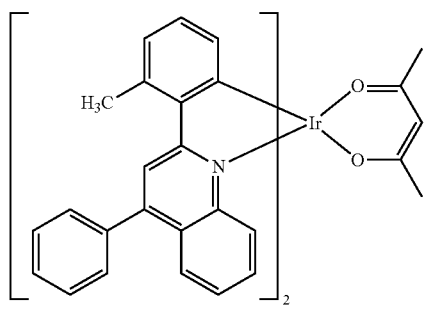
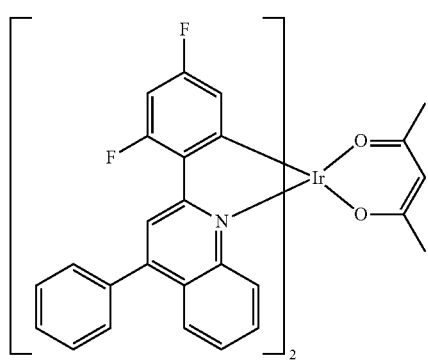
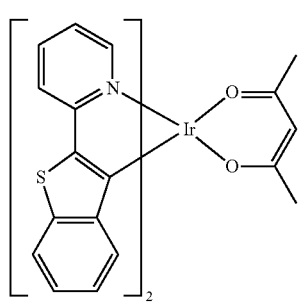
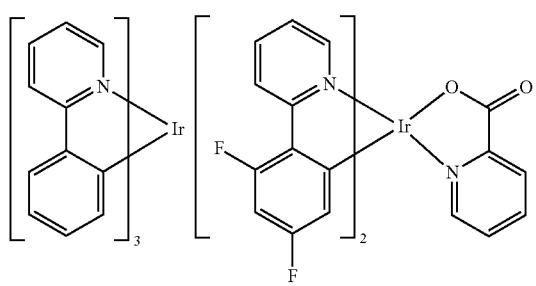
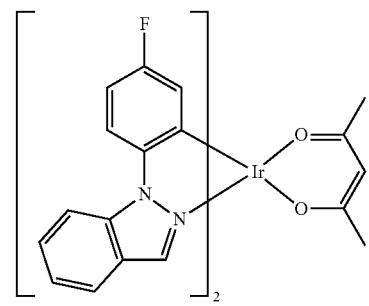
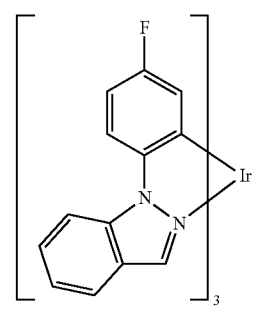
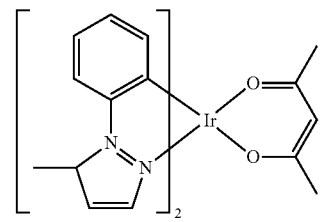
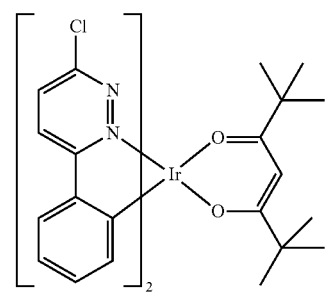
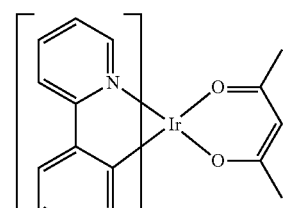
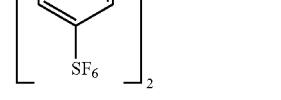
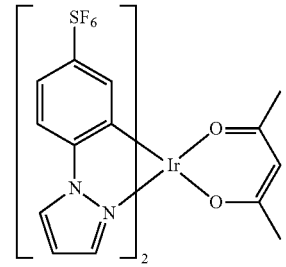

-continued
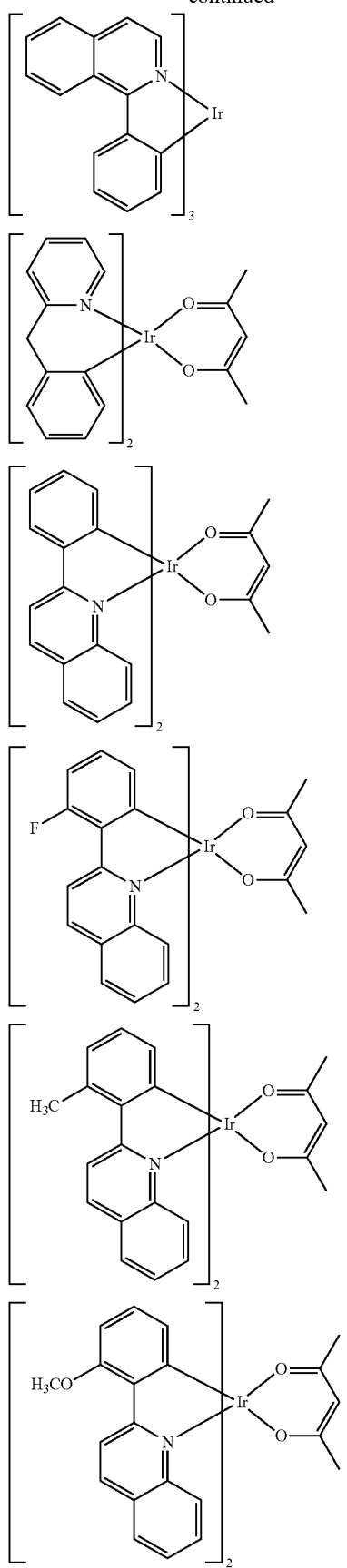
-continued
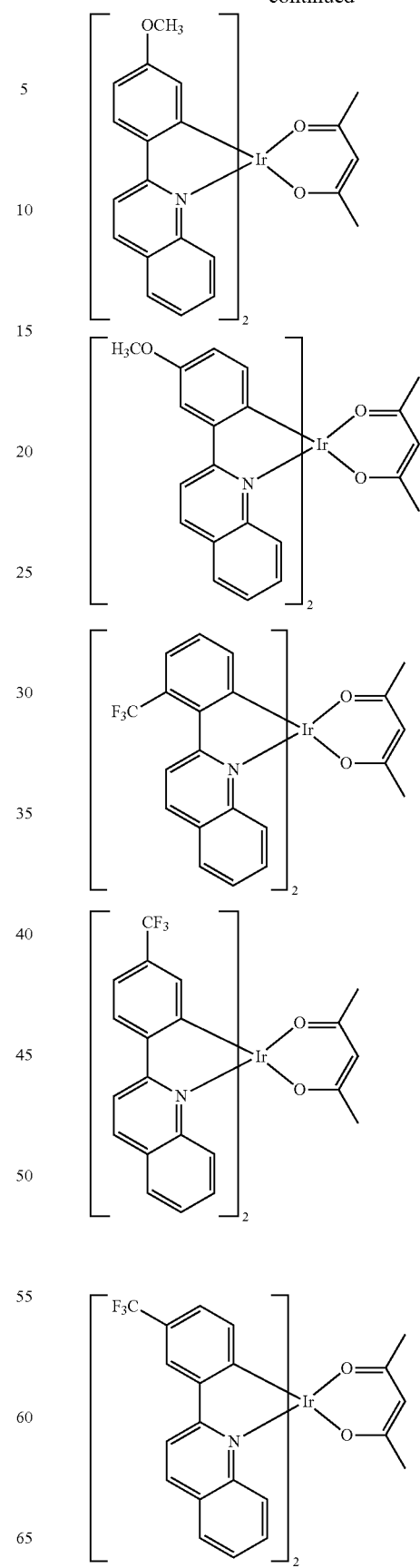

-continued
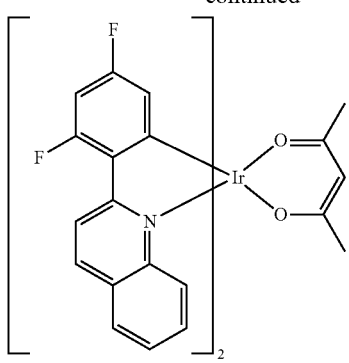
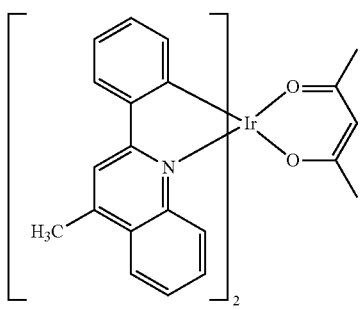
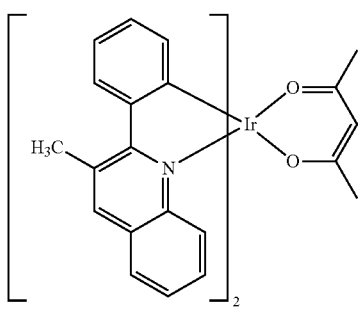
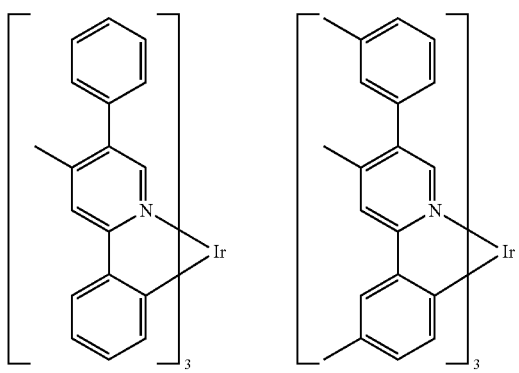
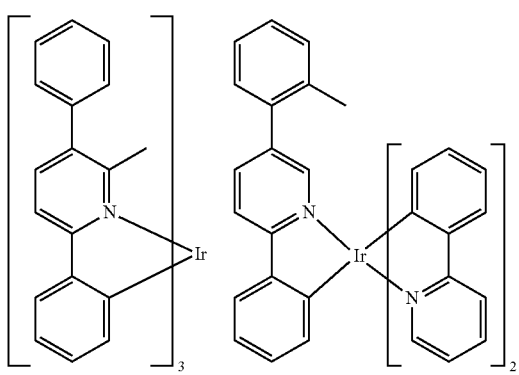
-continued
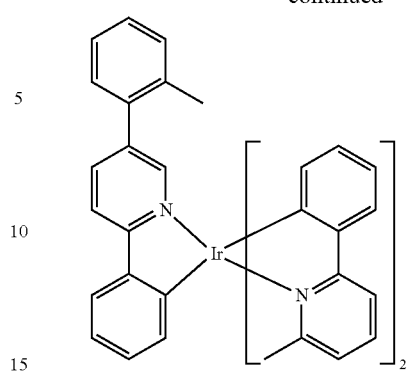
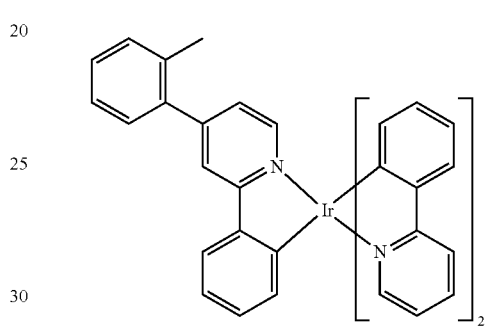
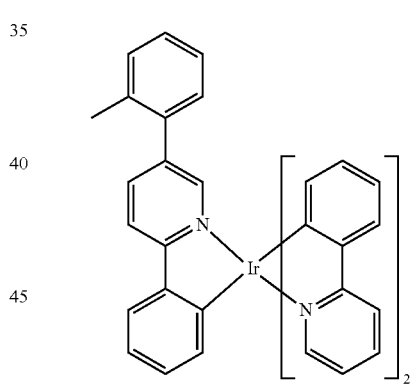
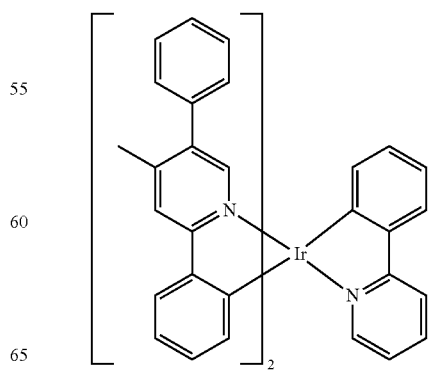

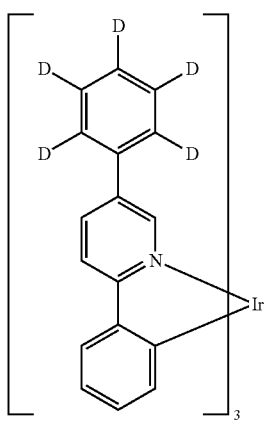
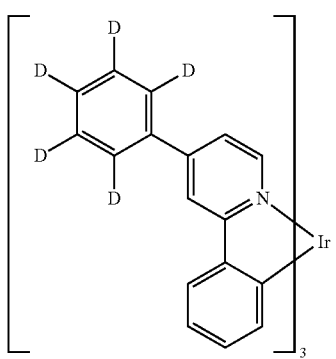
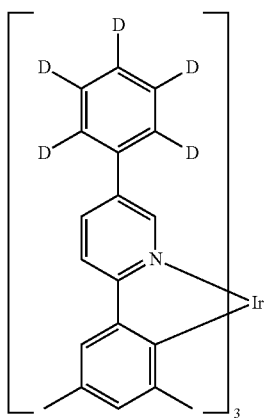
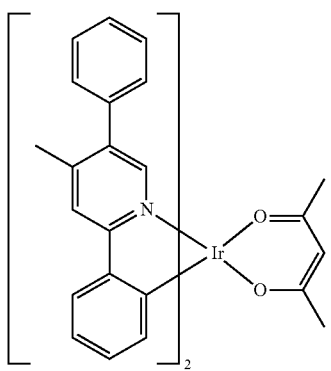
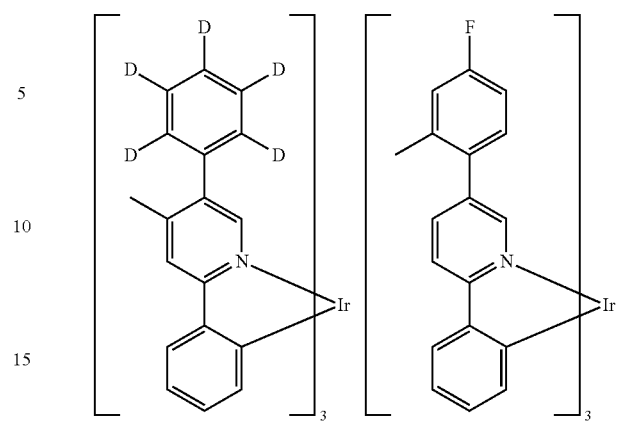
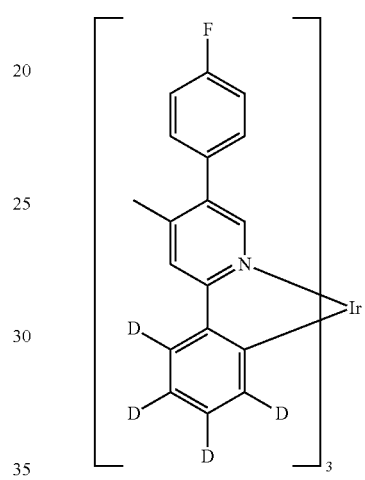
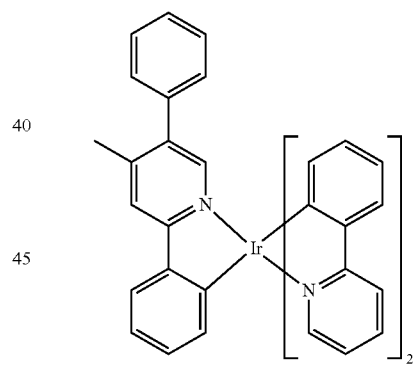
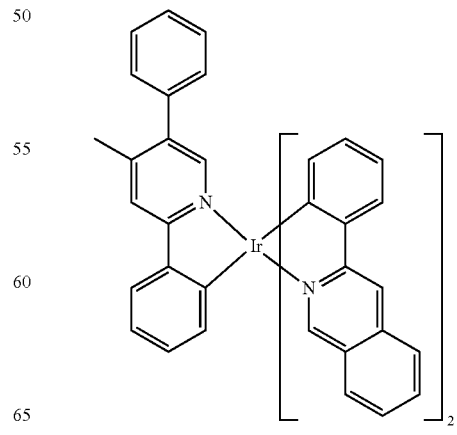

87
-continued
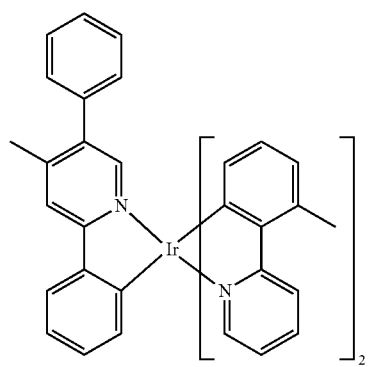
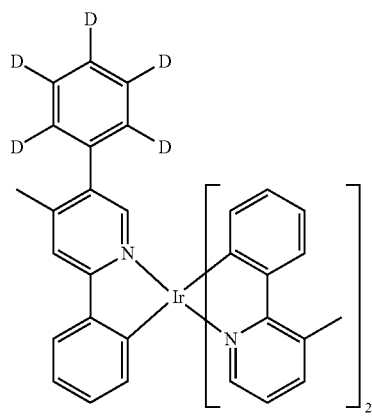
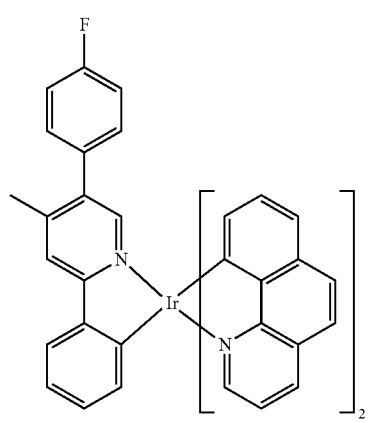
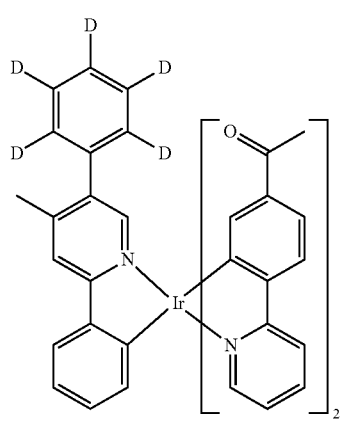
88
-continued
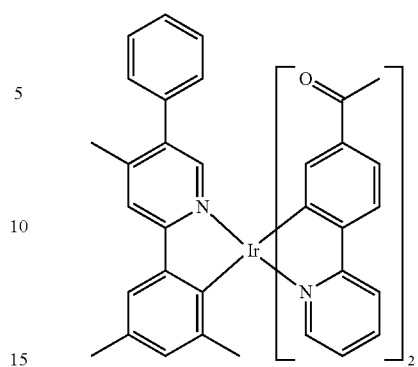
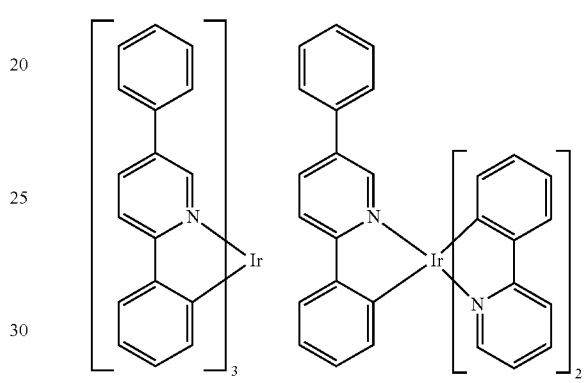
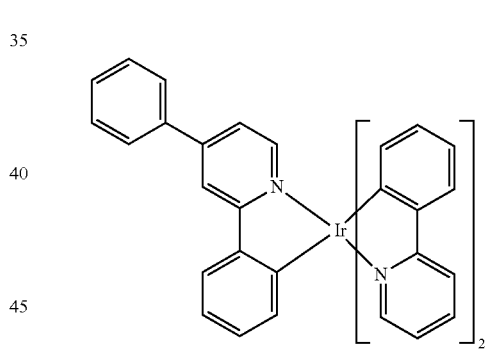
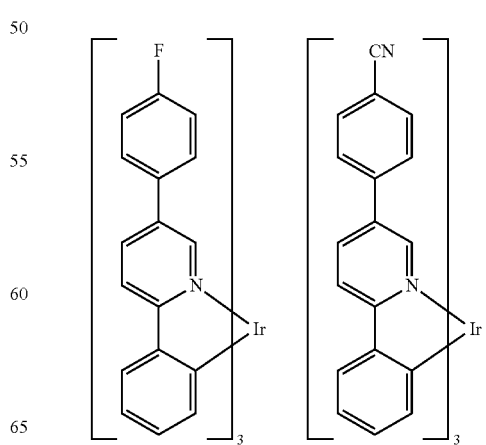

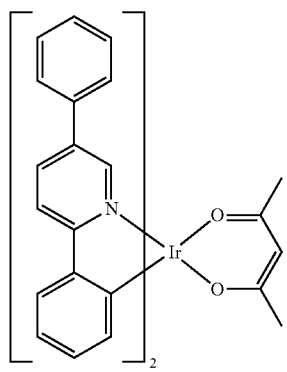
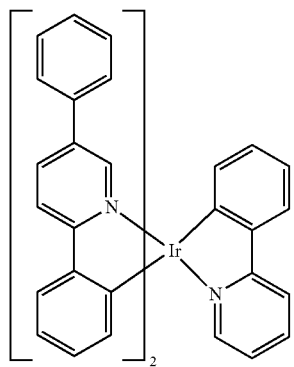
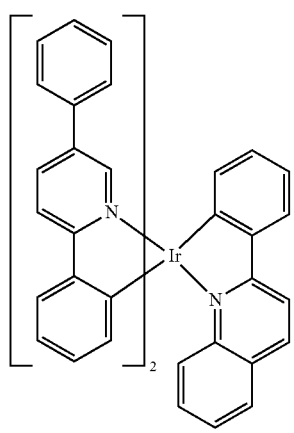
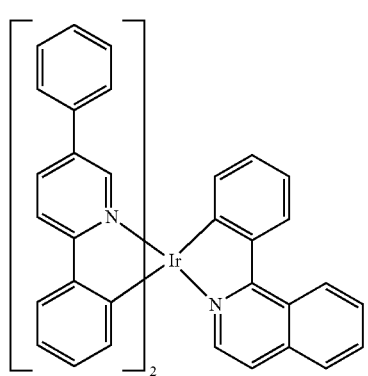
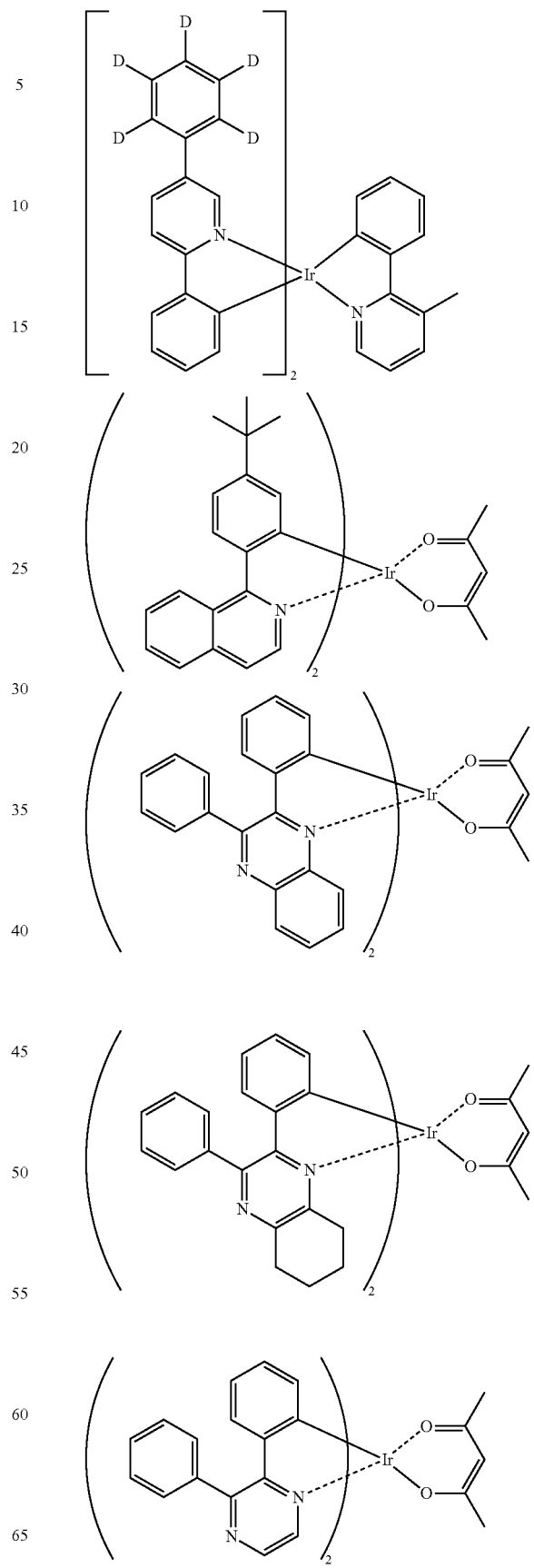

-continued

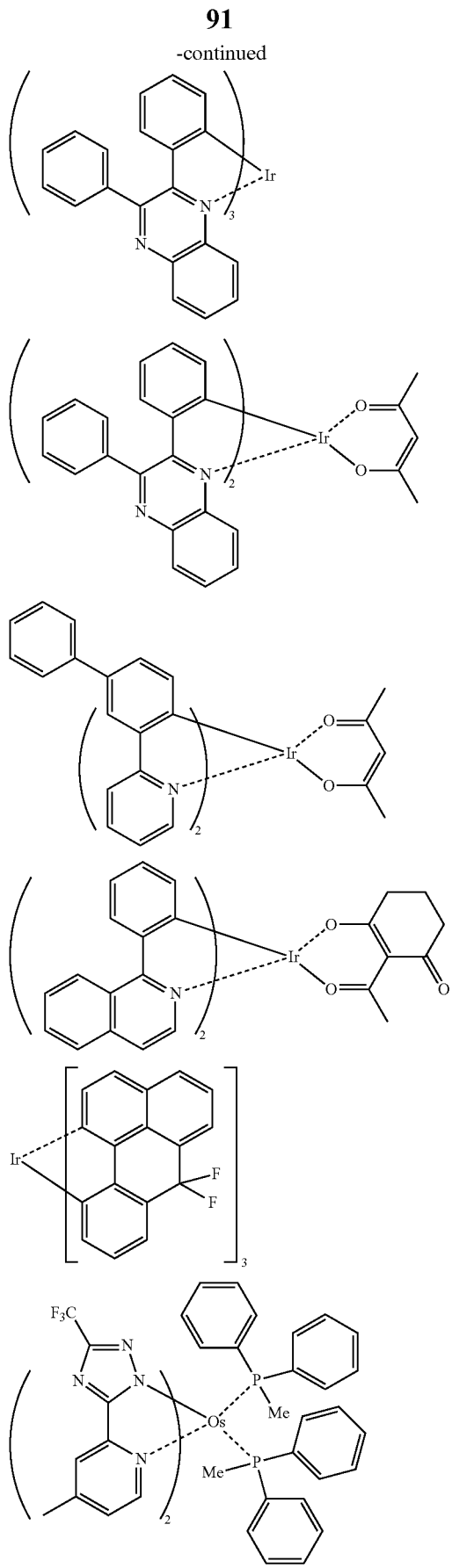

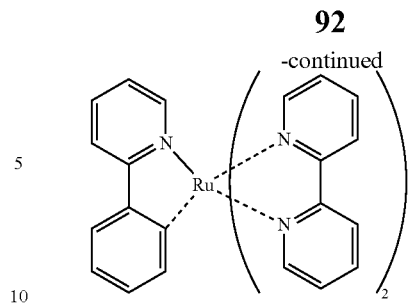

The light-emitting layer may contain various host and dopant materials in addition to the aforementioned dopant and host materials.

Further, one or more layers selected from among a hole injection layer, a hole transport layer, an electron barrier layer, a light-emitting layer, a hole barrier layer, an electron transport layer, and an electron injection layer may be deposited using a single molecule deposition process or a solution process. Here, the deposition process refers to a process by which a material is vaporized in a vacuum or at a low pressure and deposited to form a layer, and the solution process means a method in which a material is dissolved in a solvent and applied for the formation of a thin film by means of inkjet printing, roll-to-roll coating, screen printing, spray coating, dip coating, spin coating, etc.

Also, the organic light-emitting device of the present invention may be applied to a device selected from among flat display devices, flexible display devices, monochrome or white flat illumination devices, and monochrome or white flexible illumination devices.

A better understanding of the present invention may be obtained through the following examples which are set forth to illustrate, but are not to be construed as limiting the present invention.

EXAMPLES

Synthesis Example 1

Synthesis of Compound 1

[Reaction Scheme 1-1] Synthesis of [Intermediate 1-a]

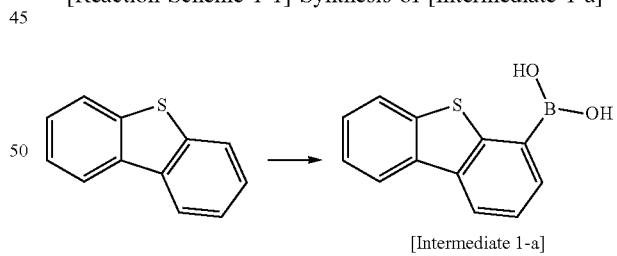

[Intermediate 1-a]

In a 1-L reactor, tetrahydrofuran (500 mL) and dibenzothiophene (50 g, 271 mmol) were placed and cooled to −78° C. under a nitrogen atmosphere. After 30 min, drops of 1.6 M n-butyllithium (203 mL, 325 mmol) were slowly added, and stirred for 1 hour at 0° C. At −78° C., drops of trimethylborate (33.8 g, 325 mmol) were slowly added, and then heated to room temperature. After 2 hours of stirring, the reaction was terminated with an aqueous hydrochloride solution. The organic layer was extracted and distilled at a reduced pressure. Recrystallization in hexane was followed by filtration and drying to afford Intermediate 1-a (51 g) as a solid: yield 83%.

[Reaction Scheme 1-2] Synthesis of [Intermediate 1-b]

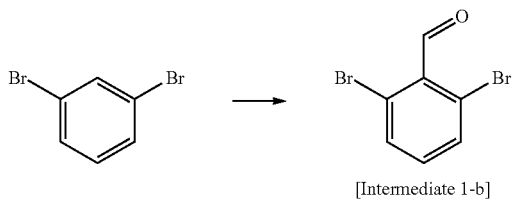 [SMILES: Brc1cccc(Br)c1 ; O=Cc1c(Br)cccc1Br]

[Intermediate 1-b]

In a 1-L reactor, tetrahydrofuran (500 mL) and 1,3-dibromobenzene (50 g, 212 mmol) were placed and cooled to −78° C. under a nitrogen atmosphere. Drops of 1.5M LDA (170 mL, 254 mmol) were slowly added and then stirred for 30 min. At the same temperature, DMF (18.5 g, 254 mmol) was slowly added in a dropwise manner, followed by stirring for 30 min. The reaction was terminated with an aqueous sulfuric acid solution. The organic layer was extracted and concentrated at a reduced pressure. Purification by column chromatography afforded Intermediate 1-b (49 g): yield 88%

[Reaction Scheme 1-3] Synthesis of [Intermediate 1-c]

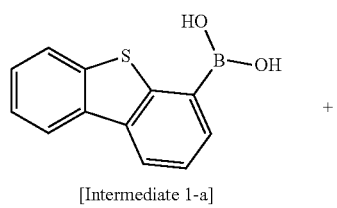

[Intermediate 1-a]

+

[Intermediate 1-b]

→

[Intermediate 1-c]

In a 2-L reactor, Intermediate 1-a (42 g, 185 mmol), Intermediate 1-b (49 g, 185 mmol), tetrakis(triphenylphosphine)palladium (4.3 g, 3.7 mmol), potassium carbonate (76.7 g, 555 mmol), toluene (600 mL), and distilled water (200 mL) were placed and stirred together at 100° C. for 12 hours. The reaction mixture was cooled to room temperature. Then the organic layer was extracted and concentrated at a reduced pressure. Purification by column chromatography afforded Intermediate 1-c (47 g): yield 69%

[Reaction Scheme 1-4] Synthesis of [Intermediate 1-d]

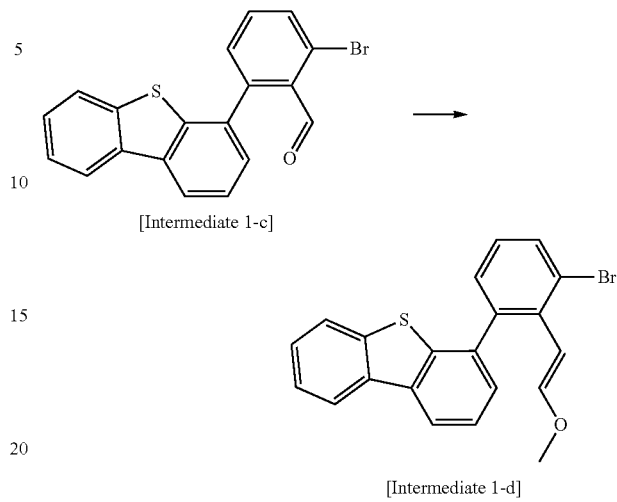

[Intermediate 1-c]

[Intermediate 1-d]

In a 2-L reactor, potassium tert-butoxide (23.4 g, 192 mmol) and tetrahydrofuran (200 ml) were stirred together and cooled to 0° C. under a nitrogen atmosphere. A solution of methoxymethyl triphenyl phosphonium chloride (65.8 g, 192 mmol) in tetrahydrofuran (300 ml) was dropwise added and then stirred for 30 min. A solution of Intermediate 1-c (47 g, 128 mmol) in tetrahydrofuran (500 ml) was slowly added and then stirred at room temperature for 2 hours. After completion of the reaction, the organic layer was extracted and concentrated at a reduced pressure. Purification by column chromatography afforded Intermediate 1-d (46.5 g): yield 92%

[Reaction Scheme 1-5] Synthesis of [Intermediate 1-e]

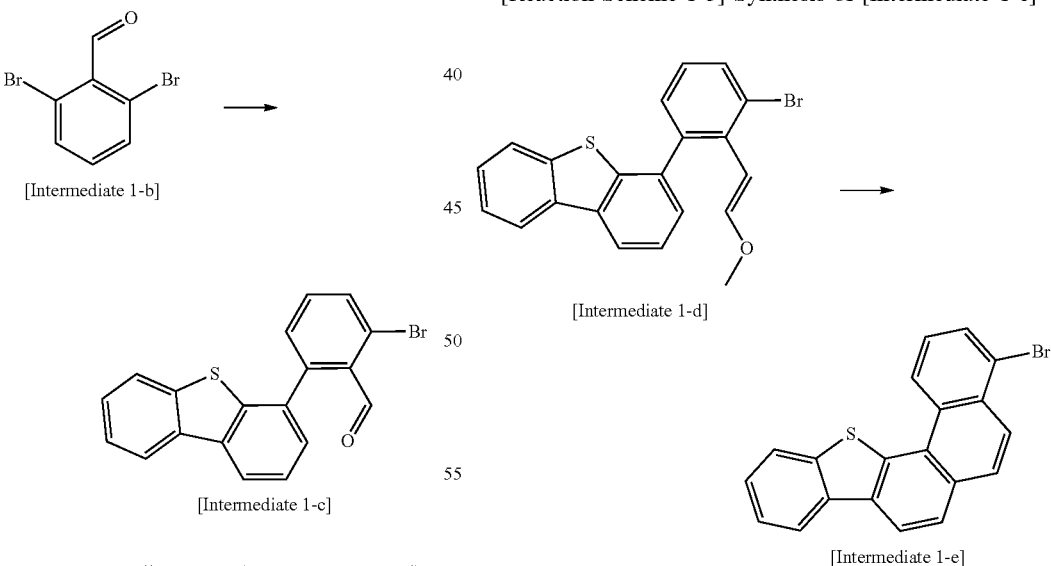

[Intermediate 1-d]

[Intermediate 1-e]

In a 1-L reactor, Intermediate 1-d (46 g, 116 mmol), bismuth (III) trifluoromethane sulfonate (3.8 g, 5.8 mmol), and 1,2-dichloroethane (500 ml) were placed and stirred together at room temperature for 3 hours under a nitrogen atmosphere. After completion of the reaction, precipitates were formed with methyl alcohol and filtered to afford Intermediate 1-e (38 g) as a solid: yield 89%

[Reaction Scheme 1-6] Synthesis of [Intermediate 1-f]

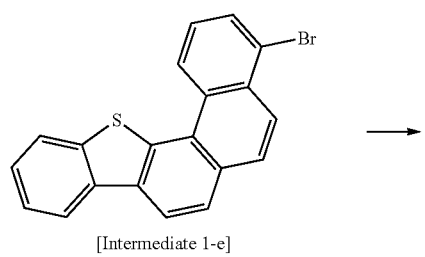

[Intermediate 1-e]

↓

[Intermediate 1-f]

In a 2-L reactor, Intermediate 1-e (20 g, 55 mmol), bis(pinacolato)diboron (15.4 g, 60 mmol), [1,1'-bis(diphenylphosphino)ferocene]dichloropalladium (1.2 g, 1.65 mmol), potassium acetate 15.7 g (165 mmol) and toluene (200 mL) were placed and refluxed for 12 hours. Following filtration at a high temperature, the filtrate was concentrated at a reduced pressure. Purification by column chromatography afforded Intermediate 1-f (17 g): yield 75%

[Reaction Scheme 1-7] Synthesis of [Intermediate 1-g]

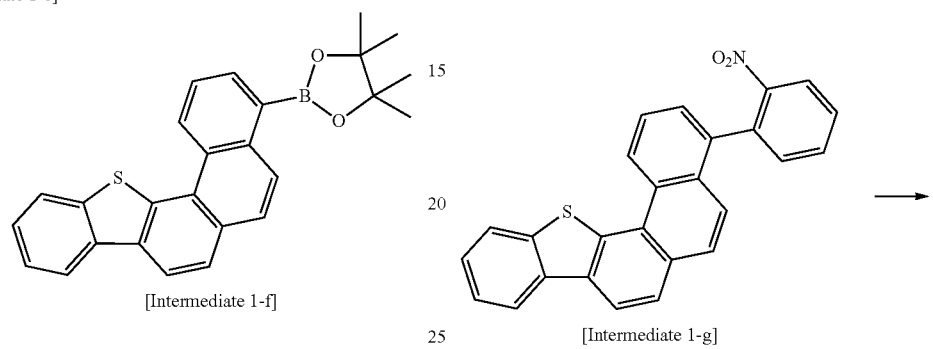

[Intermediate 1-f]

+

[Intermediate 1-g]

In a 2-L reactor, Intermediate 1-f (17 g, 41 mmol), 1-bromo-2-nitrobenzene (8.4 g, 41 mmol), tetrakis(triphenylphosphine)palladium (0.95 g, 0.82 mmol), potassium carbonate (17 g, 123 mmol), 1,4-dioxane (80 mL), toluene (80 mL), and distilled water (40 mL) were placed and stirred together at 100° C. for 48 hours. The reaction mixture was cooled to room temperature. The organic layer was extracted and concentrated at room temperature. Purification by column chromatography afforded Intermediate 1-g (15 g): yield 90%)

[Reaction Scheme 1-8] Synthesis of [Intermediate 1-h]

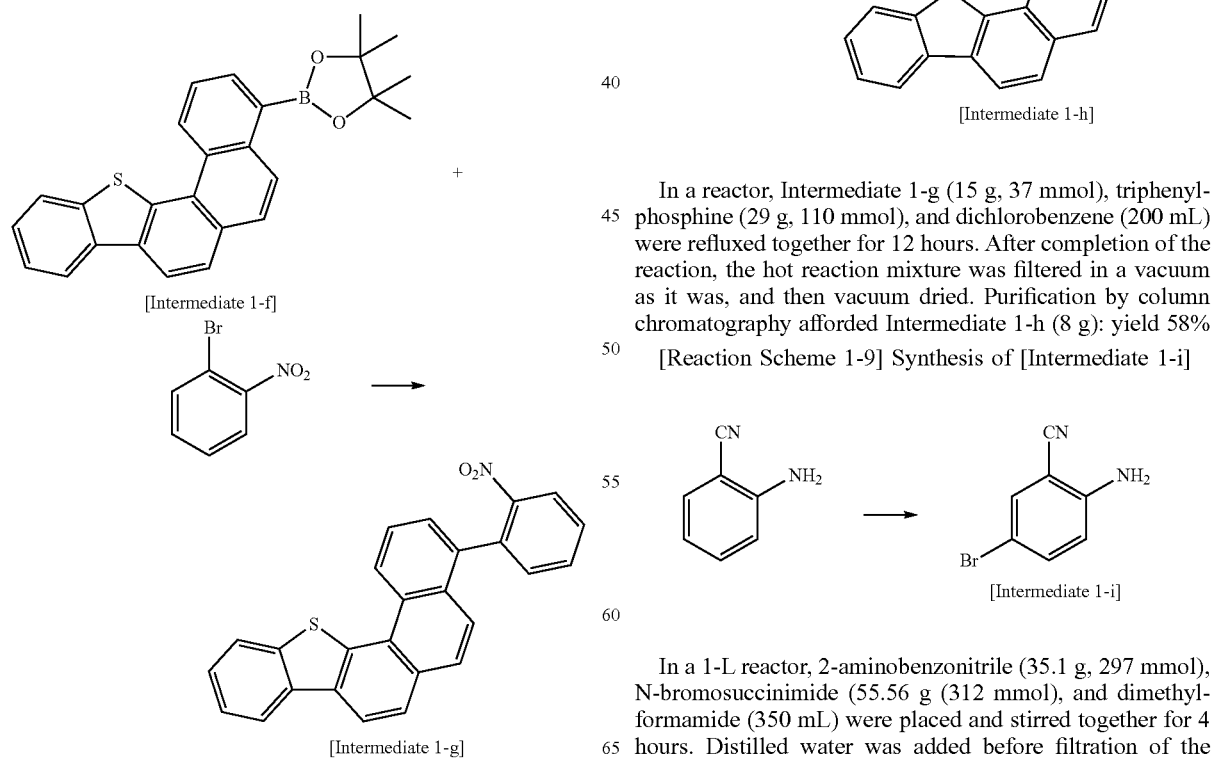

[Intermediate 1-g]

↓

[Intermediate 1-h]

In a reactor, Intermediate 1-g (15 g, 37 mmol), triphenylphosphine (29 g, 110 mmol), and dichlorobenzene (200 mL) were refluxed together for 12 hours. After completion of the reaction, the hot reaction mixture was filtered in a vacuum as it was, and then vacuum dried. Purification by column chromatography afforded Intermediate 1-h (8 g): yield 58%

[Reaction Scheme 1-9] Synthesis of [Intermediate 1-i]

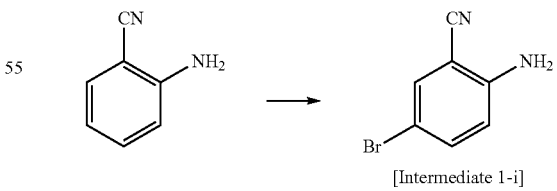

[Intermediate 1-i]

In a 1-L reactor, 2-aminobenzonitrile (35.1 g, 297 mmol), N-bromosuccinimide (55.56 g (312 mmol), and dimethylformamide (350 mL) were placed and stirred together for 4 hours. Distilled water was added before filtration of the reaction mixture. Purification by column chromatography afforded Intermediate 1-i (54.2 g): yield 92.6%

[Reaction Scheme 1-10] Synthesis of [Intermediate 1-j]

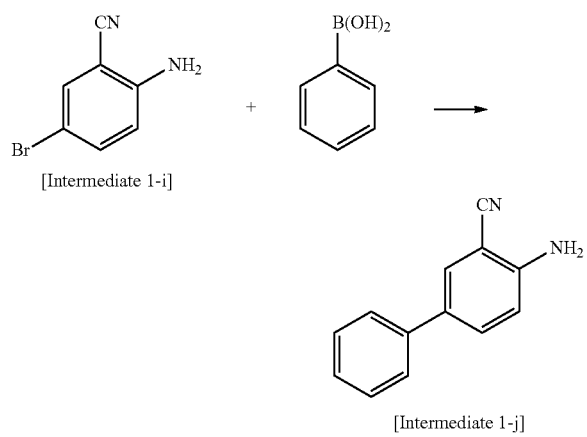

[Intermediate 1-i]

[Intermediate 1-j]

In a 2-L reactor, Intermediate 1-i (50 g, 254 mmol), phenyl boronic acid (40.2 g, 330 mmol), tetrakis(triphenylphosphine)palladium (13.3 g, 12.0 mmol), potassium carbonate (70.1 g, 508 mmol), 1,4-dioxane (250 mL), toluene (250 mL), and distilled water (100 mL) were placed and stirred at 100° C. for 12 hours. The reaction mixture was cooled to room temperature. Then, the organic layer was extracted and concentrated at a reduced temperature. Purification by column chromatography afforded Intermediate 1-j (45 g): yield 91%

[Reaction Scheme 1-11] Synthesis of [Intermediate 1-k]

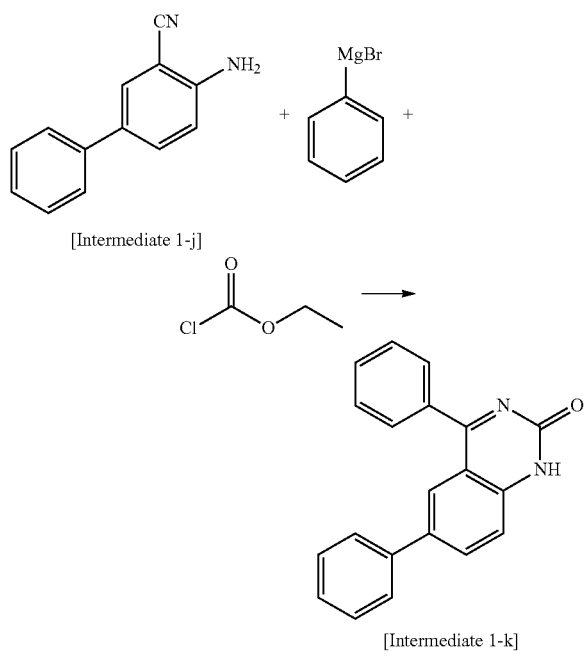

[Intermediate 1-j]

[Intermediate 1-k]

In a 2-L reactor, Intermediate 1-j (45.0 g, 232 mmol) and tetrahydrofuran (450 mL) were placed and stirred together. The temperature was lowered to 0° C., and drops of 3M-phenyl magnesium bromide (88.2 mL, 487 mmol) were added, followed by refluxing for 3 hours. A solution of ethyl chloroformate (44.3 g, 732 mmol) in tetrahydrofuran (200 mL) was dropwise added and then refluxed for 2 hours. The reaction mixture was cooled to 0° C. and added with an aqueous saturated ammonium chloride solution. The organic layer was then extracted and concentrated at a reduced pressure. Purification by column chromatography afforded Intermediate 1-k (46 g): yield 80%

[Reaction Scheme 1-12] Synthesis of [Intermediate 1-l]

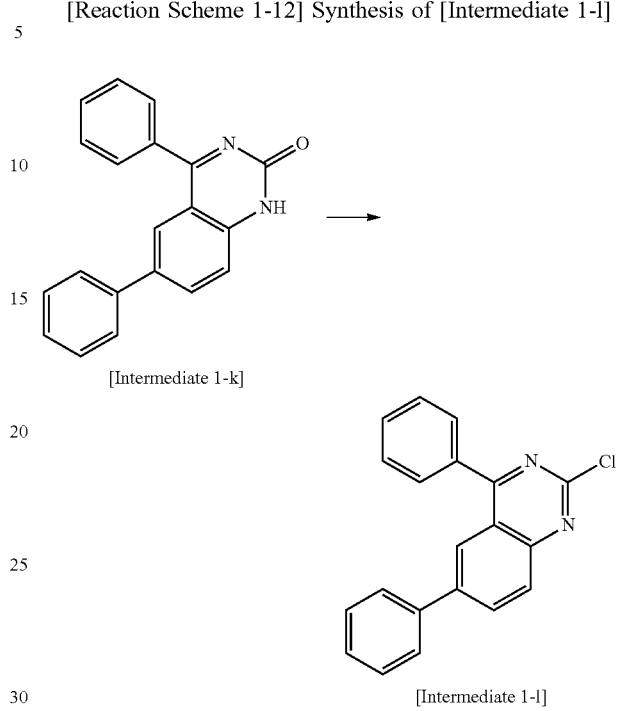

[Intermediate 1-k]

[Intermediate 1-l]

In a 2-L reactor, Intermediate 1-k (40 g, 134 mmol) and phosphorous oxychloride (500 mL) were placed and refluxed for 5 hours. The temperature was lowered to 0° C. before addition of drops of distilled water. The reaction mixture was filtered. Purification by column chromatography afforded Intermediate 1-1 (30.5 g) as a solid: yield 70.6%

[Reaction Scheme 1-13] Synthesis of [Compound 1]

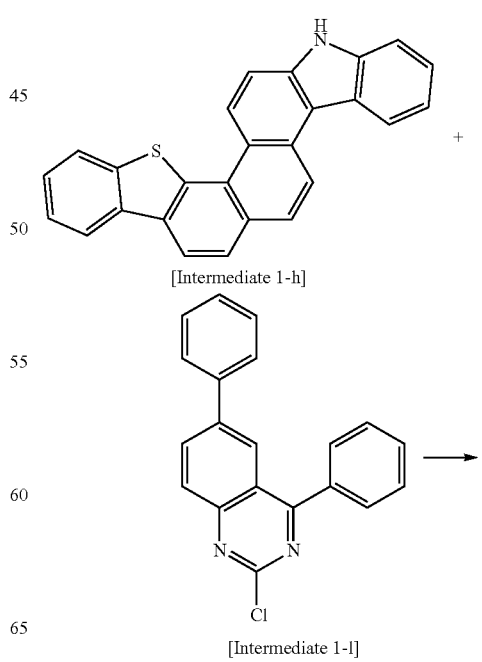

[Intermediate 1-h]

[Intermediate 1-l]

-continued

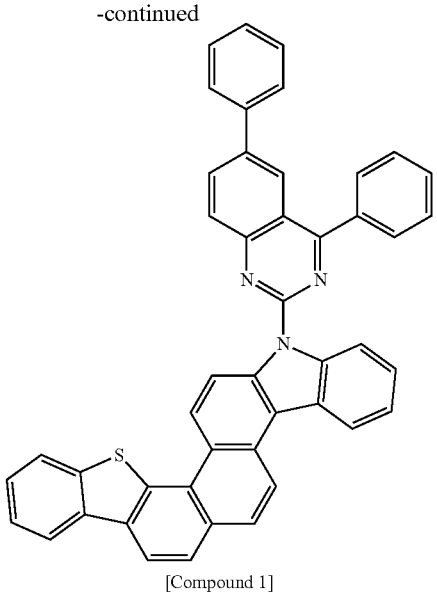

[Compound 1]

In a 300-mL reactor, Intermediate 1-h (4 g, 11 mmol), Intermediate 1-1 (4.2 g, 13 mmol), tris(dibenzylideneacetone)dipalladium (0.2 g, 0.22 mmol), tri-tert-butylphosphonium tetrafluoroborate (0.3 g, 1.1 mmol), sodium tert-butoxide (2.1 g, 22 mmol), and xylene (70 mL) were placed and refluxed for 12 hours. At a high temperature, the reaction mixture was filtered, and the filtrate was concentrated in a vacuum. Purification by column chromatography afforded Compound 1 (4.5 g): yield 62%

MS (MALDI-TOF): m/z 653.19 [M]$^+$

Synthesis Example 2

Synthesis of Compound 3

[Reaction Scheme 2-1] Synthesis of [Intermediate 2-a]

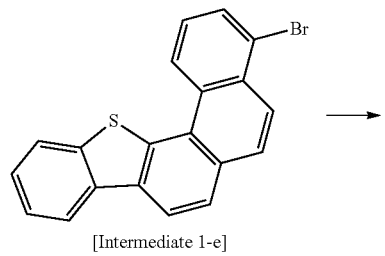

[Intermediate 1-e]

→

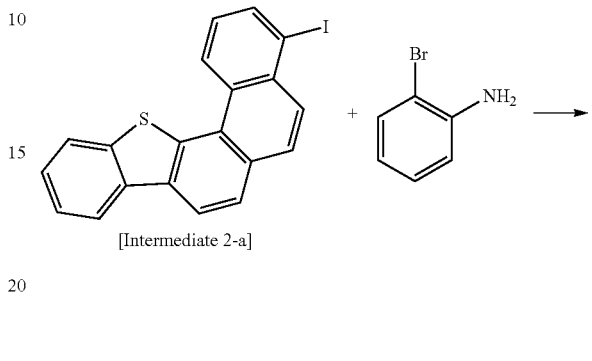

[Intermediate 2-a]

In a 500-mL reactor, Intermediate 1-e (20 g, 55 mmol) and tetrahydrofuran (200 mL) were placed and stirred together. After the mixture was cooled to −78° C., 1.6M N-butyl-lithium (41 mL, 66 mmol) was dropwise added and stirred for 1 hour. Iodine (16.7 g, 66 mmol) was added, followed by heating to room temperature and stirring for 2 hours. An aqueous sodium thiosulfate solution was added and an organic layer was extracted. Purification by column chromatography afforded Intermediate 2-a (20.4 g): yield 91%

[Reaction Scheme 2-2] Synthesis of [Intermediate 2-b]

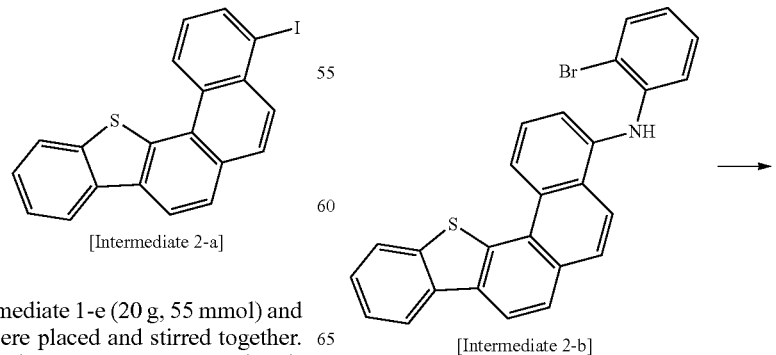

[Intermediate 2-b]

In a 500-mL reactor, Intermediate 2-a (22 g, 53 mmol), 2-bromoaniline (10.2 g, 59 mmol), tris(dibenzylideneacetone)dipalladium (0.96 g, 1.1 mmol), sodium tert-butoxide (10.2 g, 106 mmol), 2,2'-bis(diphenylphosphino)-1,1'-binaphthyl (1.32 g, 2.1 mmol), and toluene (250 ml) were placed and refluxed for 12 hours. The reaction mixture was filtered at a high temperature and concentrated at a reduced pressure. Purification by column chromatography afforded Intermediate 2-b (16 g): yield 66%

[Reaction Scheme 2-3] Synthesis of [Intermediate 2-c]

[Intermediate 2-b]

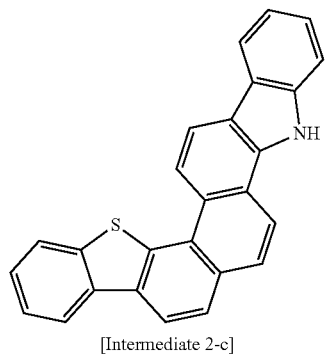

[Intermediate 2-c]

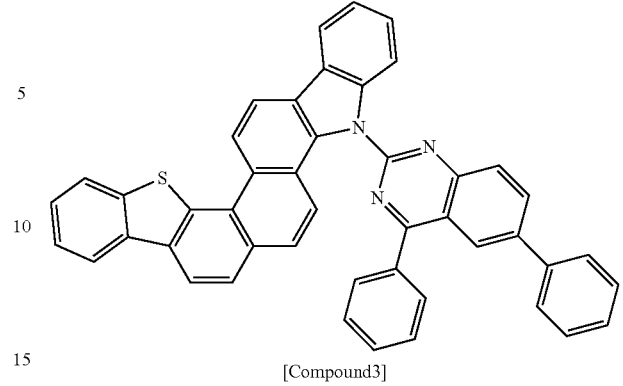

[Compound3]

In a 500-mL reactor, Intermediate 2-b (16 g, 35 mmol), tetrakis(triphenylphosphine)palladium (0.8 g, 0.7 mmol), potassium acetate (4.1 g, 42 mmol), and dimethylformamide (200 mL) were placed and refluxed together for 12 hours. The reaction mixture was cooled to room temperature, and the organic layer was extracted and concentrated at a reduced pressure. Purification by column chromatography afforded Intermediate 2-c (6 g): yield 46%

[Reaction Scheme 2-4] Synthesis of [Compound3]

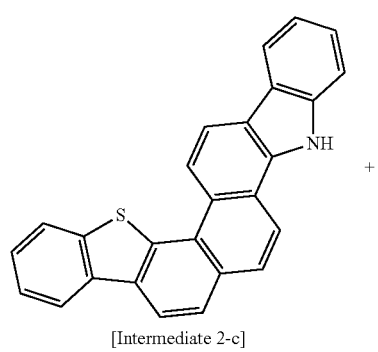

[Intermediate 2-c]

+

The same procedure as in Reaction Scheme 1-13 of Synthesis Example 1 was carried out, with the exception of using Intermediate 2-c] instead of Intermediate 1-h, to afford Compound 3 (4.3): yield 42.8%

MS (MALDI-TOF): m/z 653.19 [M]$^+$

Synthesis Example 3

Synthesis of Compound 6

[Reaction Scheme 3-1] Synthesis of [Intermediate 3-a]

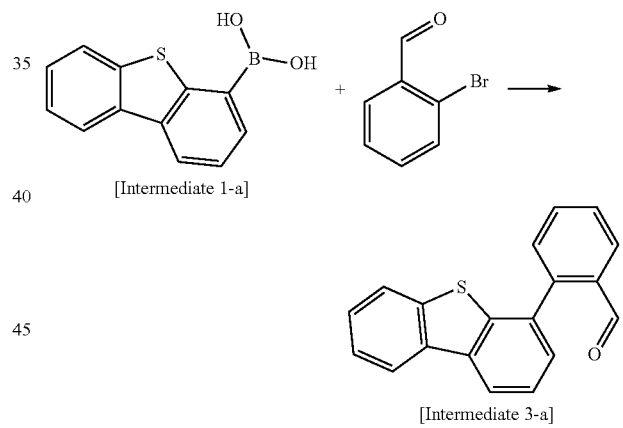

[Intermediate 1-a]

[Intermediate 3-a]

The same procedure as in Reaction Scheme 1-3 of Synthesis Example 1 was carried out, with the exception of using 2-bromo benzaldehyde instead of Intermediate 1-b, to afford Intermediate 3-a (32.5 g): yield 69%

[Reaction Scheme 3-2] Synthesis of [Intermediate 3-b]

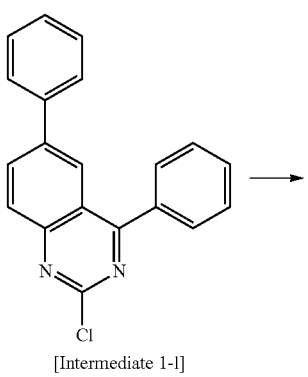

[Intermediate 1-l]

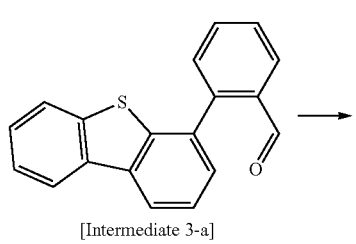

[Intermediate 3-a]

-continued

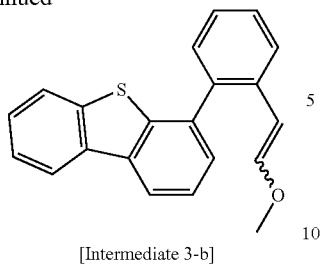

[Intermediate 3-b]

The same procedure as in Reaction Scheme 1-4 of Synthesis Example 1 was carried out, with the exception of using Intermediate 3-a instead of Intermediate 1-c, to afford Intermediate 3-b (31.7 g): yield 89%

[Reaction Scheme 3-3] Synthesis of [Intermediate 3-c]

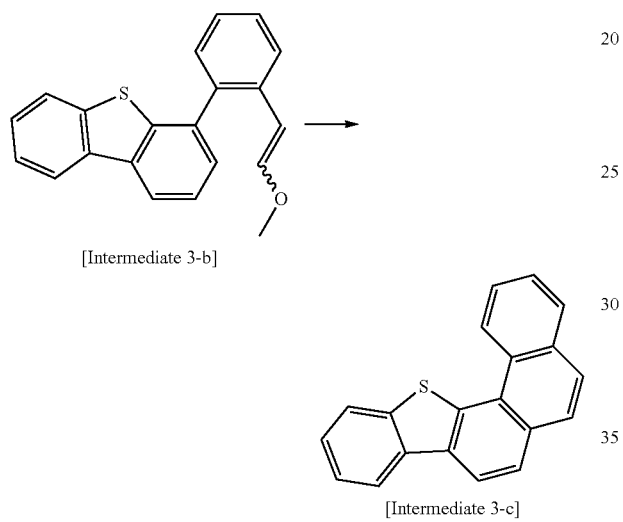

[Intermediate 3-b]

[Intermediate 3-c]

The same procedure as in Reaction Scheme 1-5 of Synthesis Example 1 was carried out, with the exception of using Intermediate 3-b instead of Intermediate 1-d, to afford Intermediate 3-c (24.8 g): yield 87%

[Reaction Scheme 3-4] Synthesis of Intermediate 3-d]

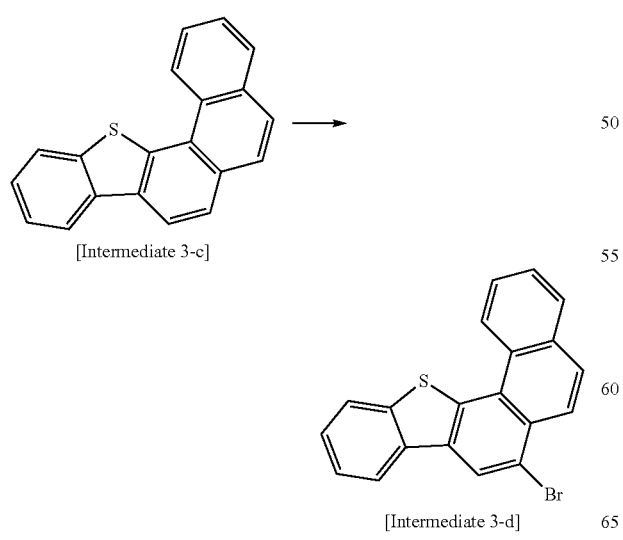

[Intermediate 3-c]

[Intermediate 3-d]

In a 1-L reactor, Intermediate 3-c (25 g, 87.9 mmol) and chloroform (250 ml) were placed and stirred together. At room temperature, bromine drops were slowly added, followed by stirring for 2 hours. Methanol was used to form precipitates which were then filtered to afford Intermediate 3-d (26.1 g): (yield 82%)

[Reaction Scheme 3-5] Synthesis of [Intermediate 3-e]

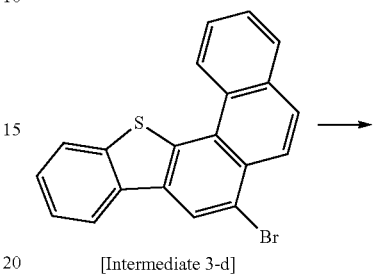

[Intermediate 3-d]

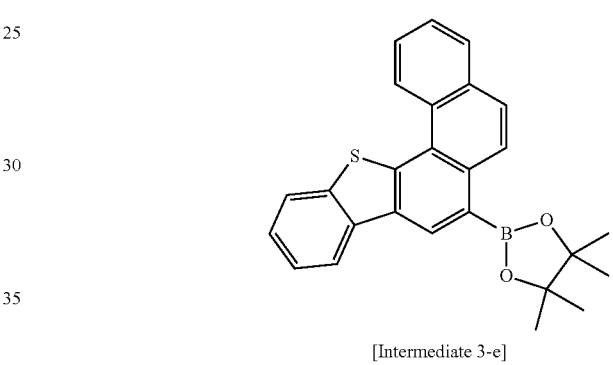

[Intermediate 3-e]

The same procedure as in Reaction Scheme 1-6 of Synthesis Example 1 was carried out, with the exception of using Intermediate 3-d instead of Intermediate 1-e, to afford Intermediate 3-e (24.7 g): yield 84%

[Reaction Scheme 3-6] Synthesis of [Intermediate 3-f]

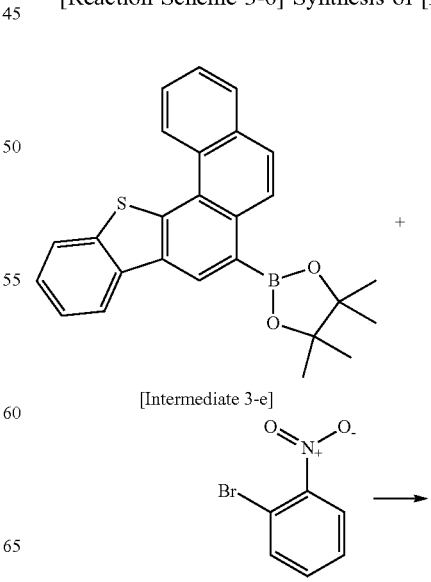

[Intermediate 3-e]

-continued

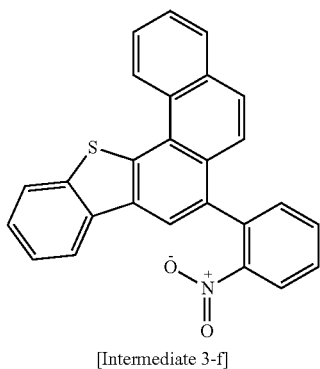
[Intermediate 3-f]

The same procedure as in Reaction Scheme 1-7 of Synthesis Example 1 was carried out, with the exception of using Intermediate 3-e instead of Intermediate 1-f, to afford Intermediate 3-f (19.7 g): yield 74%

[Reaction Scheme 3-7] Synthesis of [Intermediate 3-g]

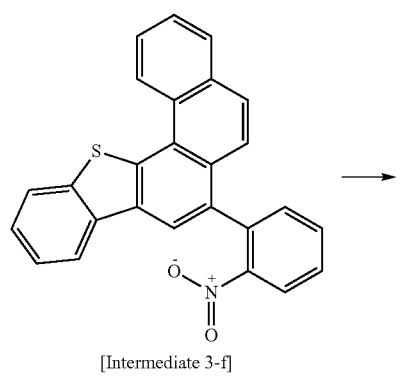
[Intermediate 3-f]

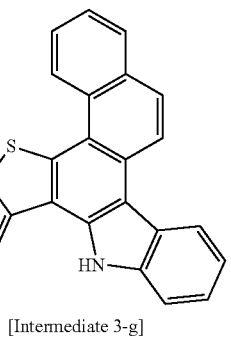
[Intermediate 3-g]

The same procedure as in Reaction Scheme 1-8 of Synthesis Example 1 was carried out, with the exception of using Intermediate 3-f instead of Intermediate 1-g, to afford Intermediate 3-g (9.3 g): yield 56%

[Reaction Scheme 3-8] Synthesis of [Intermediate 3-h]

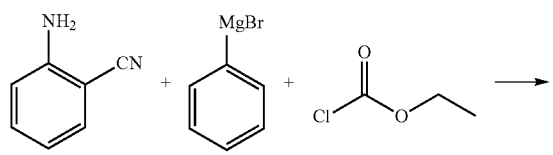

-continued

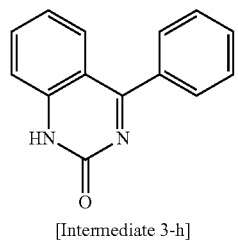
[Intermediate 3-h]

The same procedure as in Reaction Scheme 1-11 of Synthesis Example 1 was carried out, with the exception of using 2-aminobenzonitrile instead of Intermediate 1-j, to afford Intermediate 3-h (32.5 g): yield 77%)

[Reaction Scheme 3-9] Synthesis of [Intermediate 3-i]

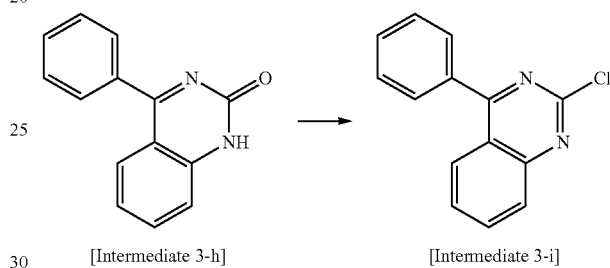
[Intermediate 3-h]   [Intermediate 3-i]

The same procedure as in Reaction Scheme 1-12 of Synthesis Example 1 was carried out, with the exception of using Intermediate 3-h in Reaction Scheme 3-8 instead of Intermediate 1-k, to afford Intermediate 3-i (24.3 g): yield 69%

[Reaction Scheme 3-10] Synthesis of [Compound 6]

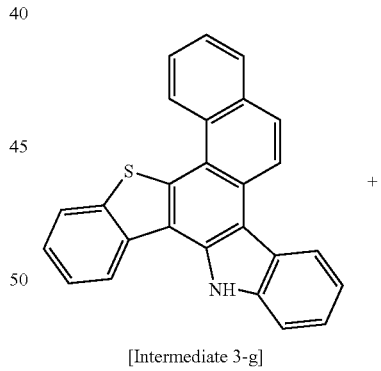
[Intermediate 3-g]

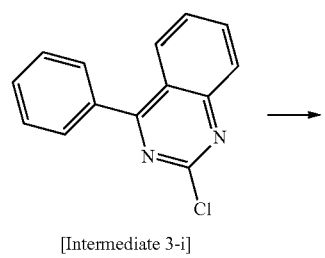
[Intermediate 3-i]

-continued

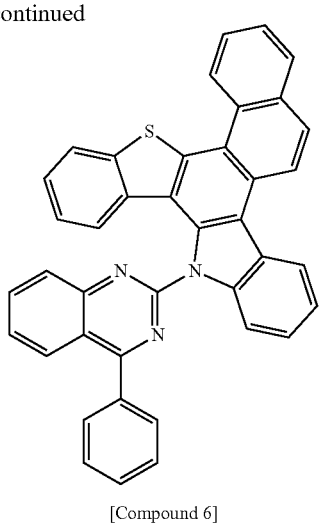

[Compound 6]

The same procedure as in Reaction Scheme 1-13 of Synthesis Example 1 was carried out, with the exception of using Intermediate 3-g and Intermediate 3-i instead of Intermediate 1-h and Intermediate 1-l, respectively, to afford Compound 6 (3.3 g): yield 41.3%

MS (MALDI-TOF): m/z 577.16 $[M]^+$

Synthesis Example 4

Synthesis of Compound 12

[Reaction Scheme 4-1] Synthesis of [Intermediate 4-a]

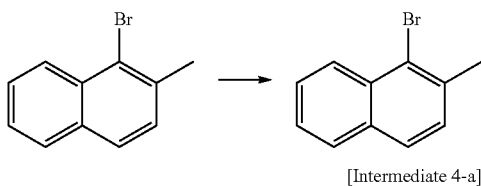

[Intermediate 4-a]

In a 2-L reactor, 1-bromo-2-methylnaphthalene (100 g, 452 mmol), N-bromosuccinimide (88.5 g, 497 mmol), benzoyl peroxide (2.2 g, 9.1 mmol), and 1,2-dichloroethane (1 L) were placed and refluxed together for 2 hours. The reaction mixture was cooled to room temperature, and an organic layer was extracted with methylene chloride, and concentrated at a reduced pressure. Purification by column chromatography afforded Intermediate 4-a (78.6 g): yield 58%

[Reaction Scheme 4-2] Synthesis of [Intermediate 4-b]

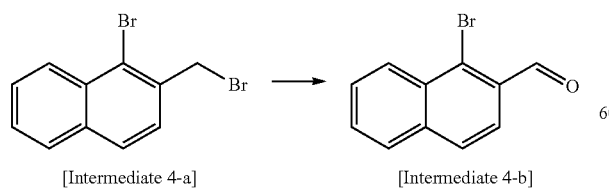

[Intermediate 4-a]   [Intermediate 4-b]

In a 2-L reactor, 4-methylmorpholine N-oxide (61.4 g, 524 mmol), a molecular sieve (200 g), and acetonitrile (1.2 L) were placed and stirred for 30 min at 0° C. under a nitrogen atmosphere. Intermediate 4-a (78 g, 262 mmol) was added, followed by stirring at room temperature for 6 hours. After completion of the reaction, the reaction mixture was filtered and washed with methylene chloride. The filtrate was concentrated and then isolated through column chromatography to afford Intermediate 4-b (45 g): yield 73%

[Reaction Scheme 4-3] Synthesis of [Intermediate 4-c]

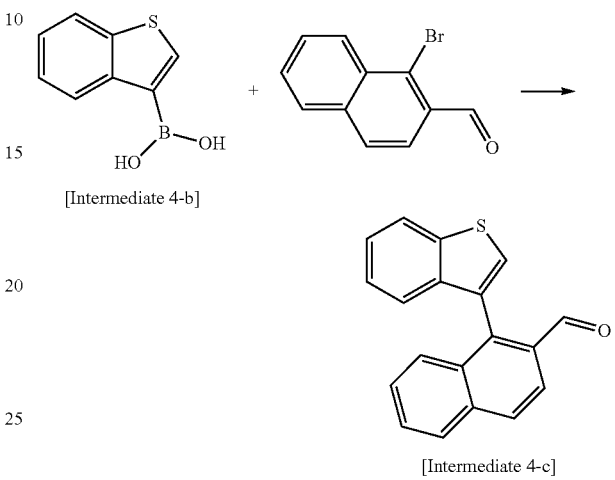

[Intermediate 4-b]

[Intermediate 4-c]

The same procedure as in Reaction Scheme 1-3 of Synthesis Example 1 was carried out, with the exception of using benzothionyl-3-boronic acid and Intermediate 4-b instead of Intermediate 1-a and Intermediate 1-b, respectively, to afford Intermediate 4-c (34 g): yield 69%

[Reaction Scheme 4-4] Synthesis of [Intermediate 4-d]

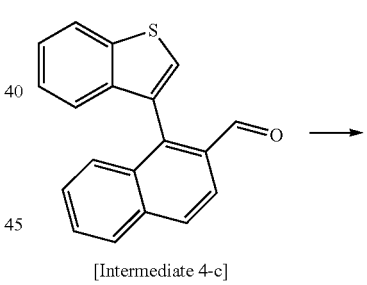

[Intermediate 4-c]

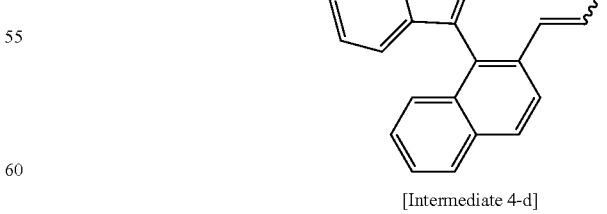

[Intermediate 4-d]

The same procedure as in Reaction Scheme 1-4 of Synthesis Example 1 was carried out, with the exception of using Intermediate 4-c instead of Intermediate 1-c, to afford Intermediate 4-d (30.9 g): yield 84%

[Reaction Scheme 4-5] Synthesis of [Intermediate 4-e]

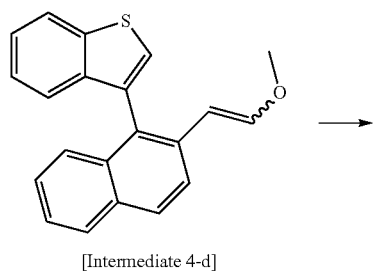

[Intermediate 4-d]

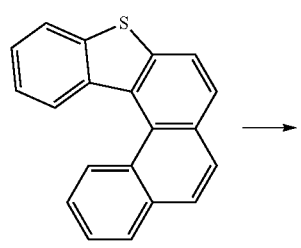

[Intermediate 4-e]

The same procedure as in Reaction Scheme 1-5 of Synthesis Example 1 was carried out, with the exception of using Intermediate 4-d instead of Intermediate 1-d, to afford Intermediate 4-e (23.2 g): yield 82%

[Reaction Scheme 4-6] Synthesis of [Intermediate 4-f]

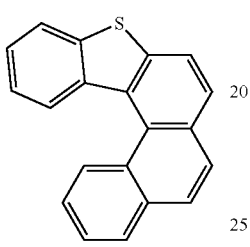

[Intermediate 4-e]

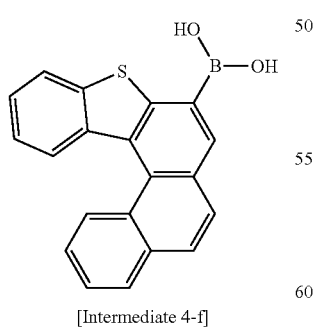

[Intermediate 4-f]

The same procedure as in Reaction Scheme 1-1 of Synthesis Example 1 was carried out, with the exception of using Intermediate 4-e instead of dibenzothiophene, to afford Intermediate 4-f (26.1 g): yield 77%

[Reaction Scheme 4-7] Synthesis of [Intermediate 4-g]

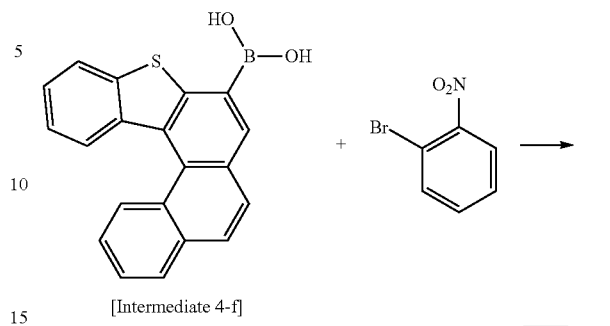

[Intermediate 4-f]

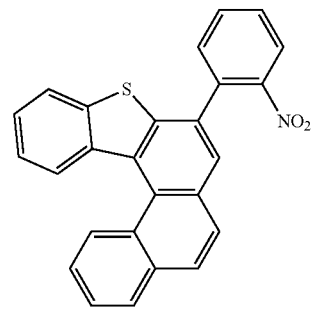

[Intermediate 4-g]

The same procedure as in Reaction Scheme 1-7 of Synthesis Example 1 was carried out, with the exception of using Intermediate 4-f instead of Intermediate 1-f, to afford Intermediate 4-g (22.3 g): yield 69%

[Reaction Scheme 4-8] Synthesis of [Intermediate 4-h]

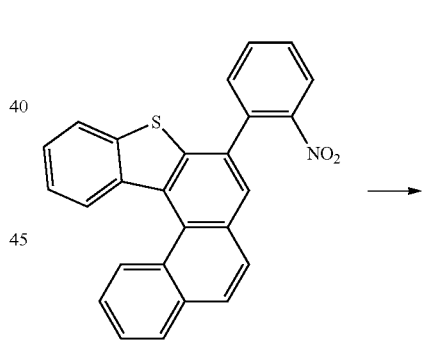

[Intermediate 4-g]

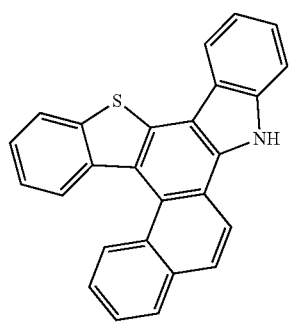

[Intermediate 4-h]

The same procedure as in Reaction Scheme 1-8 of Synthesis Example 1 was carried out, with the exception of using Intermediate 4-g instead of Intermediate 1-g, to afford Intermediate 4-h (11.3 g): yield 55%

[Reaction Scheme 4-9] Synthesis of [Compound 12]

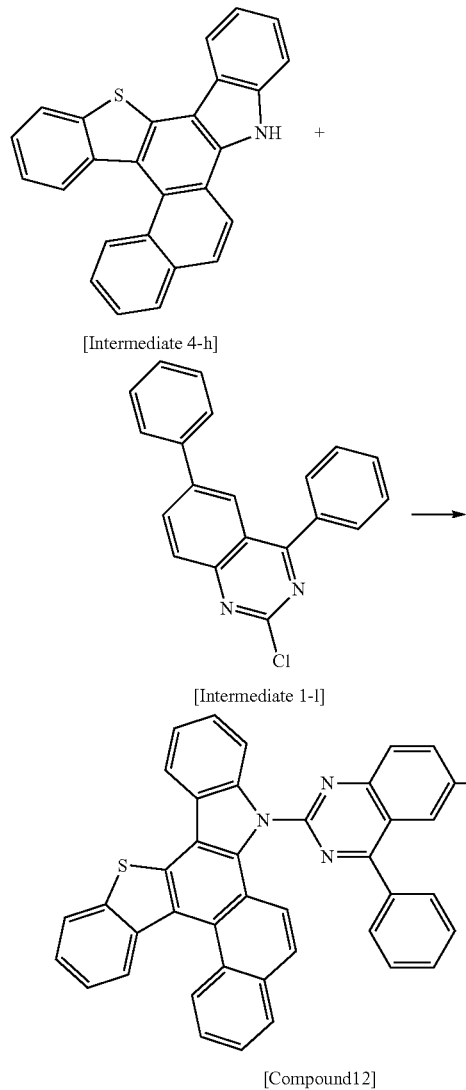

The same procedure as in Reaction Scheme 1-13 of Synthesis Example 1 was carried out, with the exception of using Intermediate 4-h instead of Intermediate 1-h, to afford Compound 12 (4.3 g): yield 46%

MS (MALDI-TOF): m/z 653.19 [M]$^+$

Synthesis Example 5

Synthesis of Compound 29

[Reaction Scheme 5-1] Synthesis of [Intermediate 5-a]

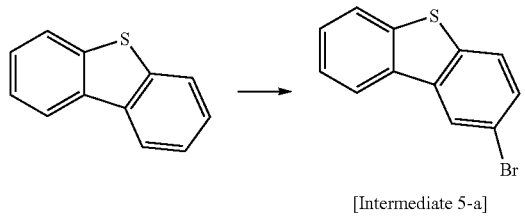 [SMILES: c1ccc2c(c1)sc1ccccc12 ; Brc1ccc2sc3ccccc3c2c1]

In a 2-L reactor, dibenzothiophene (100 g, 542 mmol) and chloroform (1 L) were stirred together under a nitrogen atmosphere and cooled to 0° C. A dilution of bromine (87 g, 542 mmol) in dichloromethane (100 ml) was slowly added in a dropwise manner, followed by stirring at room temperature for 12 hours. After the reaction was terminated with water, the organic layer was extracted and washed with an aqueous sodium hydroxide solution. The organic was condensed and recrystallized in methanol and hexane to afford the compound of Chemical Formula 5-a (74.1 g): yield 52%

[Reaction Scheme 5-2] Synthesis of [Intermediate 5-b]

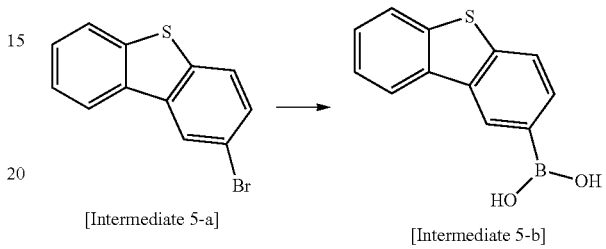

The same procedure as in Reaction Scheme 1-1 of Synthesis Example 1 was carried out, with the exception of using Intermediate 5-a instead of dibenzothiophene, to afford Intermediate 5-b (50 g): yield 78%

[Reaction Scheme 5-3] Synthesis of [Intermediate 5-c]

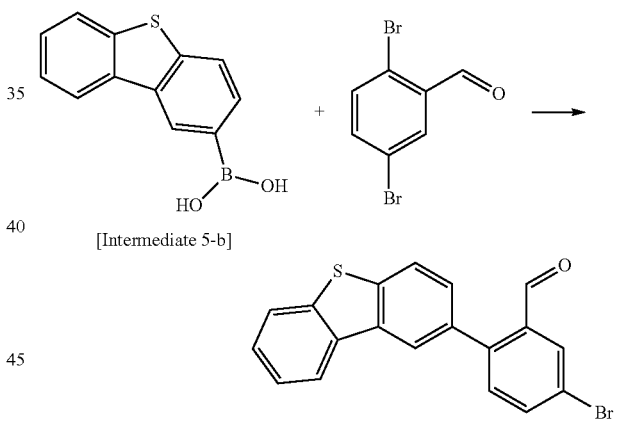

The same procedure as in Reaction Scheme 1-3 of Synthesis Example 1 was carried out, with the exception of using Intermediate 5-b and 2,5-dibromo benzaldehyde instead of Intermediate 1-a and Intermediate 1-b, respectively, to afford Intermediate 5-c (57.9 g): yield 72%

[Reaction Scheme 5-4] Synthesis of [Intermediate 5-d]

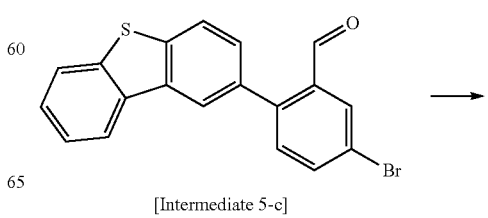

-continued

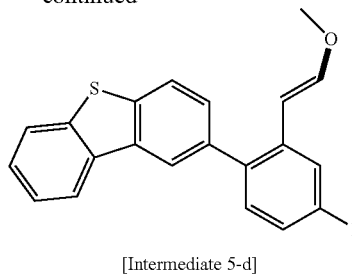

[Intermediate 5-d]

The same procedure as in Reaction Scheme 1-4 of Synthesis Example 1 was carried out, with the exception of using Intermediate 5-c instead of Intermediate 1-c, to afford Intermediate 5-d (56.7 g): yield 91%

[Reaction Scheme 5-5] Synthesis of [Intermediate 5-e]

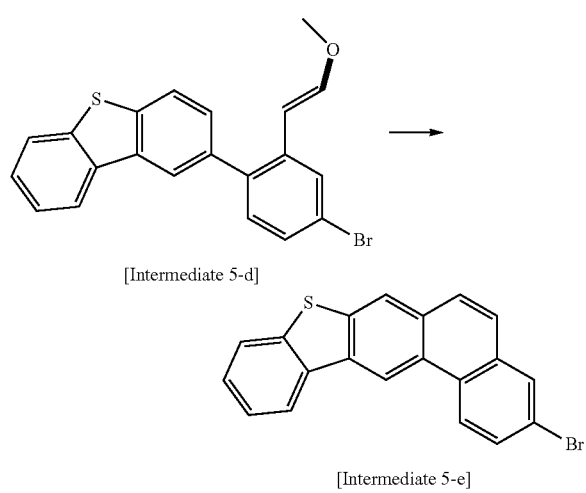

[Intermediate 5-d]

[Intermediate 5-e]

The same procedure as in Reaction Scheme 1-5 of Synthesis Example 1 was carried out, with the exception of using Intermediate 5-d instead of Intermediate 1-d, to afford Intermediate 5-e (44.8 g): yield 86%

[Reaction Scheme 5-6] Synthesis of [Intermediate 5-f]

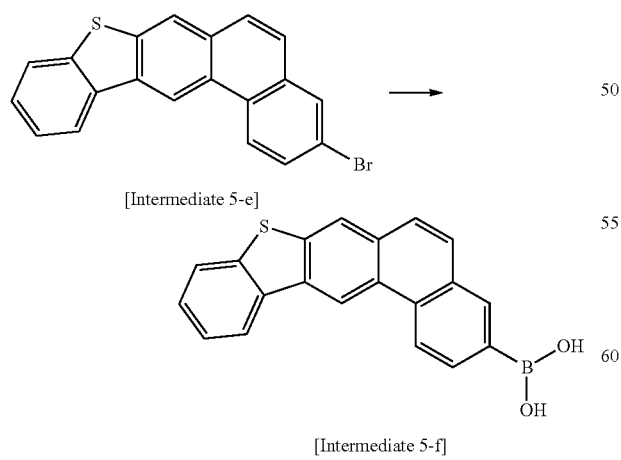

[Intermediate 5-e]

[Intermediate 5-f]

The same procedure as in Reaction Scheme 1-1 of Synthesis Example 1 was carried out, with the exception of using Intermediate 5-e instead of dibenzothiophene, to afford Intermediate 5-f (36.6 g): yield 81%

[Reaction Scheme 5-7] Synthesis of [Intermediate 5-g]

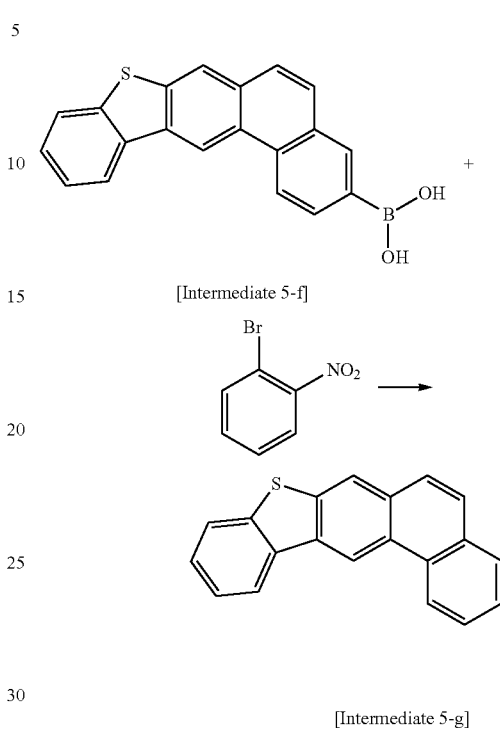

[Intermediate 5-f]

[Intermediate 5-g]

The same procedure as in Reaction Scheme 1-7 of Synthesis Example 1 was carried out, with the exception of using Intermediate 5-f instead of Intermediate 1-f, to afford Intermediate 5-g (19.7 g): yield 71%

[Reaction Scheme 5-8] Synthesis of [Intermediate 5-h]

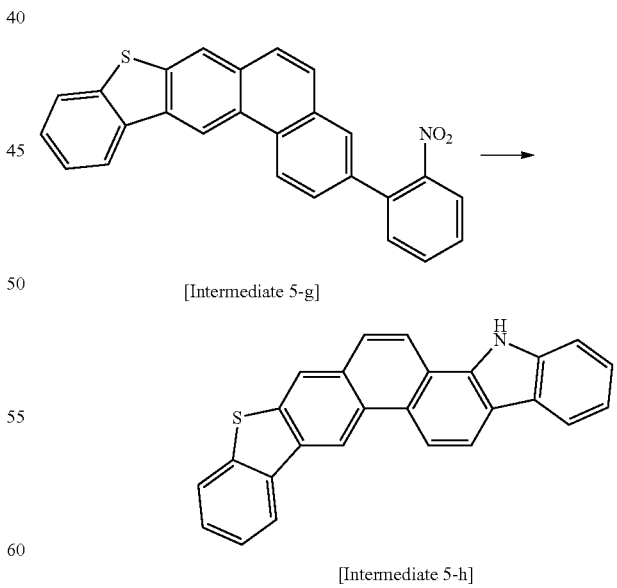

[Intermediate 5-g]

[Intermediate 5-h]

The same procedure as in Reaction Scheme 1-8 of Synthesis Example 1 was carried out, with the exception of using Intermediate 5-g instead of Intermediate 1-g], to afford Intermediate 5-h (9.4 g): yield 52%

[Reaction Scheme 5-9] Synthesis of [Compound 29]

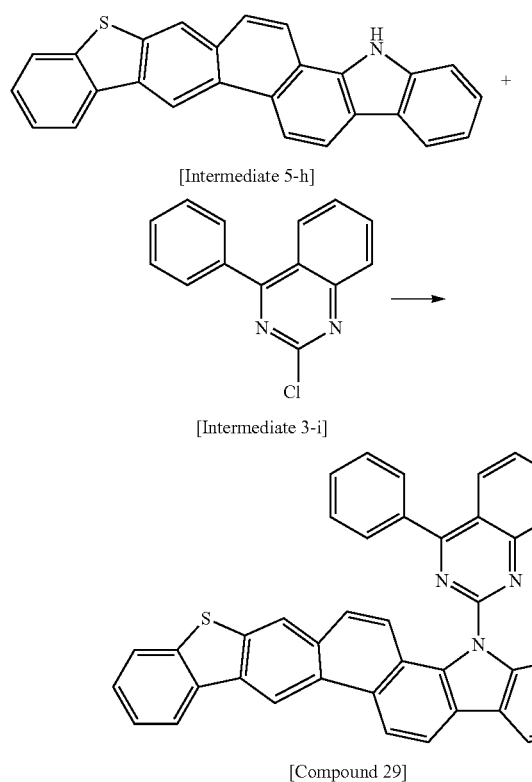

The same procedure as in Reaction Scheme 3-10 of Synthesis Example 3 was carried out, with the exception of using Intermediate 5-h instead of Intermediate 3-g, to afford Compound 29 (4.6 g): yield 48.2%

MS (MALDI-TOF): m/z 577.16 [M]$^+$

Synthesis Example 6

Synthesis of Compound 43

[Reaction Scheme 6-1] Synthesis of [Intermediate 6-a]

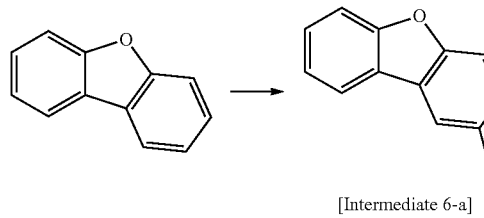

The same procedure as in Reaction Scheme 5-1 of Synthesis Example 5 was carried out, with the exception of using dibenzofuran instead of dibenzothiophene, to afford Intermediate 6-a (69 g): yield 53%

[Reaction Scheme 6-2] Synthesis of [Intermediate 6-b]

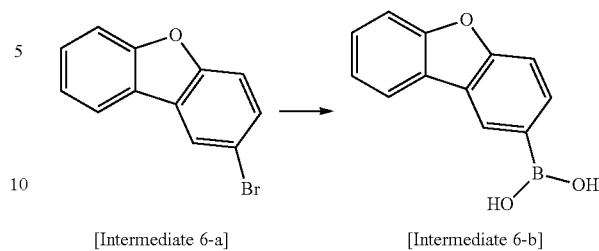

The same procedure as in Reaction Scheme 5-2 of Synthesis Example 5 was carried out, with the exception of using Intermediate 6-a instead of Intermediate 5-a, to afford Intermediate 6-b (47.2 g): yield 79%

[Reaction Scheme 6-3] Synthesis of [Intermediate 6-c]

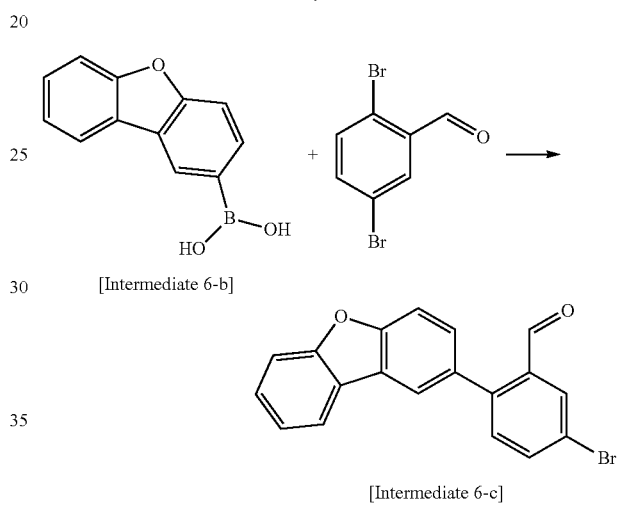

The same procedure as in Reaction Scheme 5-3 of Synthesis Example 5 was carried out, with the exception of using Intermediate 6-b instead of Intermediate 5-b, to afford Intermediate 6-c (36.5 g): yield 63%

[Reaction Scheme 6-4] Synthesis of [Intermediate 6-d]

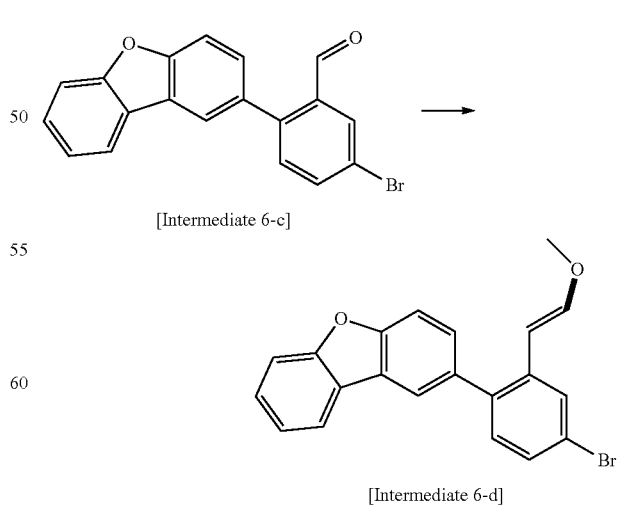

The same procedure as in Reaction Scheme 1-4 of Synthesis Example 1 was carried out, with the exception of using Intermediate 6-c instead of Intermediate 1-c, to afford Intermediate 6-d (33.9 g): yield 83%

[Reaction Scheme 6-5] Synthesis of [Intermediate 6-e]

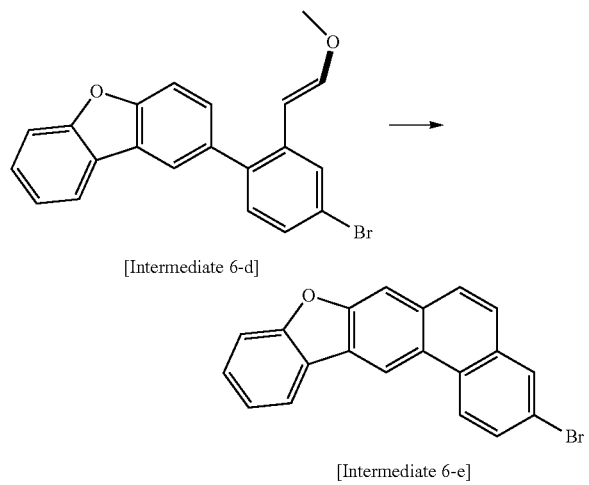

The same procedure as in Reaction Scheme 1-5 of Synthesis Example 1 was carried out, with the exception of using Intermediate 6-d, instead of Intermediate 1-d, to afford Intermediate 6-e (24.8 g): yield 79%

[Reaction Scheme 6-6] Synthesis of [Intermediate 6-f]

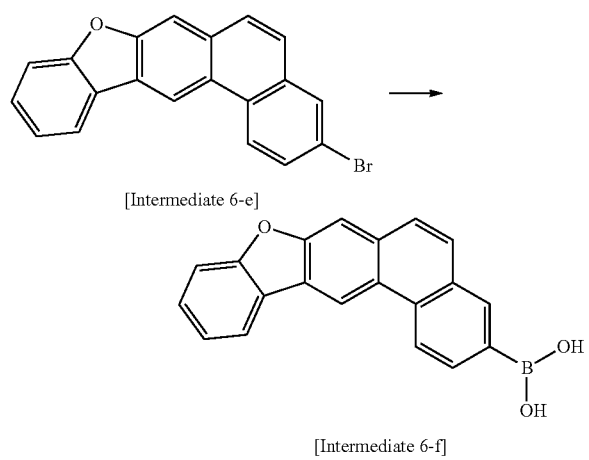

The same procedure as in Reaction Scheme 5-2 of Synthesis Example 5 was carried out, with the exception of using Intermediate 6-e instead of Intermediate 5-a, to afford Intermediate 6-f (18.2 g): yield 81%

[Reaction Scheme 6-7] Synthesis of [Intermediate 6-g]

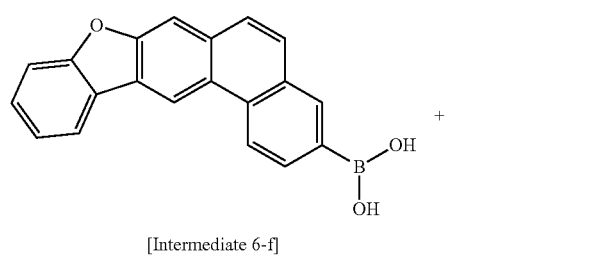

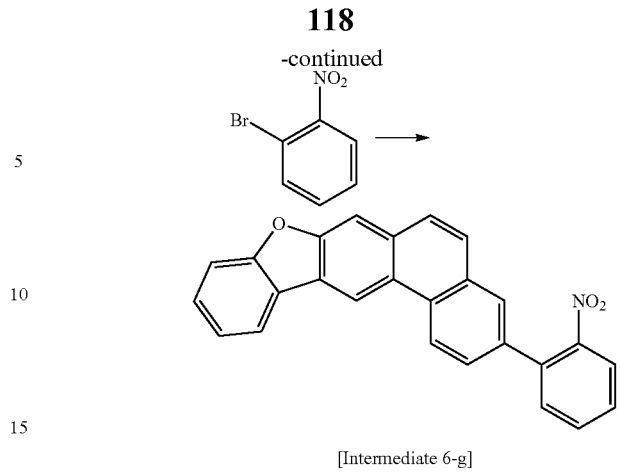

The same procedure as in Reaction Scheme 1-7 of Synthesis Example 1 was carried out, with the exception of using Intermediate 6-f instead of Intermediate 1-f, to afford Intermediate 6-g (15.1 g): yield 68%

[Reaction Scheme 6-8] Synthesis of [Intermediate 6-h]

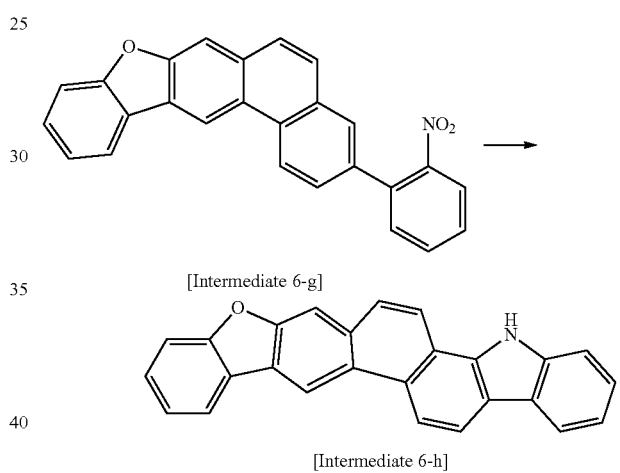

The same procedure as in Reaction Scheme 1-8 of Synthesis Example 1 was carried out, with the exception of using Intermediate 6-g instead of Intermediate 1-g, to afford Intermediate 6-h (7.3 g): yield 52%

[Reaction Scheme 6-9] Synthesis of [Compound 43]

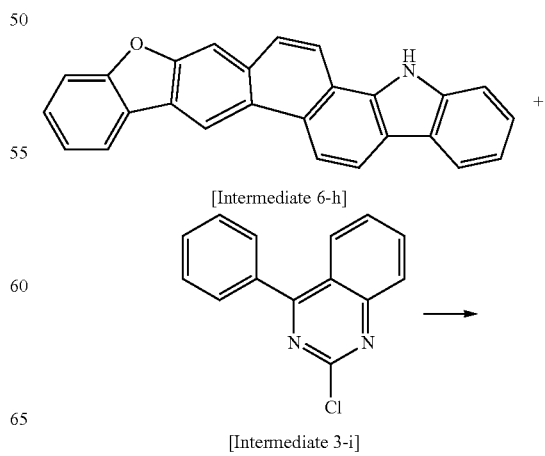

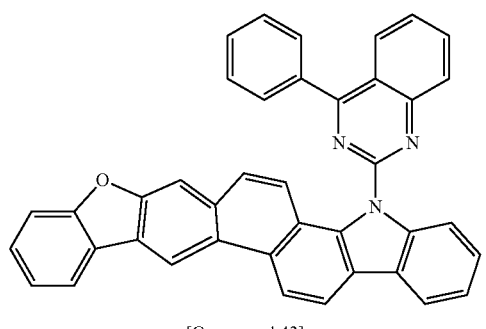

[Compound 43]

The same procedure as in Reaction Scheme 3-10 of Synthesis Example 3 was carried out, with the exception of using Intermediate 6-h instead of Intermediate 3-g, to afford Compound 43 (4.8 g): yield 48.1%

MS (MALDI-TOF): m/z 561.18 [M]$^+$

Synthesis Example 7

Synthesis of Compound 44

[Reaction Scheme 7-1] Synthesis of [Intermediate 7-a]

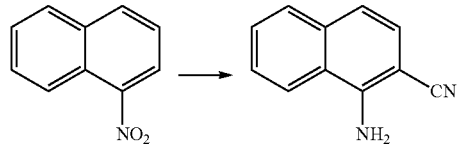

[Intermediate 7-a]

In a 2-L reactor, ethyl cyanoacetate (139.8 g, 1.236 mol), potassium cyanide (29.5 g, 0.453 mol), and potassium hydroxide (46.2 g, 0.824 mol) were dissolved together in dimethylformamide (920 mL) and then stirred at 10° C. for 20 min. To the reactants was added 1-nitronaphthalene (92 g, 412 mol), followed by stirring at 60° C. for 4 hours. The solvent was concentrated and an aqueous 10% sodium hydroxide solution (600 mL) was added before stirring under reflux for one hour. Following filtration, purification by column chromatography afforded the compound of Chemical Formula 7-a as a solid (50 g): yield 60%

[Reaction Scheme 7-2] Synthesis of [Intermediate 7-b]

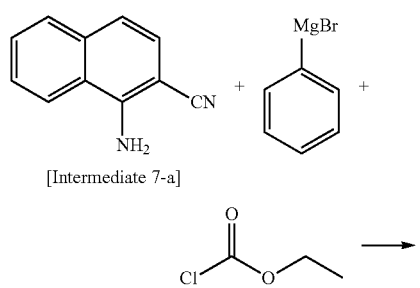

[Intermediate 7-a]

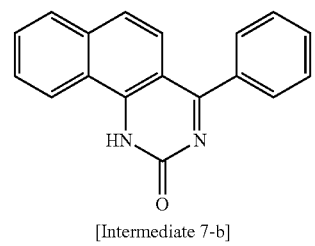

[Intermediate 7-b]

The same procedure as in Reaction Scheme 1-11 of Synthesis Example 1 was carried out, with the exception of using Intermediate 7-a instead of Intermediate 1-j, to afford Intermediate 7-b (50 g): yield 60%)

[Reaction Scheme 7-3] Synthesis of [Intermediate 7-c]

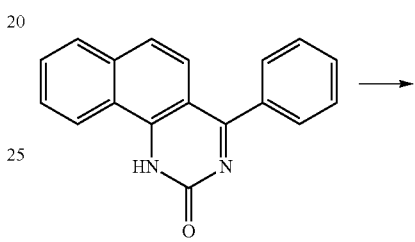

[Intermediate 7-b]

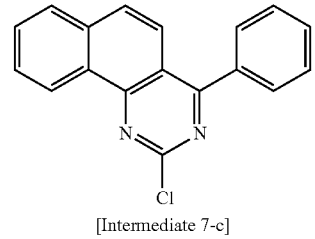

[Intermediate 7-c]

The same procedure as in Reaction Scheme 1-12 of Synthesis Example 1 was carried out, with the exception of using Intermediate 7-b instead of Intermediate 1-k, to afford Intermediate 7-c (29.3 g): yield 66%)

[Reaction Scheme 7-4] Synthesis of [Compound 44]

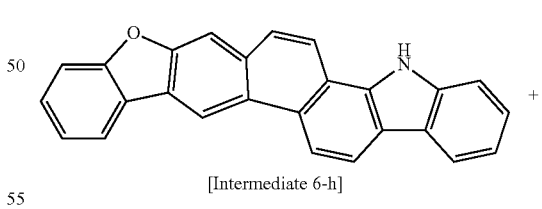

[Intermediate 6-h]

+

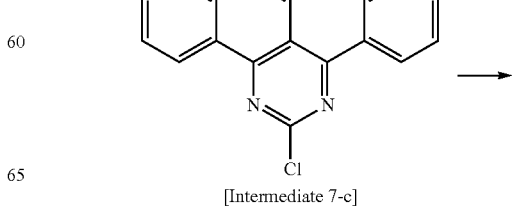

[Intermediate 7-c]

-continued

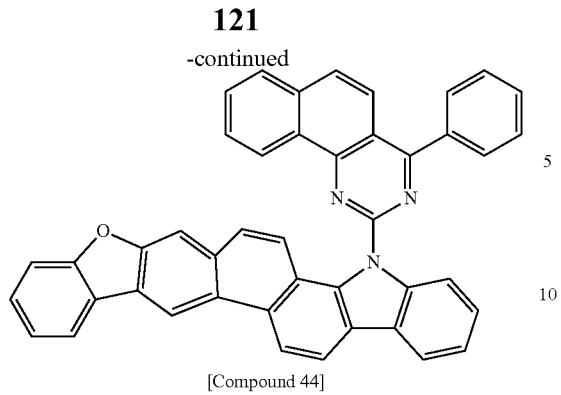

[Compound 44]

The same procedure as in Reaction Scheme 1-13 of Synthesis Example 1 was carried out, with the exception of using Intermediate 6-h and Intermediate 7-c instead of Intermediate 1-h and Intermediate 1-l, respectively, to afford Compound 44 (4.1 g): yield 36.3%

MS (MALDI-TOF): m/z 611.20 [M]$^+$

Synthesis Example 8

Synthesis of Compound 49

[Reaction Scheme 8-1] Synthesis of Intermediate 8-a

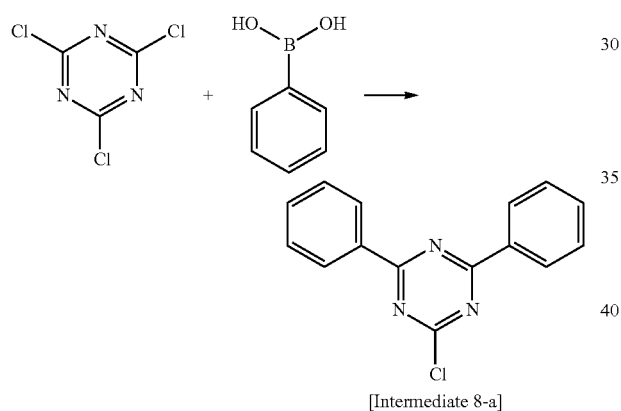

[Intermediate 8-a]

The same procedure as in Reaction Scheme 1-13 of Synthesis Example 1 was carried out, with the exception of using cyanuric chloride and phenyl boronic acid instead of Intermediate 1-h and Intermediate 1-l, respectively, to afford Intermediate 8-a (28 g): yield 48%

[Reaction Scheme 8-2] Synthesis of Compound 49

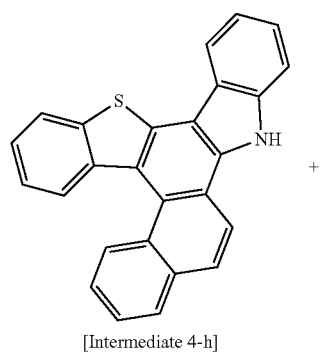

[Intermediate 4-h]

-continued

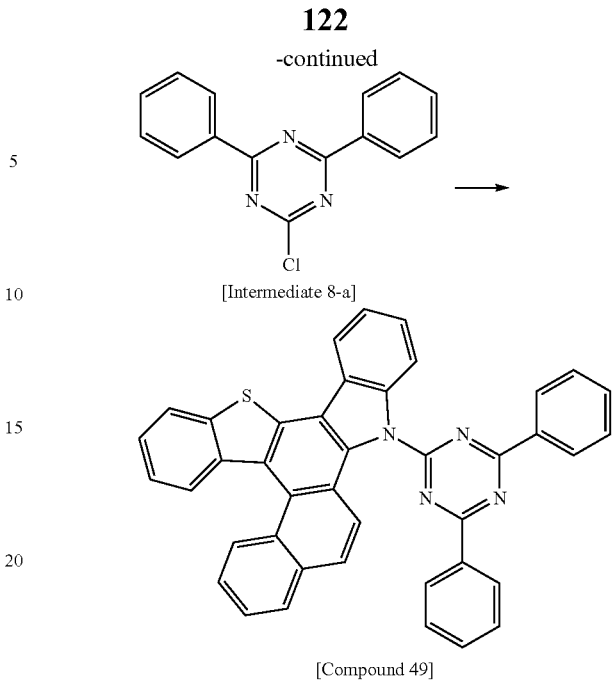

[Compound 49]

The same procedure as in Reaction Scheme 1-13 of Synthesis Example 1 was carried out, with the exception of using Intermediate 4-h and Intermediate 8-a instead of Intermediate 1-h and Intermediate 1-l, respectively, to afford Compound 49 (5.1 g): yield 39.5%

MS (MALDI-TOF): m/z 604.17 [M]$^+$

Synthesis Example 9

Synthesis of Compound 65

[Reaction Scheme 9-1] Synthesis of [Intermediate 9-a]

[Intermediate 9-a]

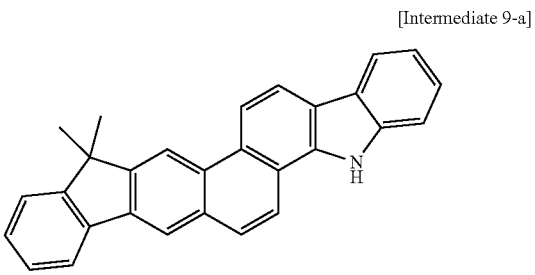 [SMILES: CC1(C)c2ccccc2-c2cc3ccc4c(ccc5c6ccccc6[nH]c54)c3cc21]

The same procedure as in Synthesis Example 5 was carried out, with the exception of using 2-bromo-9,9-dimethylfluorene instead of 2-bromo dibenzothiophene, to afford Intermediate 9-a (4.3 g): yield 47%

[Reaction Scheme 9-2] Synthesis of Compound 65

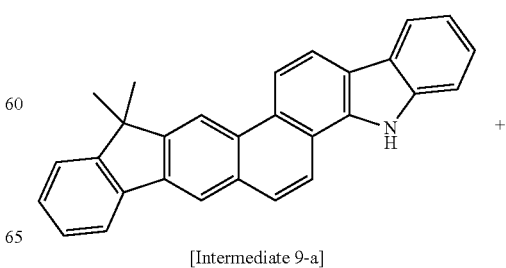

[Intermediate 9-a]

-continued

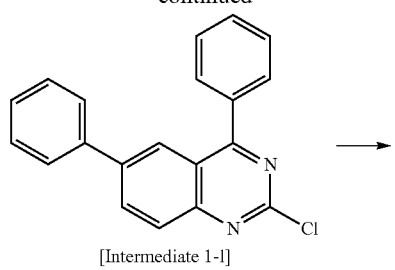
[Intermediate 1-l]

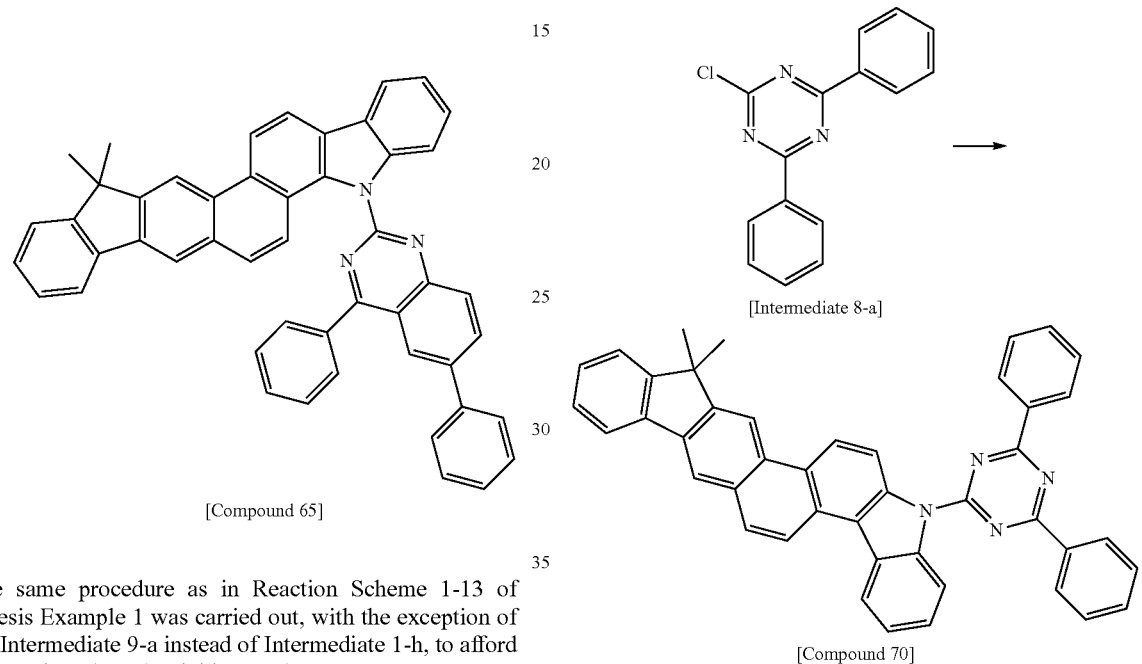
[Compound 65]

The same procedure as in Reaction Scheme 1-13 of Synthesis Example 1 was carried out, with the exception of using Intermediate 9-a instead of Intermediate 1-h, to afford Compound 65 (5.4 g): yield 34.3%)

MS (MALDI-TOF): m/z 663.27 [M]+

Synthesis Example 10

Synthesis of Compound 70

[Reaction Scheme 10-1] Synthesis of [Intermediate 10-a]

[Intermediate 10-a]

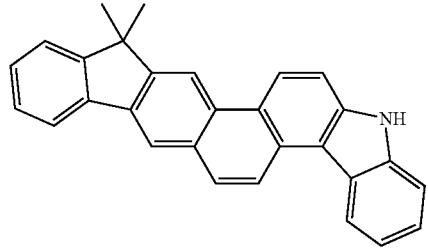

The same procedure as in Synthesis Example 1 was carried out, with the exception of using 2-bromo-9,9-dimethylfluorene instead of dibenzothiophene, to afford Intermediate 10-a (3.9 g): yield 55%

[Reaction Scheme 10-2] Synthesis of Compound 70

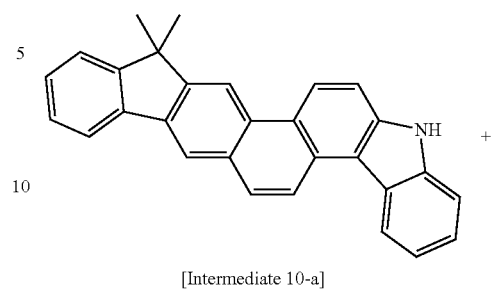
[Intermediate 10-a]

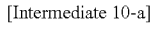
[Intermediate 8-a]

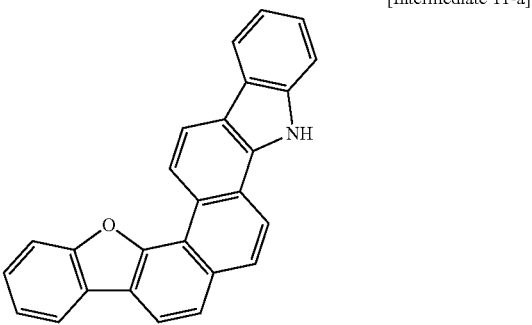
[Compound 70]

The same procedure as in Reaction Scheme 8-2 of Synthesis Example 8 was carried out, with the exception of using Intermediate 10-a instead of Intermediate 4-h, to afford Compound 70 (4.4 g): yield 35.9%

MS (MALDI-TOF): m/z 614.25 [M]+

Synthesis Example 11

Synthesis of Compound 74

[Reaction Scheme 11-1] Synthesis of [Intermediate 11-a]

[Intermediate 11-a]

The same procedure as in Synthesis Example 2 was carried out, with the exception of using dibenzofuran instead of dibenzothiophene, to afford Intermediate 11-a (4.9 g): yield 37.2%

[Reaction Scheme 11-2] Synthesis of [Compound 74]

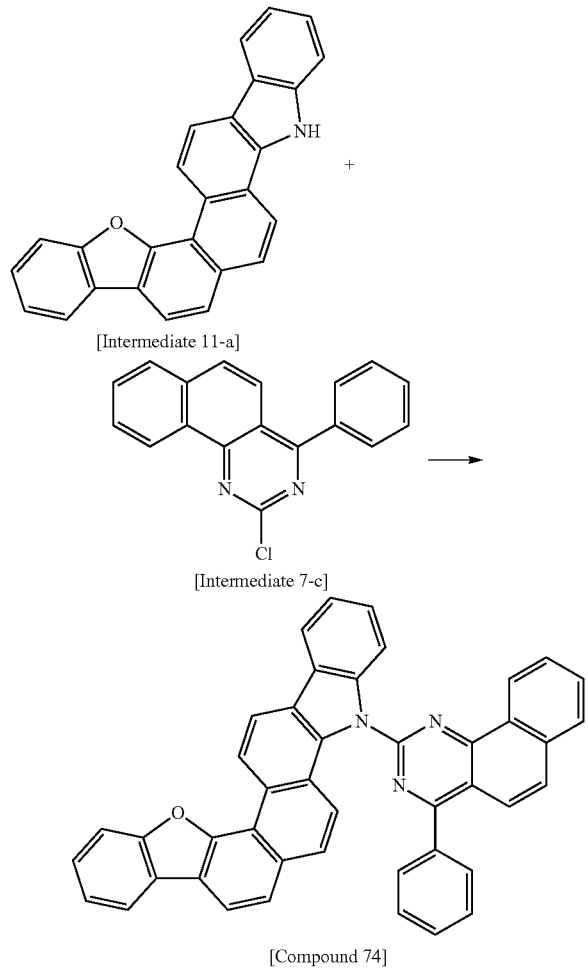

The same procedure as in Reaction Scheme 7-4 of Synthesis Example 7 was carried out, with the exception of using Intermediate 11-a instead of Intermediate 6-h, to afford Compound 74 (4.9 g): yield 37.2%
MS (MALDI-TOF): m/z 611.20 [M]$^+$ Synthesis Example 12

Synthesis of Compound 76

Synthesis Example 12-1 Synthesis of Intermediate 12-a

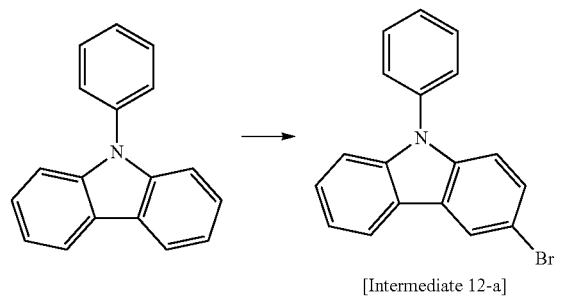 [SMILES: c1ccc(-n2c3ccccc3c3ccccc32)cc1 ; Brc1ccc2c(c1)c1ccccc1n2-c1ccccc1]

In a 1-L reactor, 9-phenyl carbazole (50 g, 205 mmol), N-bromosuccinimide (36.5 g, 205 mmol), toluene (700 ml), and ethylacetate (300 ml) were placed and stirred together at room temperature for 45 hours. After completion of the reaction, the organic layer was extracted and concentrated at a reduced pressure. Purification by column chromatography afforded Intermediate 12-a (60.7 g): yield 92%

Synthesis Example 12-2 Synthesis of Intermediate 12-b

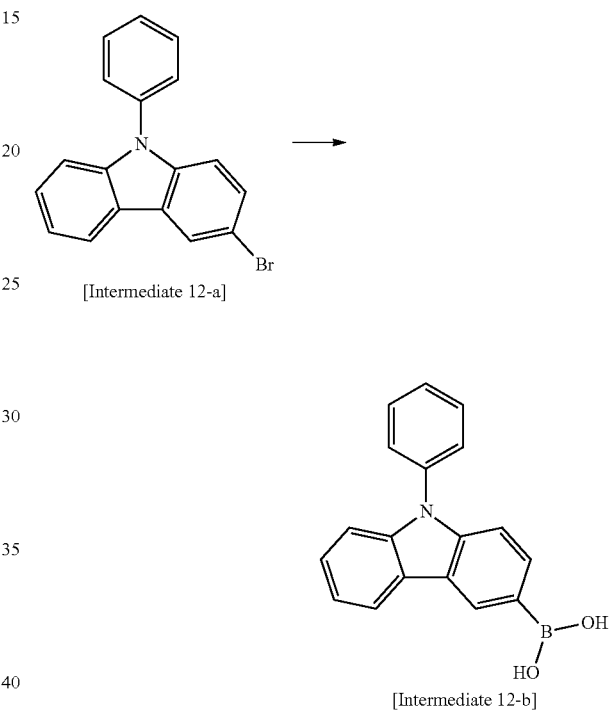

The same procedure as in Reaction Scheme 1-1 of Synthesis Example 1 was carried out, with the exception of using Intermediate 12-a instead of dibenzothiophene, to afford Intermediate 12-b (39.5 g): yield 74%

Synthesis Example 12-3 Synthesis of Intermediate 12-c

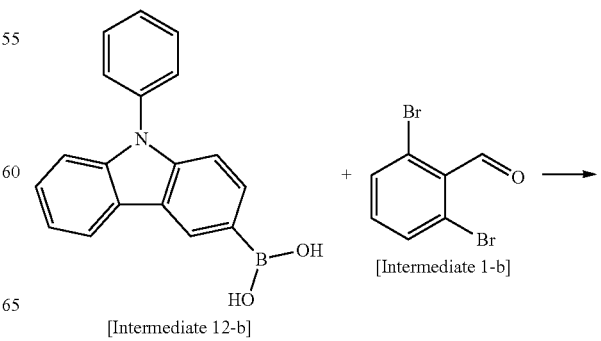

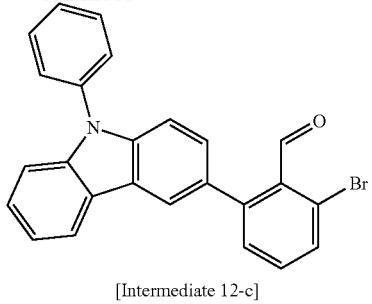

[Intermediate 12-c]

The same procedure as in Reaction Scheme 1-3 of Synthesis Example 1 was carried out, with the exception of using Intermediate 12-b instead of Intermediate 1-b, to afford Intermediate 12-c (39.3 g): yield 67%

Synthesis Example 12-4 Synthesis of Intermediate 12-d

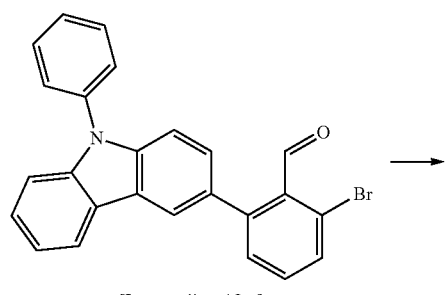

[Intermediate 12-c]

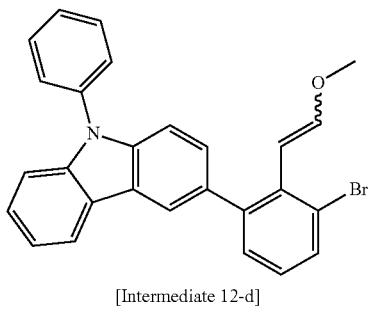

[Intermediate 12-d]

The same procedure as in Reaction Scheme 1-4 of Synthesis Example 1 was carried out, with the exception of using Intermediate 12-c instead of Intermediate 1-c, to afford Intermediate 12-d (35.6 g): yield 85%

Synthesis Example 12-5 Synthesis of Intermediate 12-e

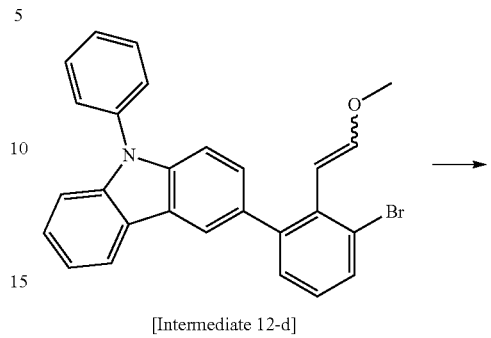

[Intermediate 12-d]

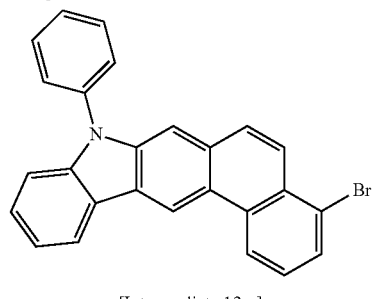

[Intermediate 12-e]

The same procedure as in Reaction Scheme 1-5 of Synthesis Example 1 was carried out, with the exception of using Intermediate 12-d instead of Intermediate 1-d, to afford Intermediate 12-e (27.2 g): yield 79%

Synthesis Example 12-6 Synthesis of Intermediate 12-f

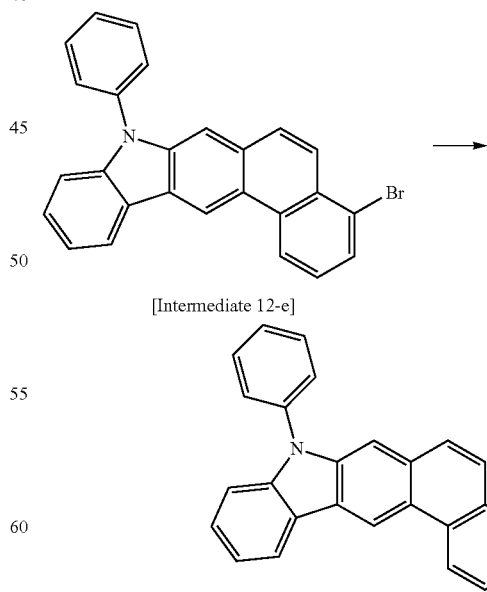

[Intermediate 12-e]

[Intermediate 12-f]

The same procedure as in Reaction Scheme 1-1 of Synthesis Example 1 was carried out, with the exception of using Intermediate 12-e instead of dibenzothiophene, to afford Intermediate 12-f (19.7 g): yield 82%

Synthesis Example 12-7 Synthesis of Intermediate 12-g

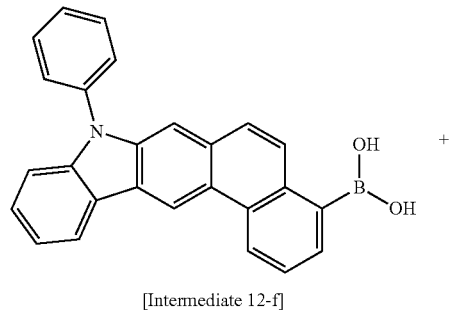

[Intermediate 12-f]

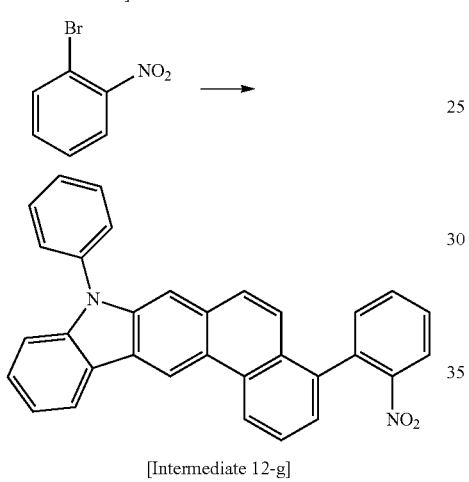

[Intermediate 12-g]

The same procedure as in Reaction Scheme 1-7 of Synthesis Example 1 was carried out, with the exception of using Intermediate 12-f instead of Intermediate 1-f, to afford Intermediate 12-g (17.5 g): yield 74%

Synthesis Example 12-8 Synthesis of Intermediate 12-h

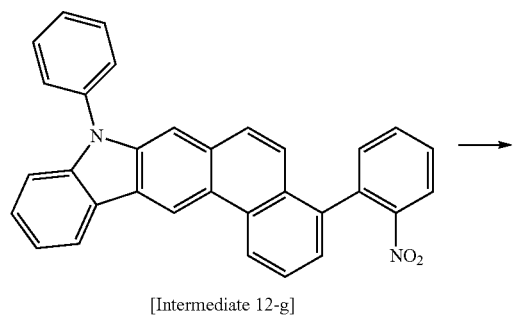

[Intermediate 12-g]

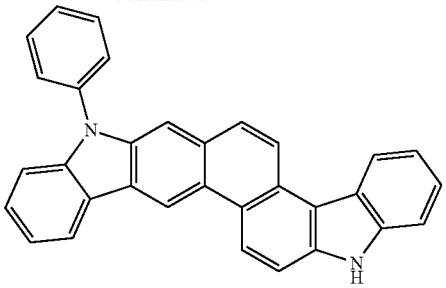

[Intermediate 12-h]

The same procedure as in Reaction Scheme 1-8 of Synthesis Example 1 was carried out, with the exception of using Intermediate 12-g instead of Intermediate 1-g, to afford Intermediate 12-h (8.4 g): yield 52%

Synthesis Example 12-9 Synthesis of Compound 76

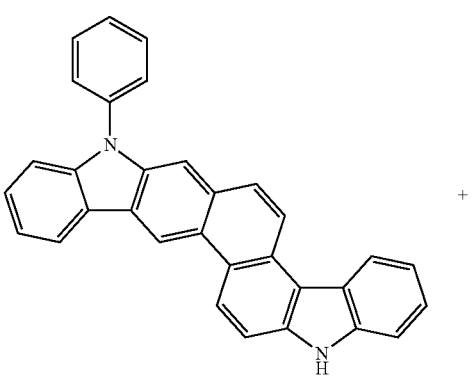

[Intermediate 12-h]

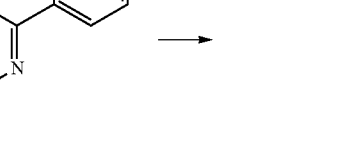

[Intermediate 3-i]

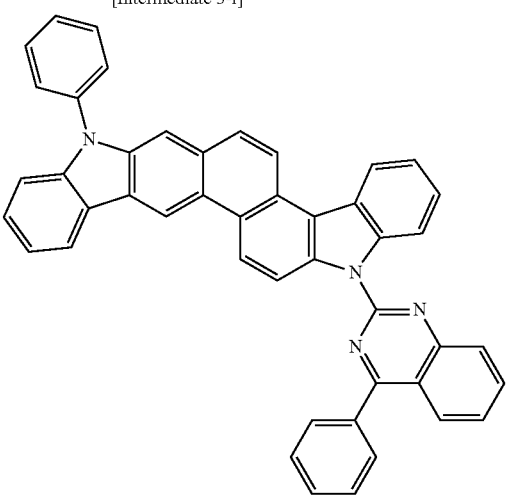

[Compound 76]

The same procedure as in Reaction Scheme 3-10 of Synthesis Example 3 was carried out, with the exception of using Intermediate 12-h instead of Intermediate 3-g, to afford Compound 76 (5.4 g): yield 34.3%

MS (MALDI-TOF): m/z 636.23 [M]$^+$

Synthesis Example13

Synthesis of Compound 77

Synthesis Example13-1 Synthesis of Intermediate 13-a

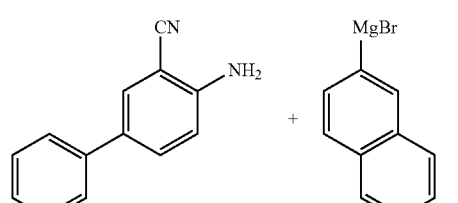

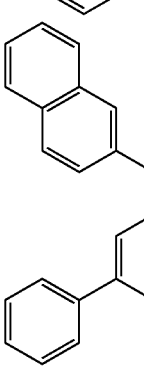

[Intermediate 13-a]

The same procedure as in Reaction Scheme 1-11 of Synthesis Example 1 was carried out, with the exception of using 2-naphthyl magnesium bromide instead of phenyl magnesium bromide, to afford Intermediate 13-a (17.1 g): yield 37%

Synthesis Example13-2 Synthesis of Intermediate 13-b

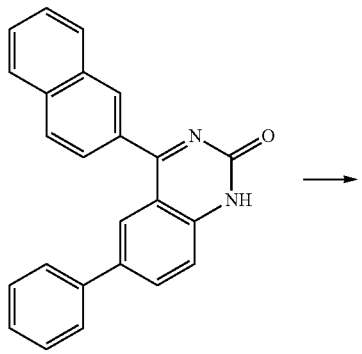

[Intermediate 13-a]

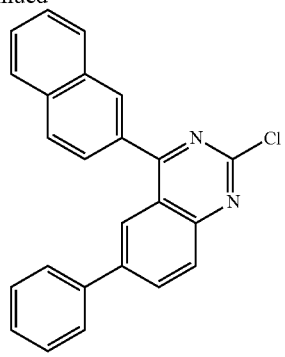

[Intermediate 13-b]

The same procedure as in Reaction Scheme 1-12 of Synthesis Example 1 was carried out, with the exception of using Intermediate 13-a instead of Intermediate 1-k, to afford Intermediate 13-b (11.3 g): yield 65%

Synthesis Example13-3 Synthesis of Intermediate 13-c

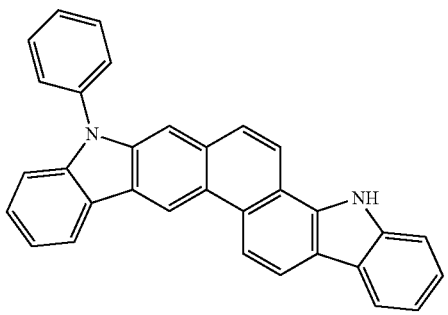

[Intermediate 13-c]

The same procedure as in Synthesis Examples 12-3 to 12-8 was carried out, with the exception of using 2, 5-dibromo benzaldehyde instead of Intermediate 1-b in Reaction Scheme 1-3 of Synthesis Example 1, to afford Intermediate 13-c (9.1 g): yield 48%

Synthesis Example13-4

Synthesis of Compound 77

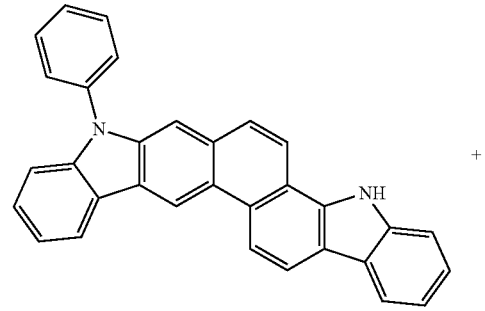

[Intermediate 13-c]

-continued

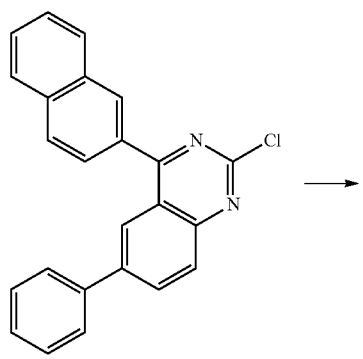

[Intermediate 13-b]

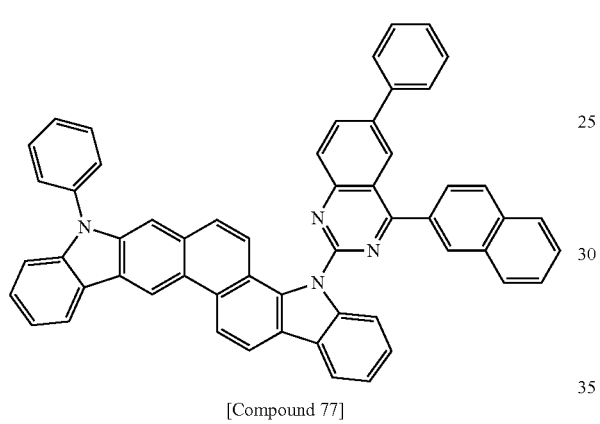

[Compound 77]

The same procedure as in Reaction Scheme 3-10 of Synthesis Example 3 was carried out, with the exception of using Intermediate 13-c and Intermediate 13-b instead of Intermediate 3-g and Intermediate 1-l, respectively, to afford Compound 77 (3.5 g): yield 41.3%

MS (MALDI-TOF): m/z 762.28 [M]$^+$

Synthesis Example14

Synthesis of Compound 89

Synthesis Example14-1Synthesis of Compound 89

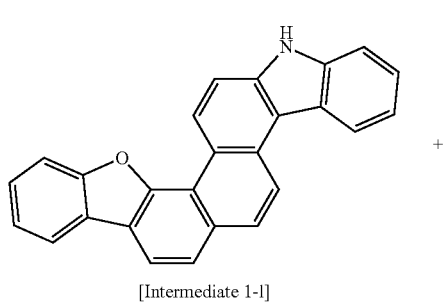 +

[Intermediate 1-l]

-continued

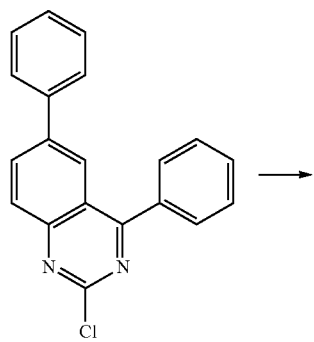

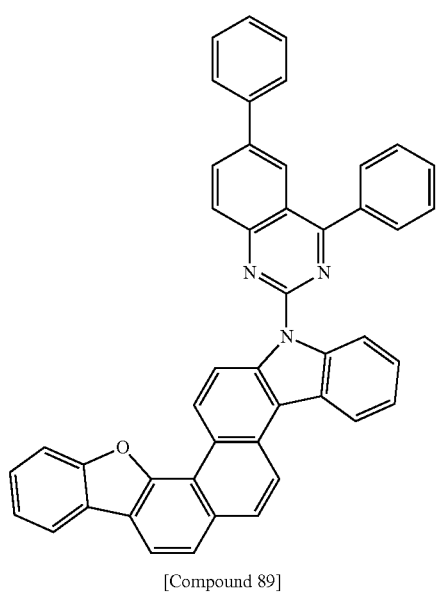

[Compound 89]

The same procedure as in Synthesis Example 1 was carried out, with the exception of using dibenzofuran instead of dibenzothiophene, to afford Compound 89 (4.4 g): yield 38.2%

MS (MALDI-TOF): m/z 637.22 [M]$^+$

Synthesis Example 15

Synthesis of Compound 104

Synthesis Example15-1Synthesis of Compound104

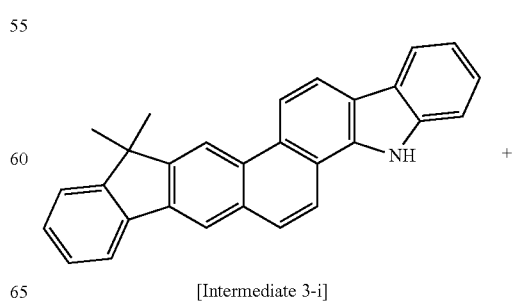 +

[Intermediate 3-i]

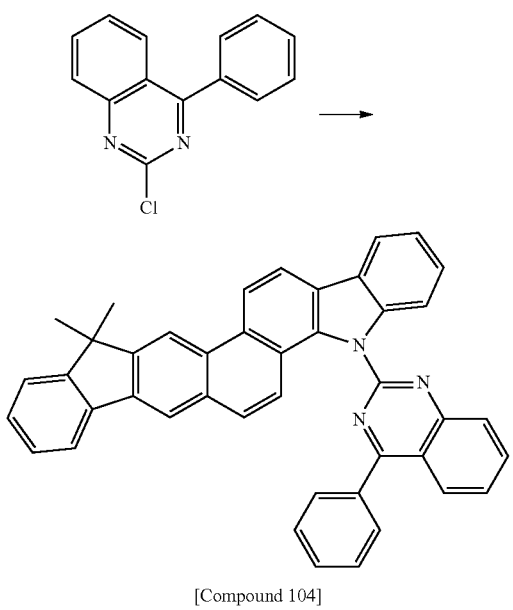

[Compound 104]

The same procedure as in Reaction Scheme 9-2 of Synthesis Example 9 was carried out, with the exception of using Intermediate 3-i instead of Intermediate 1-l, to afford Compound 104 (5.1 g): yield 41.5%

MS (MALDI-TOF): m/z 587.24 [M]$^+$

Examples: Fabrication of Organic Light-Emitting Device

An ITO glass substrate was patterned to have a translucent area of 2 mm×2 mm and cleansed. The ITO glass was mounted in a vacuum chamber that was then set to have a base pressure of 1×10$^6$ torr. On the ITO glass substrate, films were formed of organic compounds in the order of DNTPD (700 Å), α-NPB (300 Å), compounds prepared according to the present invention+RD-1 (10%) (300 Å), Compound E: Liq=1:1 (250 Å), Liq (10 Å), and Al (1,000 Å). The light-emitting devices thus obtained were measured at 0.4 mA for luminescence properties.

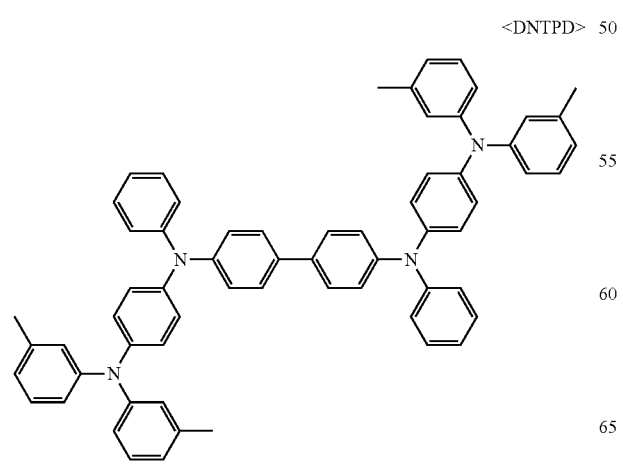

<DNTPD>

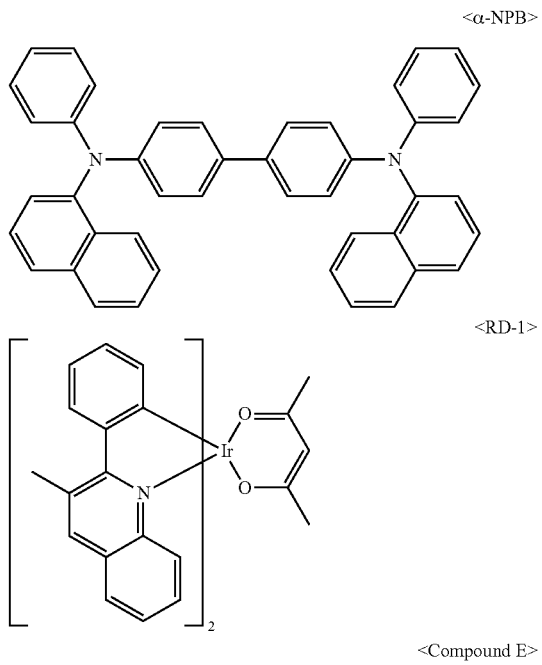

<α-NPB>

<RD-1>

<Compound E>

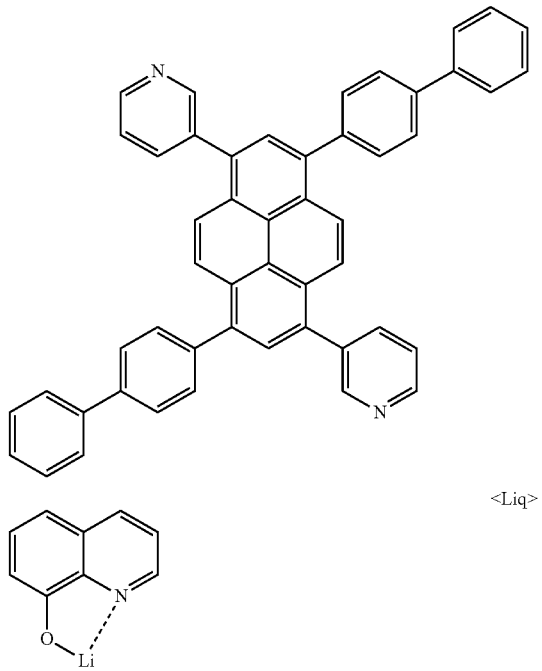

<Liq>

Comparative Example

An organic light-emitting device in the Comparison Example was fabricated in the same manner as in that of the Examples, with the exception that BAlq, a typically used phosphorescent light-emitting host material, was used instead of the compounds prepared according to the present invention. The structure of BAlq is as follows:

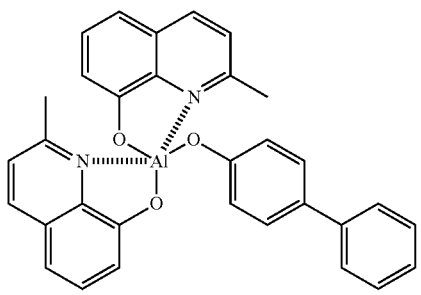

<BAlq>

The organic EL devices fabricated in the Examples 1 to 15 and Comparative Example 1 were measured for voltage, current density, luminance, color coordinates, and lifespan, and the results are summarized in Table 1, below. Here, T95 refers to the time for luminance to decrease to 95% of the initial luminance (3000 cd/m$^2$).

TABLE 1

| Example | Host | V | Cd/m$^2$ | CIEx | CIEy | T$_{95}$ (Hr) |
|---|---|---|---|---|---|---|
| C. Ex. 1 | BAlq | 6.2 | 1510 | 0.665 | 0.334 | 45 |
| Ex. 1 | 1 | 5.0 | 1880 | 0.661 | 0.338 | 160 |
| Ex. 2 | 3 | 4.8 | 1760 | 0.663 | 0.336 | 150 |
| Ex. 3 | 6 | 4.7 | 1850 | 0.664 | 0.334 | 140 |
| Ex. 4 | 12 | 4.6 | 1690 | 0.665 | 0.335 | 130 |
| Ex. 5 | 29 | 4.7 | 1870 | 0.663 | 0.336 | 140 |
| Ex. 6 | 43 | 4.6 | 1900 | 0.663 | 0.336 | 140 |
| Ex. 7 | 44 | 4.8 | 1860 | 0.663 | 0.336 | 150 |
| Ex. 8 | 49 | 4.2 | 1910 | 0.660 | 0.338 | 160 |
| Ex. 9 | 65 | 4.8 | 1860 | 0.664 | 0.335 | 140 |
| Ex. 10 | 70 | 4.4 | 1880 | 0.662 | 0.337 | 130 |
| Ex. 11 | 74 | 4.8 | 1900 | 0.661 | 0.338 | 140 |
| Ex. 12 | 76 | 4.3 | 1860 | 0.663 | 0.336 | 150 |
| Ex. 13 | 77 | 4.2 | 1780 | 0.662 | 0.337 | 130 |
| Ex. 14 | 89 | 4.7 | 1970 | 0.660 | 0.338 | 150 |
| Ex. 15 | 104 | 4.7 | 1670 | 0.661 | 0.338 | 140 |

As is understood from data of Table 1, organic electroluminescent devices including the organic light-emitting compounds according to the present invention exhibit lower driving voltage, higher luminescence efficiency, and longer lifespan, compared to that including the typical host material BAlq.

INDUSTRIAL APPLICABILITY

When used as a phosphorescent host, the organic compounds according to the present invention have characteristics of long lifespan, low voltage driving, and outstanding luminance efficiency. Finding applications in the fabrication of stable and excellent devices, thus, the present invention is industrially applicable.

The invention claimed is:

1. An organic light-emitting compound, represented by the following Chemical Formula A:

[Chemical Formula A]

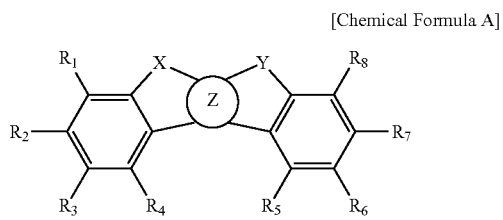

-continued

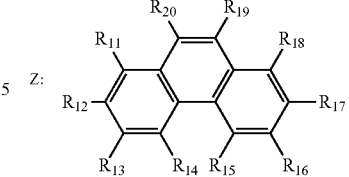

Z:

wherein, the substituents R$_1$ to R$_8$, and R$_{11}$ to R$_{20}$, which may be the same or different, are each independently any one selected from among a hydrogen, a deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted arylthioxy of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkylgermanium of 1 to 30 carbon atoms, a substituted or unsubstituted of 1 to 30 carbon atoms arylgermanium, a cyano, a nitro, and a halogen;

Z is a substituted or unsubstituted phenanthrene ring wherein two adjacent radicals selected from among R$_{11}$ to R$_{20}$ are respective single bonds involved in forming a 5-membered, fused ring bearing X in Chemical Formula A;

two other adjacent radicals from among R$_{11}$ to R$_{20}$ are respective single bonds involved in forming a 5-membered, fused ring bearing Y in Chemical Formula A;

X and Y may be the same or different and are each be any one selected from among CR$_{21}$R$_{22}$, S, O, and NR$_{23}$;

wherein the substituents R$_{21}$ to R$_{22}$ are defined as for R$_1$ to R$_8$, and in Chemical Formula A, at least one of X and Y is NR$_{23}$ and wherein R$_{23}$ is any one heteroaryl selected from among the following Structural Formulas B, C, E, F, M, N, and O:

[Structural Formula B]

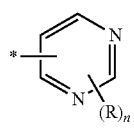

[Structural Formula C]

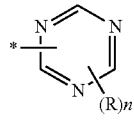

[Structural Formula E]

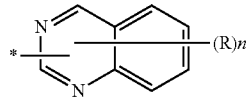

[Structural Formula F]

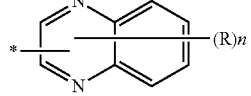

-continued

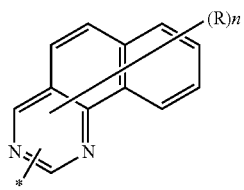
[Structural Formula M]

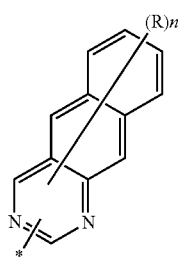
[Structural Formula N]

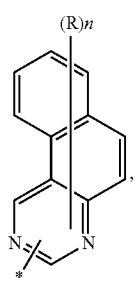
[Structural Formula O]

wherein the substituent R of Structural Formulas B, C, E, F, M, N, and O is as defined for $R_1$ to $R_8$ and may be connected to an adjacent one to form a saturated or unsaturated ring, and, n is an integer of 1 to 7, wherein the term 'substituted' in the expression "substituted or unsubstituted" means having at least one substituent selected from the group consisting of a deuterium, a cyano, a halogen, a nitro, an alkyl of 1 to 24 carbon atoms, an halogenated alkyl of 1 to 24 carbon atoms, an aryl of 6 to 24 carbon atoms, an arylalkyl of 6 to 24 carbon atoms, a heteroaryl of 2 to 24 carbon atoms or a heteroarylalkyl of 2 to 24 carbon atoms, an alkylsilyl of 1 to 24 carbon atoms, and an arylsilyl of 6 to 24 carbon atoms.

2. The organic light-emitting compound of claim 1, wherein $R_{23}$ is a substituent represented by any one of the following Structural Formulas A-1 to E-1:

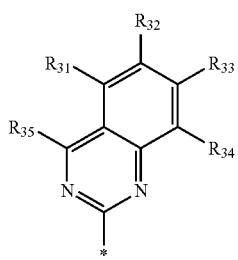
[Structural Formula A-1]

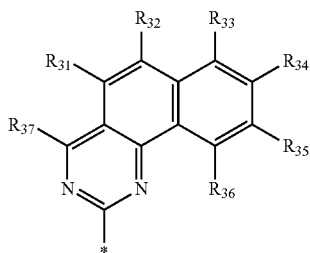
[Structural Formula B-1]

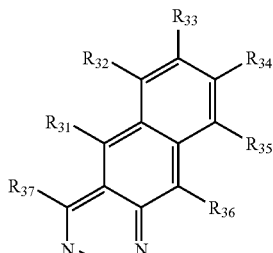
[Structural Formula C-1]

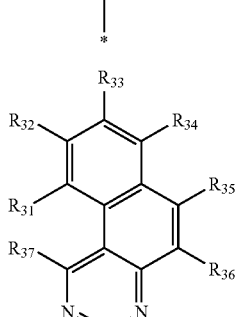
[Structural Formula D-1]

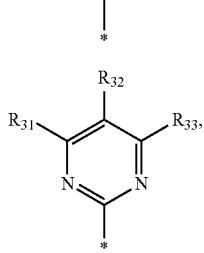
[Structural Formula E-1]

wherein, the substituents R31 to R37, which may be the same or different, are each independently any one selected from among a hydrogen, a deuterium, a substituted or unsubstituted alkyl of 1 to 30 carbon atoms, a substituted or unsubstituted aryl of 5 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 5 to 30 carbon atoms, a substituted or unsubstituted a substituted or unsubstituted heteroaryl of 2 to 50 carbon atoms bearing O, N, or S as a heteroatom, a cyano, a nitro, and a halogen.

3. The organic light-emitting compound of claim 1, wherein Z is a substituted or unsubstituted phenanthrene ring in which two adjacent substituents selected from among $R_{11}$ to $R_{14}$ are respective single bonds participating together in the formation of a fused ring as a 5-membered ring bearing X and two adjacent substituents selected from among $R_{15}$ to $R_{18}$ are respective single bonds participating together in the formation of a fused ring as a 5-membered ring bearing Y.

4. The organic light-emitting compound of claim 1, wherein Z is a substituted or unsubstituted phenanthrene ring in which the substituents $R_{11}$ and $R_{12}$ are respective single bonds participating together in the formation of a fused ring as a 5-membered ring bearing X and the substituents $R_{13}$ and $R_{14}$ are respective single bonds participating together in the formation of a fused ring as a 5-membered ring bearing Y.

5. The organic light-emitting compound of claim 1, being any one selected from among [Compound 1] to [Compound 16], [Compound 18], [Compound 19], [Compound 22] to [Compound 33], [Compound 36] to [Compound 59], [Compound 61] to [Compound 75], [Compound 78] to [Compound 80], [Compound 82] to [Compound 99], [Compound 103], and [Compound 104]:

<Compound 1>

<Compound 2>

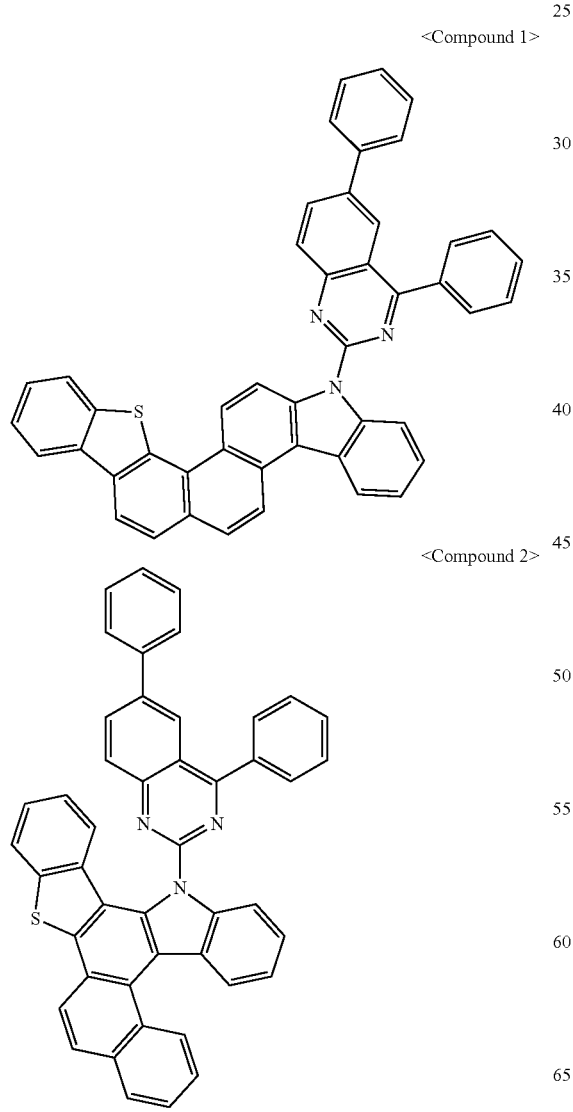

<Compound 3>

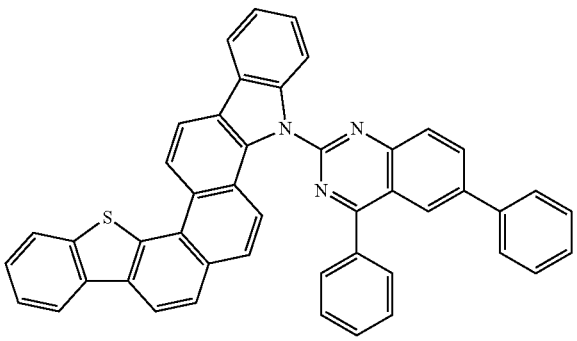

<Compound 4>

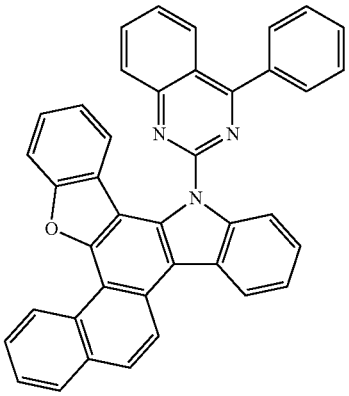

<Compound 5>

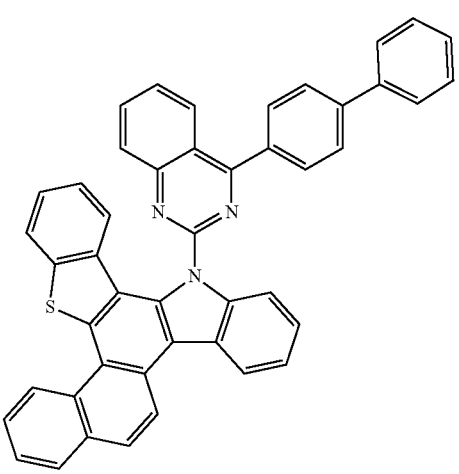

<Compound 6>

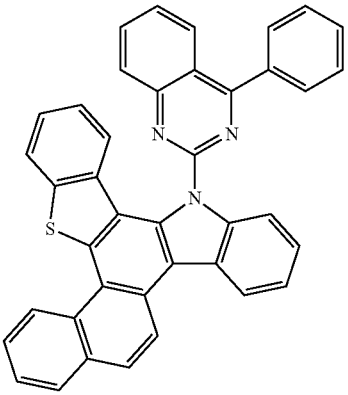

<Compound 7>
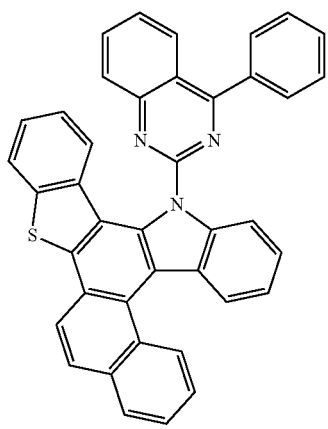
<Compound 8>
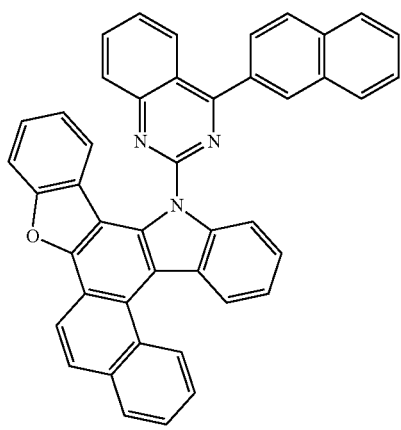
<Compound 9>
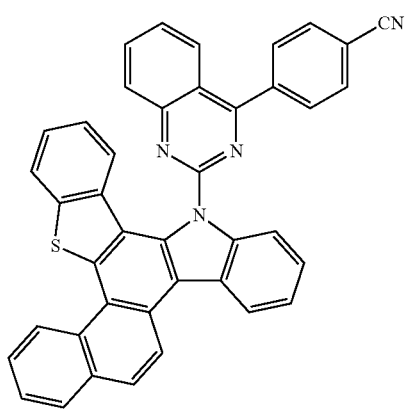
<Compound 10>
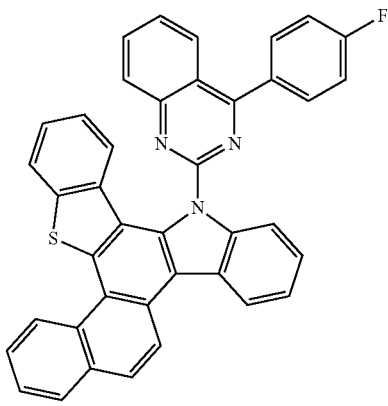
<Compound 11>
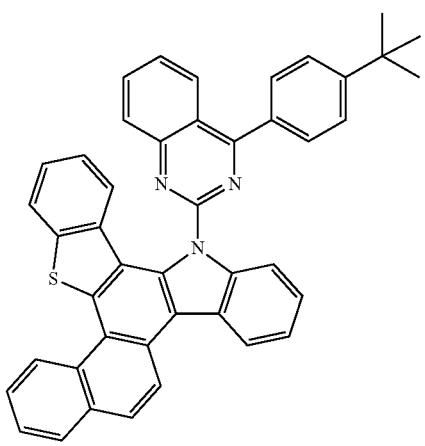
<Compound 12>
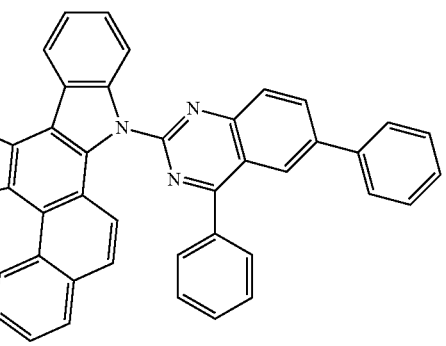

<Compound 13>
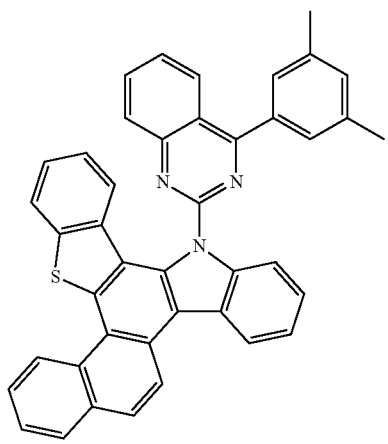
<Compound 14>
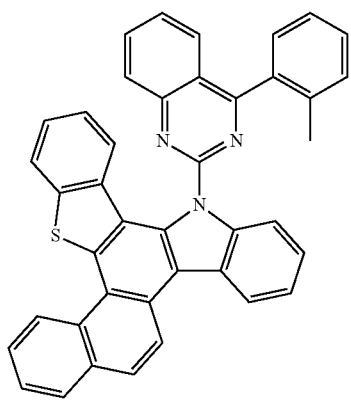
<Compound 15>
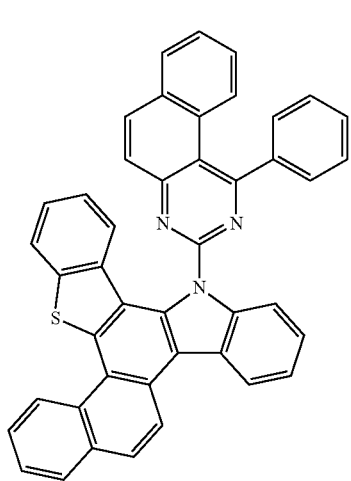
<Compound 16>
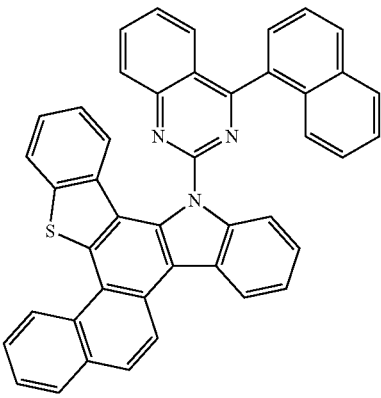
<Compound 18>
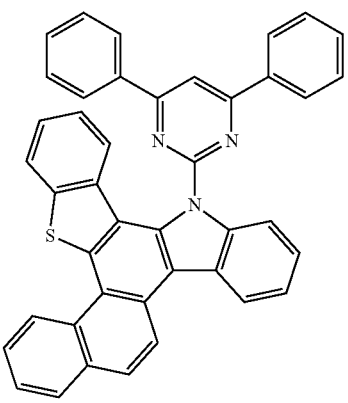
<Compound 19>
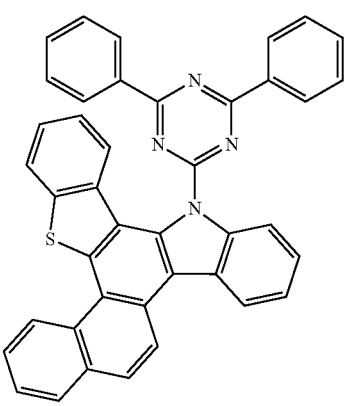
<Compound 22>
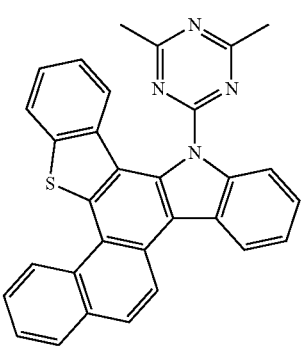

<Compound 23>
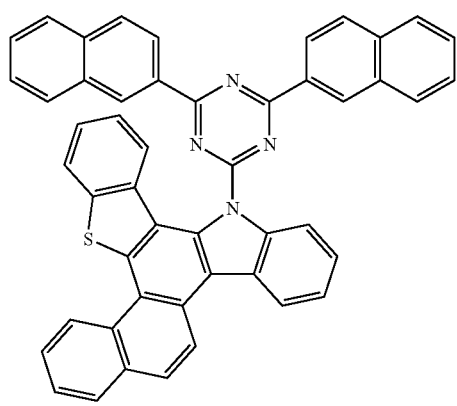
<Compound 24>
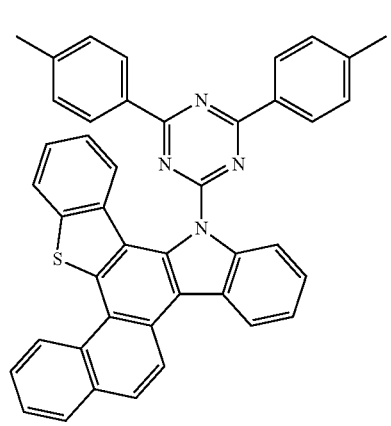
<Compound 25>
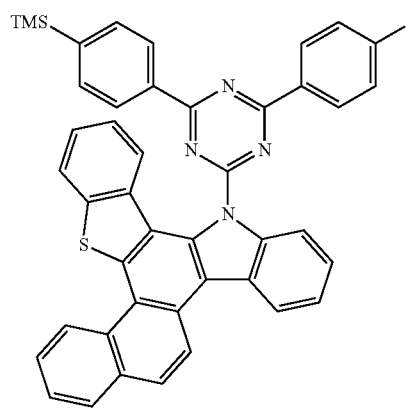
<Compound 26>
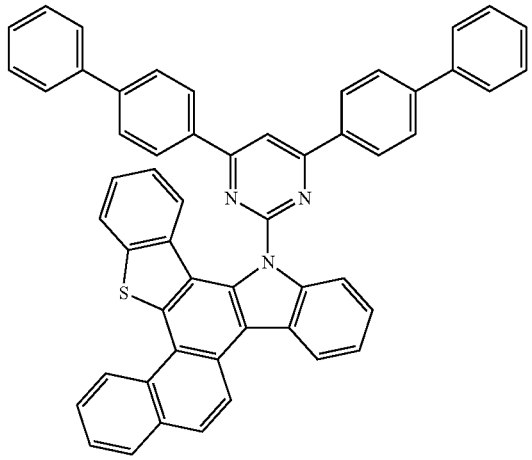
<Compound 27>
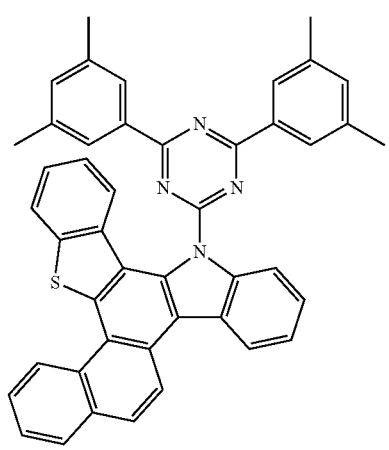
<Compound 28>
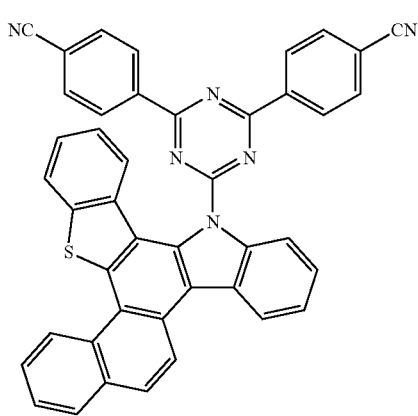

<Compound 29>
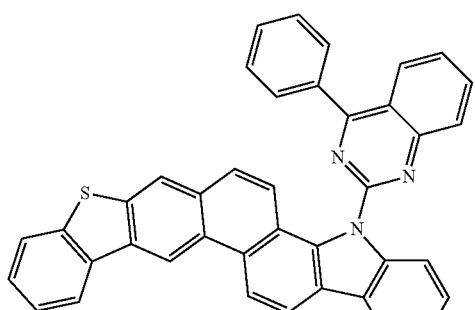
<Compound 30>
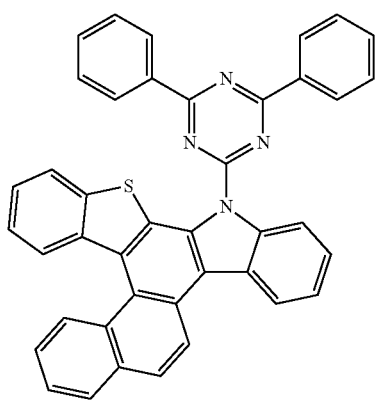
<Compound 31>
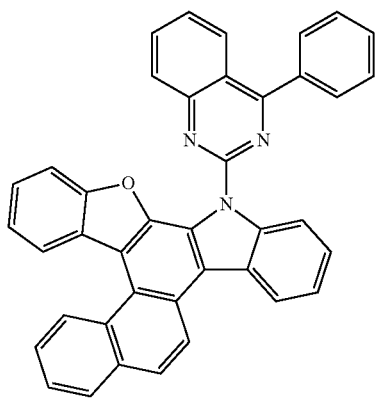
<Compound 32>
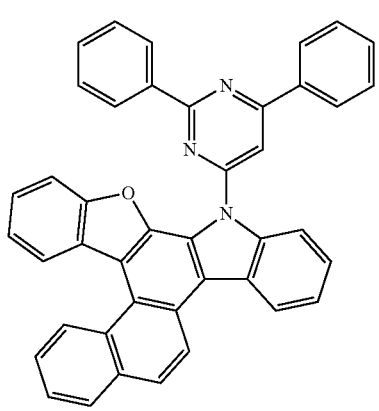
<Compound 33>
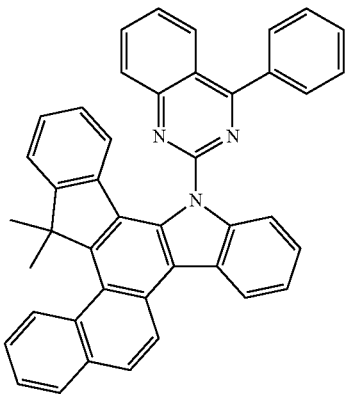
<Compound 36>
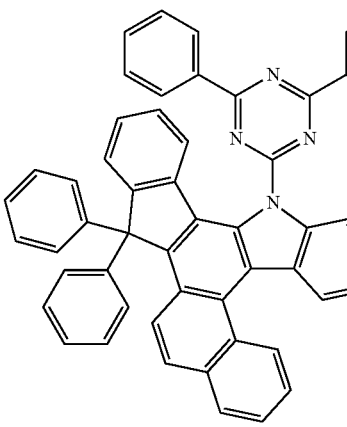
<Compound 37>
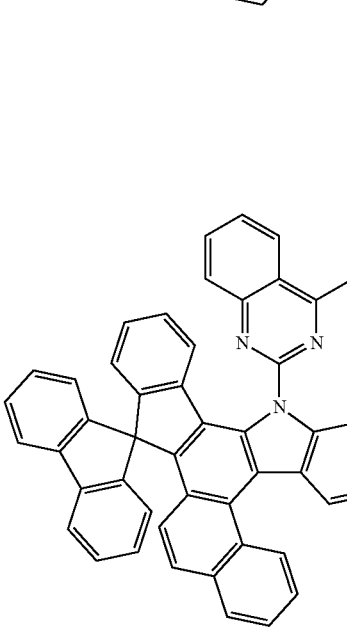

<Compound 38>
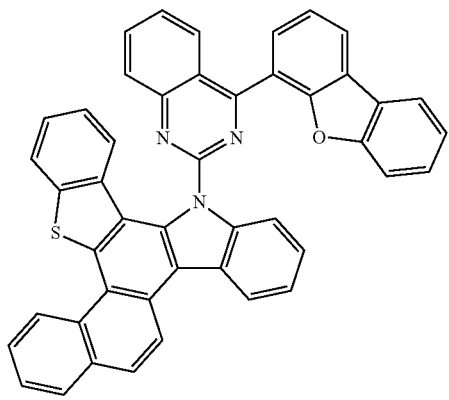
<Compound 42>
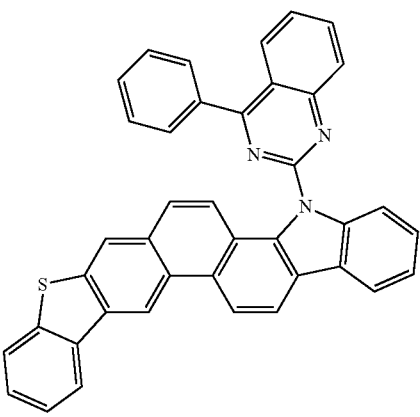
<Compound 39>
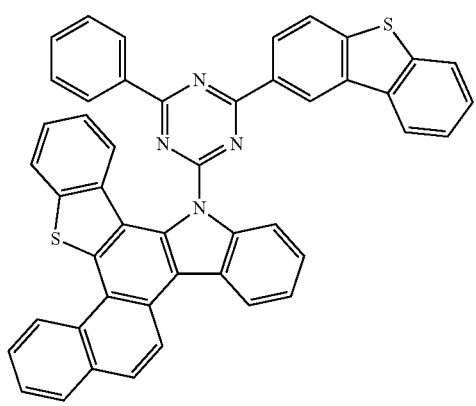
<Compound 43>
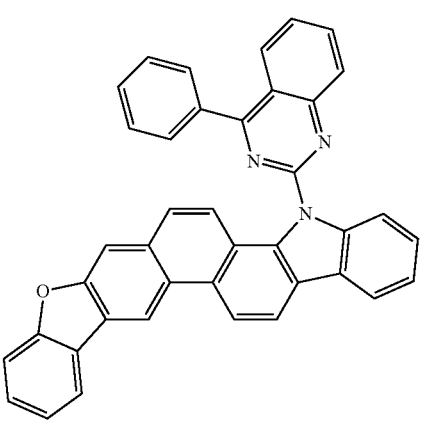
<Compound 40>
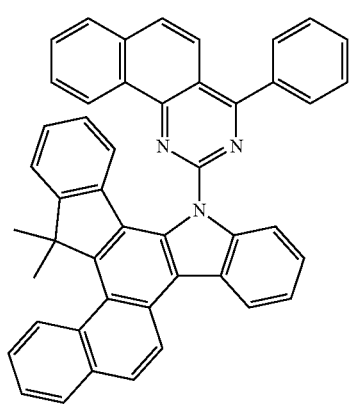
<Compound 41>
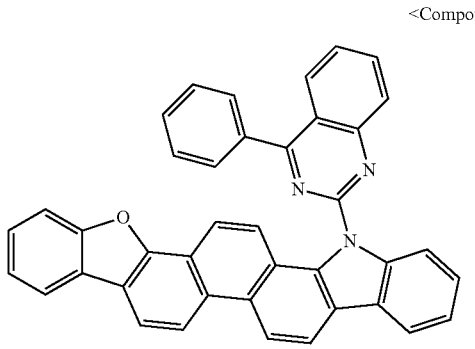
<Compound 44>
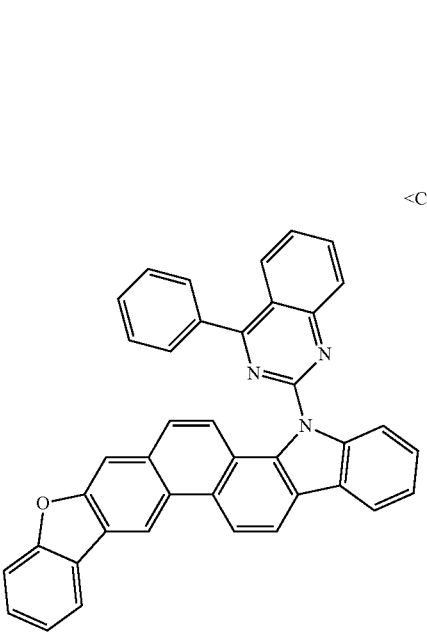

<Compound 45>
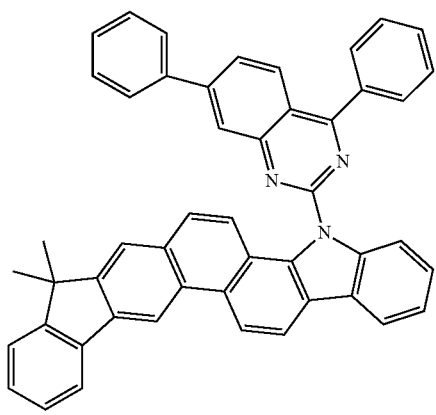
<Compound 46>
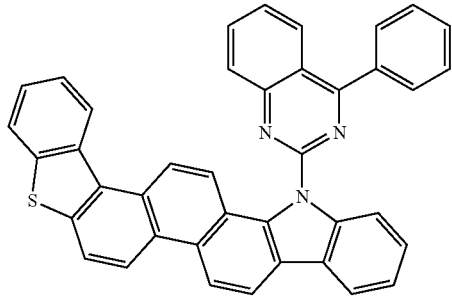
<Compound 47>
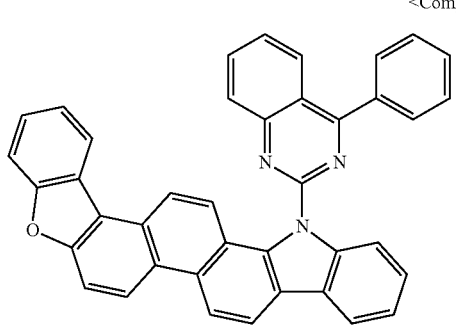
<Compound 48>
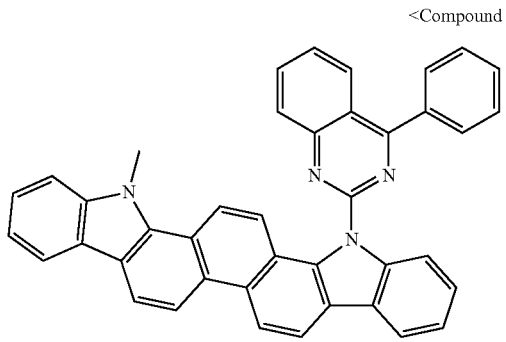
<Compound 49>
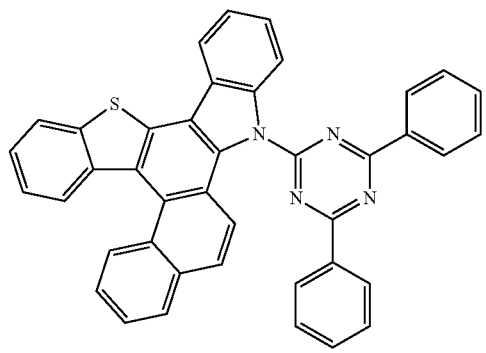
<Compound 50>
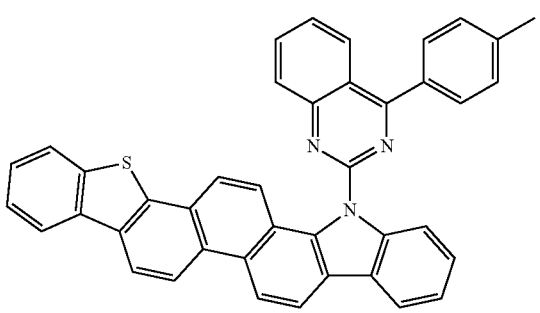
<Compound 51>
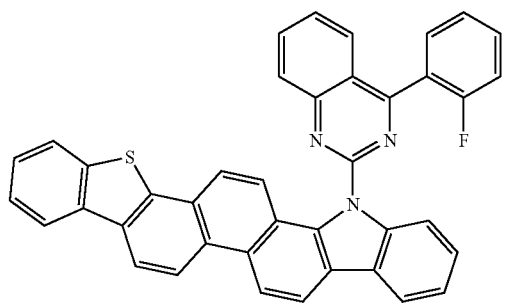
<Compound 52>
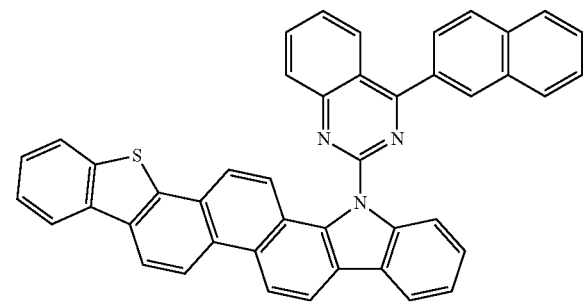

155
-continued
<Compound 53>
<Compound 54>
<Compound 55>
<Compound 56>
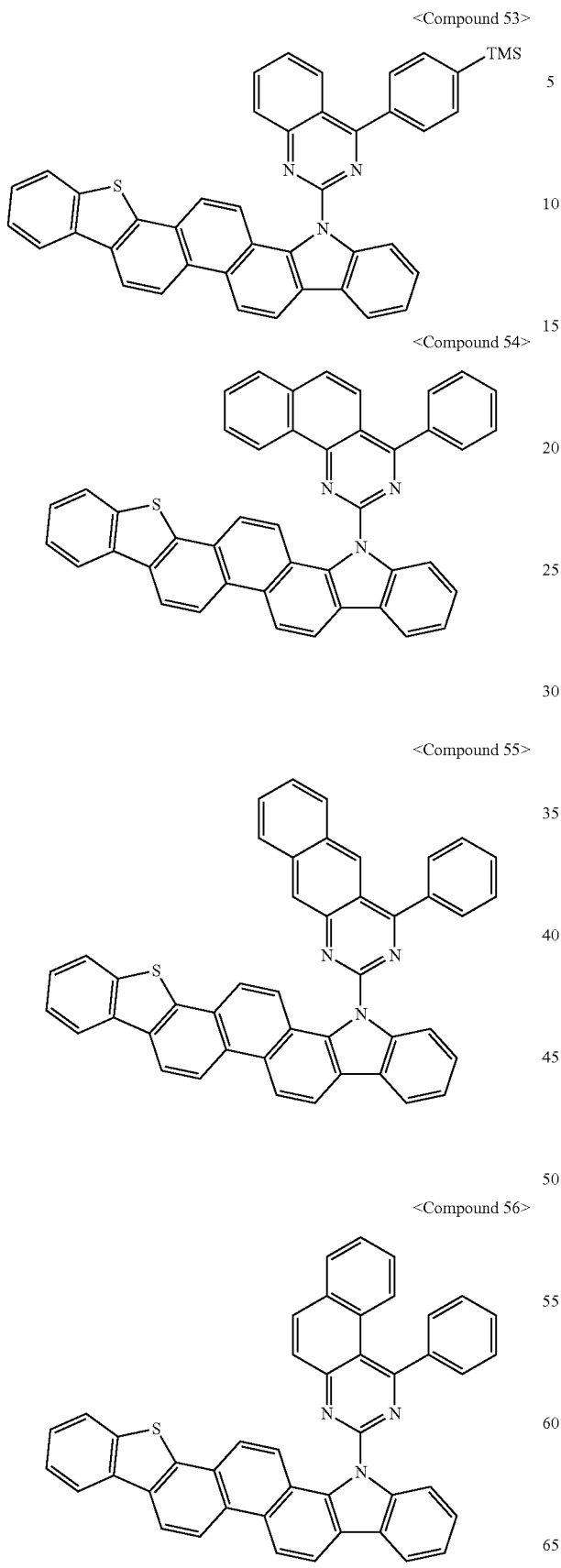
156
-continued
<Compound 57>
<Compound 58>
<Compound 59>
<Compound 61>
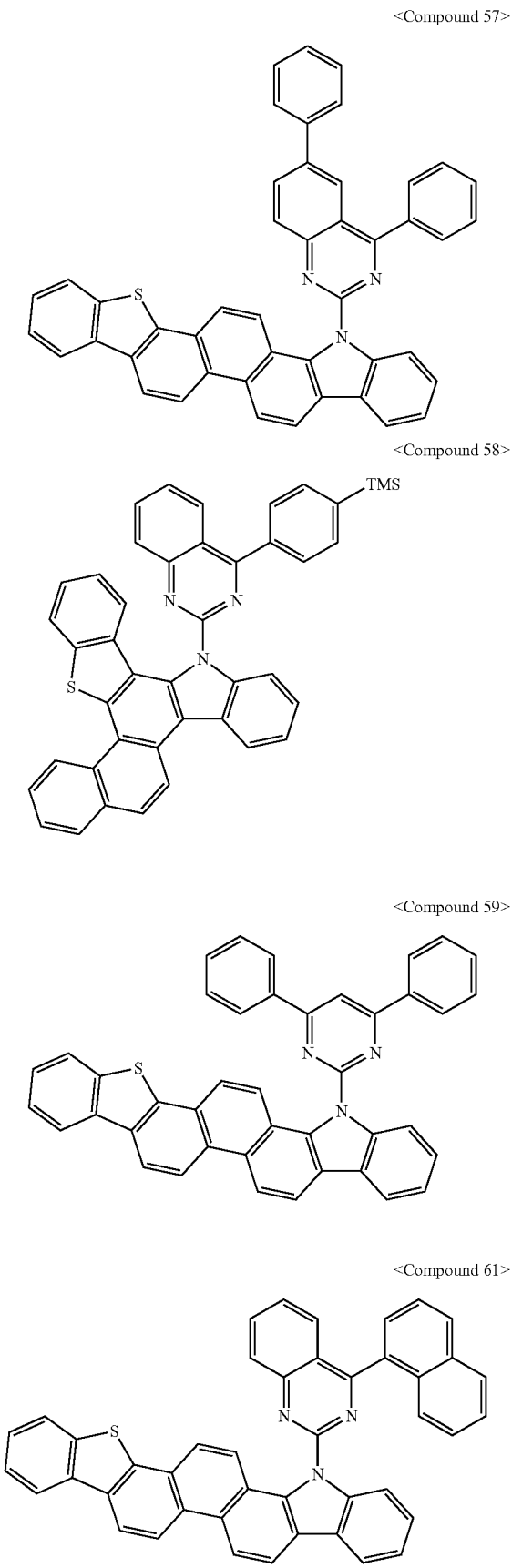

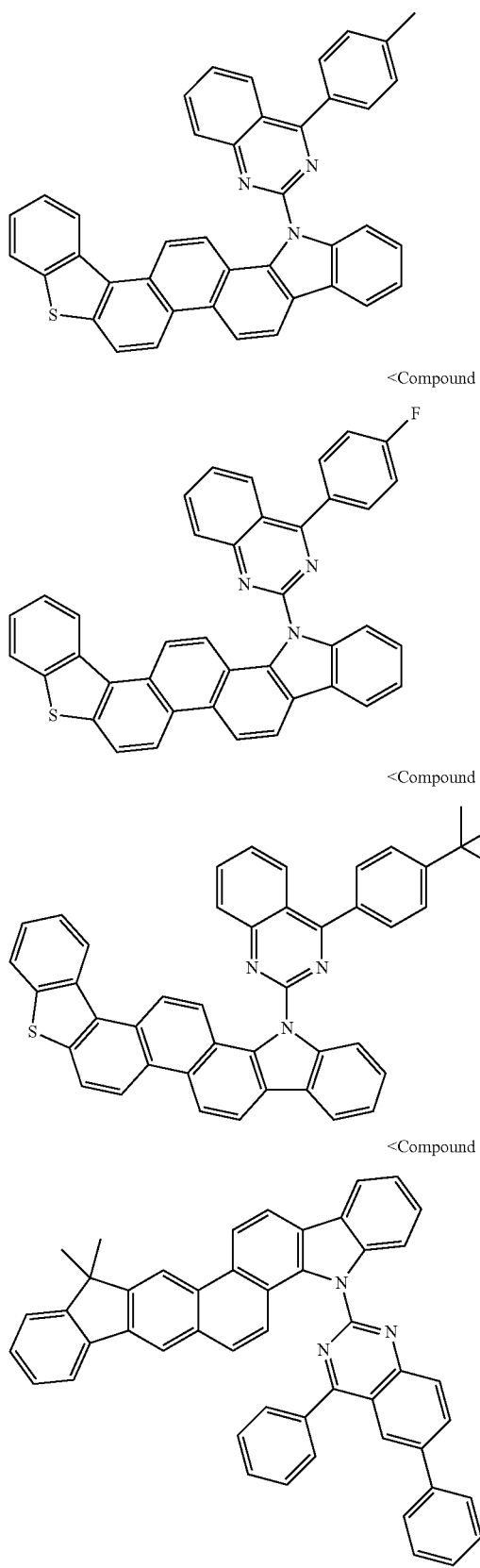
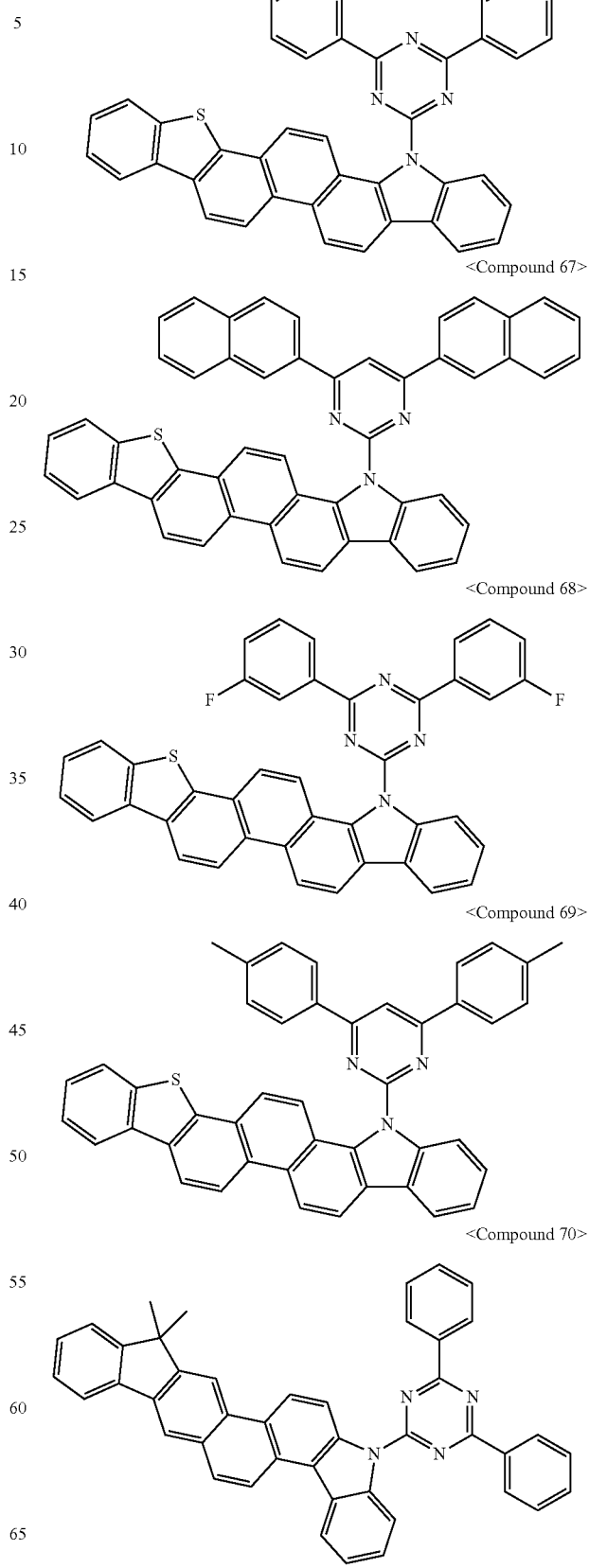

<Compound 71>
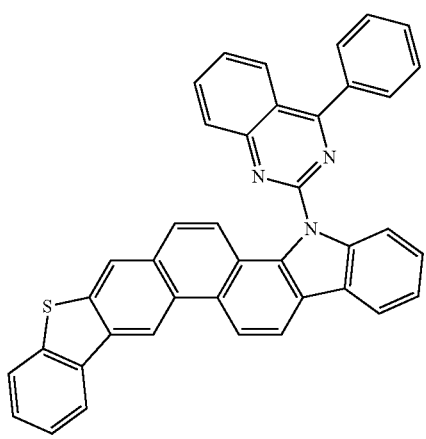
<Compound 72>
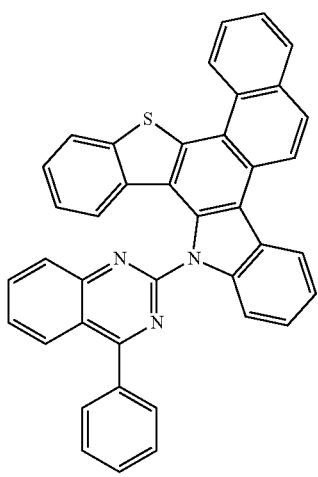
<Compound 73>
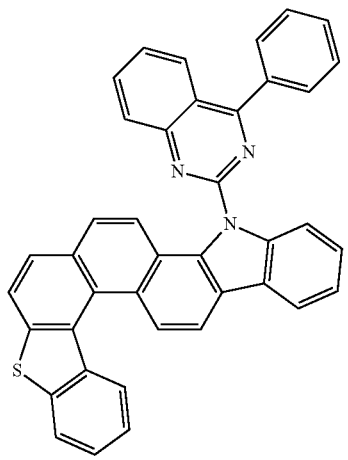
<Compound 74>
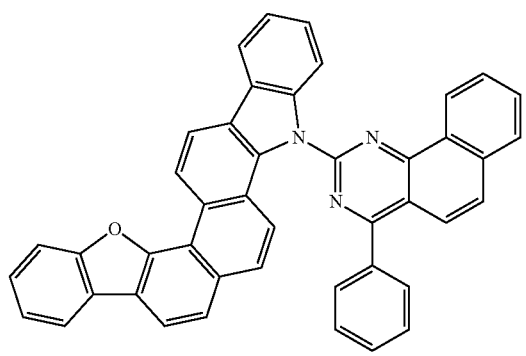
<Compound 75>
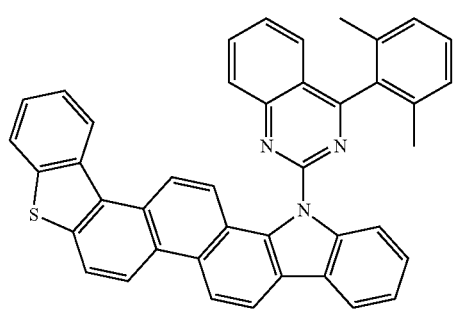
<Compound 78>
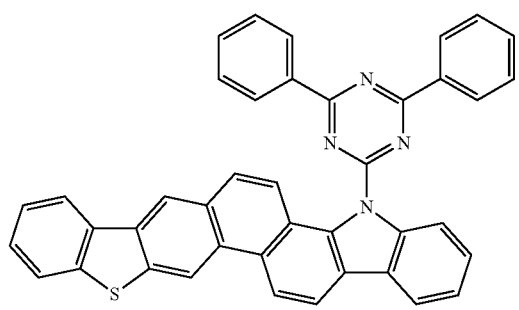
<Compound 79>
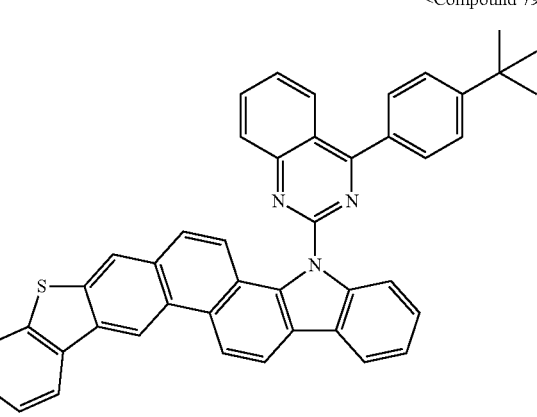

<Compound 80>
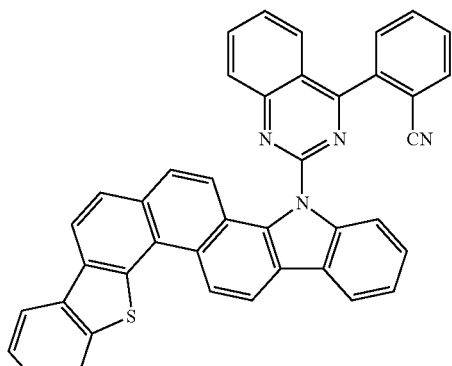
<Compound 82>
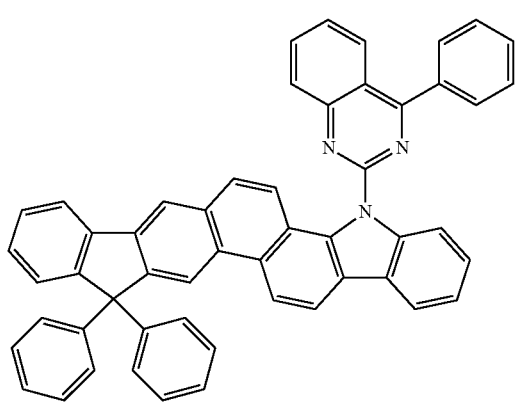
<Compound 83>
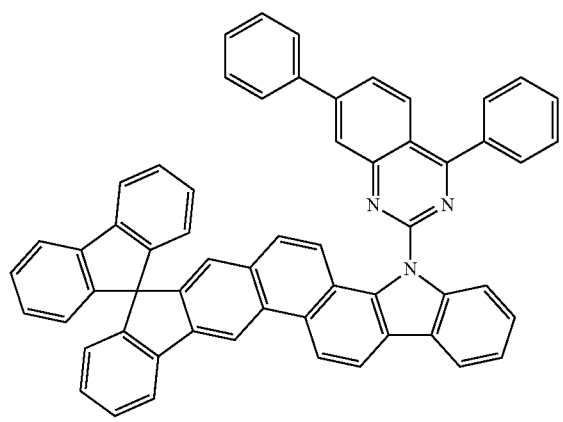
<Compound 84>
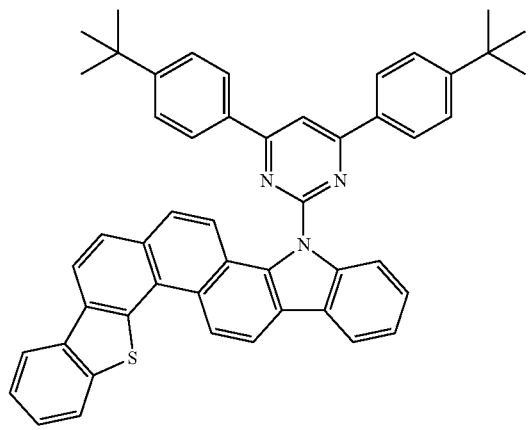
<Compound 85>
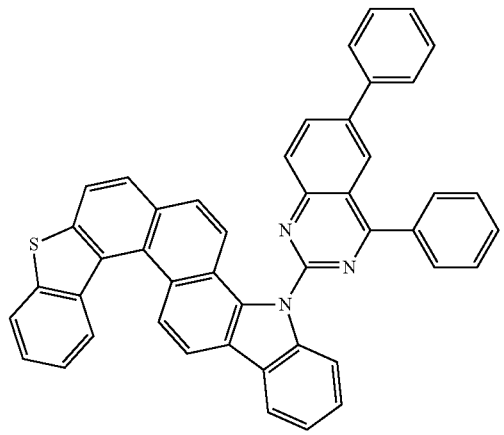
<Compound 86>
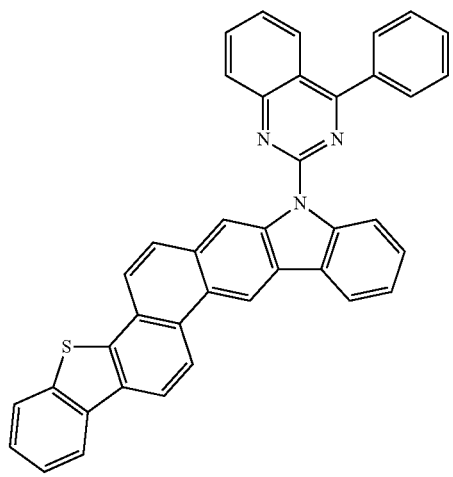

-continued

<Compound 87>

<Compound 88>

<Compound 89>

-continued

<Compound 90>

<Compound 91>

<Compound 92>

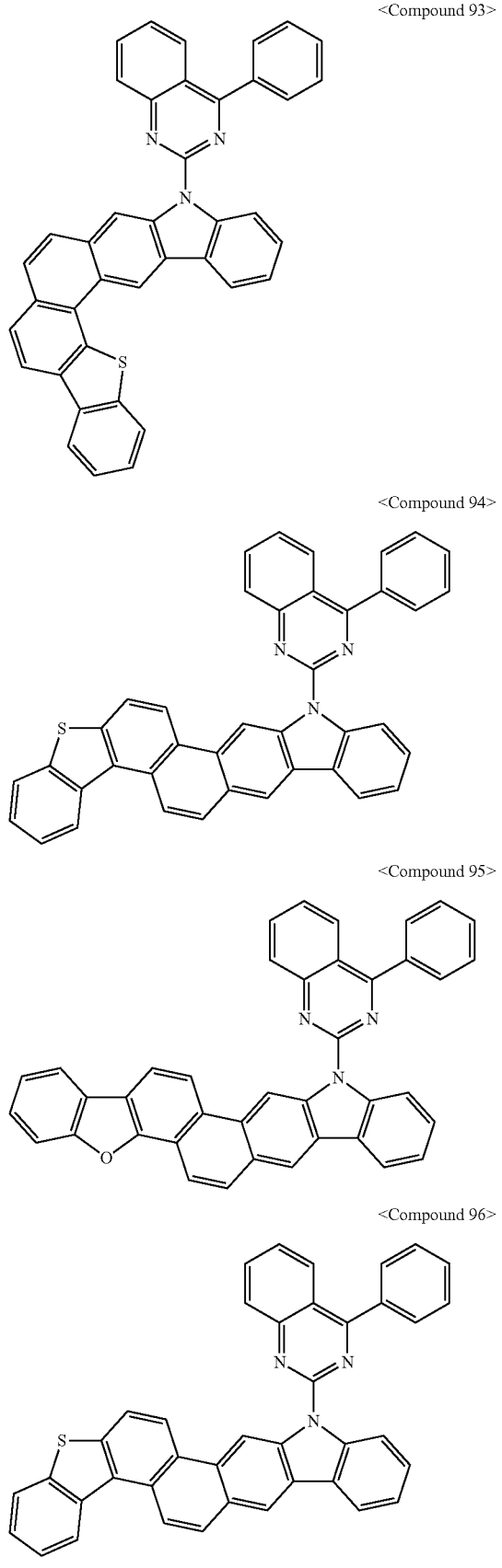
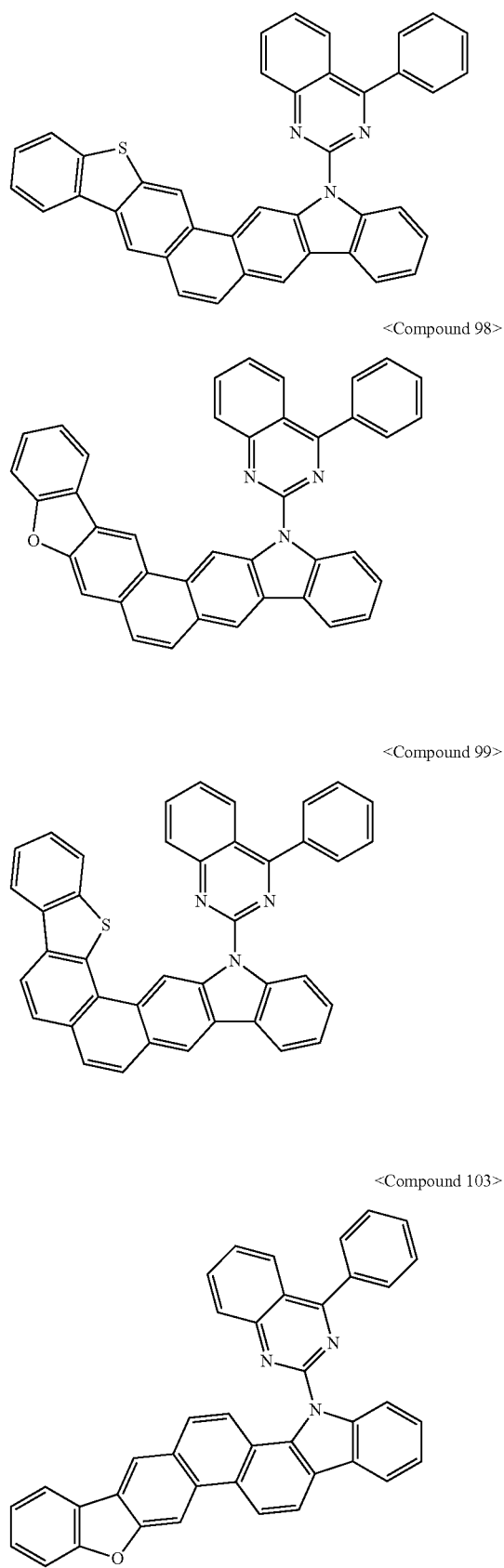

<Compound 104>

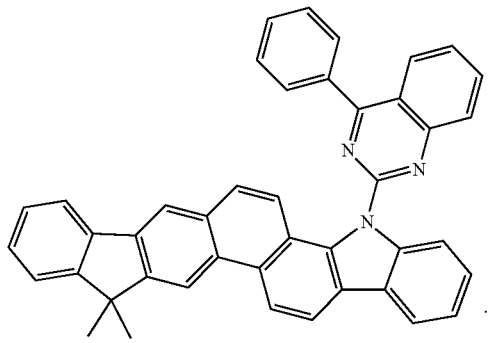

6. An organic light-emitting device, including:
a first electrode;
a second electrode facing the first electrode; and
an organic layer interposed between the first electrode and the second electrode, wherein the organic layer includes at least one selected from among the organic compounds of claim 1.

7. The organic light-emitting device of claim 6, wherein the organic layer includes at least one of a hole injection layer, a hole transport layer, a functional layer capable of both hole injection and hole transport, a light-emitting layer, an electron transport layer, and an electron injection layer.

8. The organic light-emitting device of claim 7, wherein the organic layer interposed between the first electrode and the second electrode includes a light-emitting layer wherein the light emitting layer is composed of a host and a dopant and the organic light-emitting compound is used as a host.

9. The organic light-emitting device of claim 8, wherein the organic layer further includes a hole barrier layer or an electron barrier layer.

10. A device comprising the organic light-emitting device of claim 6, wherein the device is any one selected from the group consisting of a flat display device, a flexible display device, a monochrome or grayscale flat illumination device, and a monochrome or grayscale flexible illumination device.

* * * * *